(12) United States Patent
Frei et al.

(10) Patent No.: US 9,522,886 B2
(45) Date of Patent: Dec. 20, 2016

(54) PYRIDINE DERIVATIVES

(71) Applicant: Hoffmann-La Roche Inc., Little Falls, NJ (US)

(72) Inventors: Beat Frei, Auenstein (CH); Luca Gobbi, Muttenz (CH); Uwe Grether, Efringen-Kirchen (DE); Atsushi Kimbara, Shizuoka (JP); Matthias Nettekoven, Grenzach-Wyhlen (DE); Stephan Roever, Inzlingen (DE); Mark Rogers-Evans, Bottmingen (CH); Tanja Schulz-Gasch, Ziefen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/648,431

(22) PCT Filed: Dec. 2, 2013

(86) PCT No.: PCT/EP2013/075225
§ 371 (c)(1),
(2) Date: May 29, 2015

(87) PCT Pub. No.: WO2014/086705
PCT Pub. Date: Jun. 12, 2014

(65) Prior Publication Data
US 2015/0307452 A1    Oct. 29, 2015

(30) Foreign Application Priority Data

Dec. 7, 2012   (EP) ..................... 12196022

(51) Int. Cl.
| | | |
|---|---|---|
| *C07D 213/81* | (2006.01) | |
| *C07D 401/14* | (2006.01) | |
| *C07D 401/04* | (2006.01) | |
| *C07D 405/14* | (2006.01) | |
| *C07D 405/12* | (2006.01) | |
| *C07D 401/12* | (2006.01) | |
| *C07D 413/14* | (2006.01) | |
| *C07D 413/12* | (2006.01) | |
| *C07D 417/12* | (2006.01) | |
| *C07D 417/14* | (2006.01) | |

(52) U.S. Cl.
CPC .......... *C07D 213/81* (2013.01); *C07D 401/04* (2013.01); *C07D 401/12* (2013.01); *C07D 401/14* (2013.01); *C07D 405/12* (2013.01); *C07D 405/14* (2013.01); *C07D 413/12* (2013.01); *C07D 413/14* (2013.01); *C07D 417/12* (2013.01); *C07D 417/14* (2013.01)

(58) Field of Classification Search
None
See application file for complete search history.

(56) References Cited

U.S. PATENT DOCUMENTS

| 7,691,863 B2 * | 4/2010 | Dietz ................... C07D 241/26 514/255.05 |
|---|---|---|
| 2008/0085905 A1 | 4/2008 | Dietz et al. |
| 2012/0065212 A1 | 3/2012 | Hebeisen et al. |

FOREIGN PATENT DOCUMENTS

| WO | 2008/040649 A2 | 4/2008 |
|---|---|---|
| WO | 2012/032018 A1 | 3/2012 |
| WO | 2012/168350 A1 | 12/2012 |

OTHER PUBLICATIONS

Dubois et al., "A new pathway to substituted 6-chloro-2-pyridinecarboxylic acid derivatives from the reaction of 4,6-dichloro-2-oxa-5-aza-bicyclo[2.2.2]oct-5-en-3-ones with nucleophiles" Tetrahedron 52(20):6997-7002 (1996).
International Search Report issued in International Application No. PCT/EP2013/075225, dated Jan. 17, 2014 (in 2 pages).
International Search Report issued in International Application No. PCT/EP2013/075442, dated Feb. 17, 2014 (in 2 pages).
International Search Report issued in International Application No. PCT/EP2013/075443, dated Feb. 18, 2014 (in 3 pages).
International Search Report issued in International Application No. PCT/EP2013/075444, dated Jan. 22, 2014 (in 4 pages).
Sammakia et al., "Total Synthesis of Caerulomycin C via the Halogen Dance Reaction" Organic Letters 4(14):2385-2388 (2002).

\* cited by examiner

*Primary Examiner* — Timothy R Rozof
(74) *Attorney, Agent, or Firm* — Alex Andrus

(57) ABSTRACT

The invention relates to a compound of formula (I) wherein $R^1$ to $R^3$ are defined as in the description and in the claims. The compound of formula (I) can be used as a medicament.

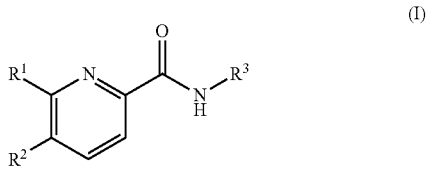

(I)

18 Claims, No Drawings

PYRIDINE DERIVATIVES

CROSS-REFERENCE TO RELATED APPLICATIONS

This application is a 371 application of International Application No. PCT/EP2013/075225, filed on Dec. 2, 2013, which claims priority to European Patent Application No. 12196022.3, filed on Dec. 7, 2012, the entire contents of which are incorporated herein by reference.

The present invention relates to organic compounds useful for therapy and/or prophylaxis in a mammal, and in particular to compounds that are preferential agonists of the Cannabinoid Receptor 2.

The invention relates in particular to a compound of formula (I)

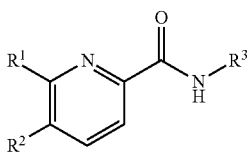

wherein $R^1$ is halogen, cycloalkylalkoxy, haloalkoxy, alkylsulfonyl, alkylsulfinyl, halophenylalkyl, alkylsulfanyl, oxanylalkoxy, halophenyl or oxolanylalkoxy;

$R^2$ is halogen, cycloalkyl, haloalkyl, haloalkoxy, haloazetidinyl, cycloalkyloxy, halocycloalkyl, hydroxycycloalkyl, hydroxyazetidinyl, hydroxyoxetanyl or halooxetanyl;

$R^3$ is (alkyl)(oxo)pyrrolidinyl or —C($R^4R^5$)—C($R^6R^7$)—C(O)—$R^8$;

$R^4$ and $R^5$ are independently selected from hydrogen, alkyl, phenyl, phenylalkyl, cycloalkyl, tetrahydropyranyl, haloalkyl, halophenyl and oxolanyl;

or $R^4$ and $R^5$ together with the carbon atom to which they are attached form cycloalkyl, oxetanyl, thiethanyl, 1,1-dioxo-1λ6-thiethanyl, azetidinyl, haloazetidinyl, 2-oxa-spiro[3.3]heptyl, tetrahydrofuranyl, pyrrolidinyl, oxopyrrolidinyl, 1,1-dioxo-1λ6-isothiazolidinyl, 1,1-dioxo-tetrahydro-1λ6-thiophenyl, tetrahydrothiophenyl, tetrahydropyranyl, piperidinyl, oxopiperidinyl, tetrahydrothiopyranyl, 2-oxo-[1,3]oxazinanyl, 1,1-dioxo-1λ6-[1,2]thiazinanyl, 2-oxo-hexahydro-pyrimidinyl, 1,1-dioxo-hexahydro-1λ6-thiopyranyl, 2-oxo-[1,3]dioxanyl, 1,1-dioxothianyl, alkylcarbonylpiperidinyl, alkylcarbonylazetidinyl, phenylalkyloxycarbonylazetidinyl, oxolanyl, or phenylalkyloxycarbonylpyrrolidinyl;

$R^6$ and $R^7$ are independently selected from hydrogen and alkyl;

or one of $R^4$ and $R^5$ and one of $R^6$ and $R^7$, together with the carbon atoms to which they are attached, form cycloalkyl, and the other ones are both hydrogen at the same time; and $R^8$ is —$NH_2$, alkoxy, alkylamino or hydroxyl;

or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, brakykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl, isopropyl, butyl, isobutyl, tert.-butyl and pentyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl and cyclohexyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. Particular "alkoxy" are methoxy, ethoxy and tert.-butoxy.

The term "oxy", alone or in combination, signifies the —O— group.

The term "oxo", alone or in combination, signifies the =O group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. A particular "halogen" is fluorine.

The term "haloalkyl", alone or in combination, denotes an alkyl group substituted with at least one halogen, particularly substituted with one to five halogens, particularly one to three halogens. A particular "haloalkyl" is trifluoromethyl.

The term "haloalkoxy" or "haloalkyloxy", alone or in combination, denotes an alkoxy group substituted with at least one halogen, particularly substituted with one to five halogens, particularly one to three halogens. Particular "haloalkoxy" are pentafluoropropyloxy, trifluoropropyloxy and trifluoromethoxy.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—NH$_2$), the secondary amino group (—NH—), or the tertiary amino group (—N—).

The term "aminocarbonyl", alone or in combination, signifies the —C(O)—NH$_2$, —C(O)—NH— or —C(O)—N— group.

The term "sulfonyl", alone or in combination, signifies the —S(O)$_2$— group.

The term "sulfinyl", alone or in combination, signifies the —S(O)— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to a compound of formula (I) wherein:
  $R^1$ is halogen, cycloalkylalkoxy, haloalkoxy, alkylsulfonyl or alkylsulfinyl;
  $R^2$ is halogen, cycloalkyl, haloalkyl, haloalkoxy, haloazetidinyl or cycloalkyloxy;
  $R^4$ and $R^5$ are independently selected from hydrogen, alkyl, phenyl, phenylalkyl, cycloalkyl, tetrahydropyranyl, haloalkyl and halophenyl;
  or $R^4$ and $R^5$ together with the carbon atom to which they are attached form cycloalkyl, oxetanyl, thiethanyl, 1,1-dioxo-1λ6-thiethanyl, azetidinyl, haloazetidinyl, 2-oxa-spiro[3.3]heptyl, tetrahydrofuranyl, pyrrolidinyl, oxopyrrolidinyl, 1,1-dioxo-1λ6-isothiazolidinyl, 1,1-dioxo-tetrahydro-1λ6-thiophenyl, tetrahydrothiophenyl, tetrahydropyranyl, piperidinyl, oxopiperidinyl, tetrahydrothiopyranyl, 2-oxo-[1,3]oxazinanyl, 1,1-dioxo-1λ6-[1,2]thiazinanyl, 2-oxo-hexahydro-pyrimidinyl, 1,1-dioxo-hexahydro-1λ6-thiopyranyl or 2-oxo-[1,3]dioxanyl; and
  or one of $R^4$ and $R^5$ and one of $R^6$ and $R^7$, together with the carbon atoms to which they are attached, form cycloalkyl, and the other ones are both hydrogen at the same time.

The invention further relates in particular to:
A compound of formula (I) wherein $R^1$ is cycloalkylalkoxy, haloalkoxy, halophenylalkyl or oxolanylalkoxy;
A compound of formula (I) wherein $R^1$ is cyclopropylmethoxy, pentafluoropropyloxy, fluorophenylmethyl, butylsulfanyl, oxanylmethoxy, chlorofluorophenyl, oxolanylmethoxy, fluoroehtoxy, difluoroethoxy or difluoropropyloxy;
A compound of formula (I) wherein $R^1$ is cyclopropylmethoxy, pentafluoropropyloxy, fluorophenylmethyl or oxolanylmethoxy;
A compound of formula (I) wherein $R^1$ is cycloalkylalkoxy or haloalkoxy;
A compound of formula (I) wherein $R^1$ is cyclopropylmethoxy or pentafluoropropyloxy;
A compound of formula (I) wherein $R^2$ is cycloalkyl, haloazetidinyl, halocycloalkyl, hydroxycycloalkyl, haloalkyl or halooxetanyl;
A compound of formula (I) wherein $R^2$ is bromo, trifluoromethoxy, cyclopropyl, difluoroazetidinyl, fluorocyclobutyl, hydroxycyclobutyl fluorooxetanyl or trifluoromethyl;
A compound of formula (I) wherein $R^2$ is cyclopropyl, difluoroazetidinyl, fluorocyclobutyl, hydroxycyclobutyl or trifluoromethyl;
A compound of formula (I) wherein $R^2$ is cycloalkyl or haloazetidinyl;
A compound of formula (I) wherein $R^2$ is cyclopropyl or difluoroazetidinyl;
A compound of formula (I) wherein $R^3$ is (methyl)(oxo)pyrrolidinyl or —C($R^4R^5$)—C($R^6R^7$)—C(O)—$R^8$;
A compound of formula (I) wherein $R^3$ is —C($R^4R^5$)—C($R^6R^7$)—C(O)—$R^8$;
A compound of formula (I) wherein one of $R^4$ and $R^5$ is hydrogen or alkyl, and the other one is independently selected from alkyl, haloalkyl, phenyl, cycloalkyl and tetrahydropyranyl;
A compound of formula (I) wherein one of $R^4$ and $R^5$ is hydrogen or methyl, and the other one is independently selected from methyl, trifluoromethyl, phenyl, cyclohexyl, cyclopropyl and tetrahydropyranyl;
A compound of formula (I) wherein $R^4$ and $R^5$ together with the carbon atom to which they are attached form oxetanyl, 1,1-dioxo-1λ6-thiethanyl, piperidinyl, cycloalkyl, oxolanyl or thiethanyl;
A compound of formula (I) wherein $R^4$ and $R^5$ together with the carbon atom to which they are attached form oxetanyl, oxopyrrolidinyl, tert-butyloxycarbonylpiperidinyl, 1,1-dioxo-1λ6-thiethanyl, 1,1-dioxothianyl, piperidinyl, tetrahydropyranyl, cyclobutyl, oxolanyl, thiethanyl, methylcarbonylpiperidinyl, methylcarbonylazetidinyl, phenylmethoxycarbonylazetidinyl or phenylmethoxycarbonylpyrrolidinyl;
A compound of formula (I) wherein $R^4$ and $R^5$ together with the carbon atom to which they are attached form oxetanyl or 1,1-dioxo-1λ6-thiethanyl;
A compound of formula (I) wherein $R^6$ and $R^7$ are both hydrogen at the same time;
A compound of formula (I) wherein one of $R^4$ and $R^5$ and one of $R^6$ and $R^7$, together with the carbon atoms to which they are attached, form cyclohexyl, and the other ones are both hydrogen at the same time;
A compound of formula (I) wherein $R^8$ is —$NH_2$, ethoxy, tert.-butoxy, methylamino, hydroxyl, dimethylamino or methoxy; and A compound of formula (I) wherein $R^8$ is —$NH_2$ or ethoxy.

The invention relates in particular to a compound of formula (I) selected from:

{3-[(5-Cyclopropyl-6-cyclopropylmethoxy-pyridine-2-carbonyl)-amino]-oxetan-3-yl}-acetic acid ethyl ester;
tert-Butyl 3-({[6-(cyclopropylmethoxy)-5-(3,3-difluoroazetidin-1-yl)pyridin-2-yl]carbonyl}amino)-5-methylhexanoate;
6-Cyclopropylmethoxy-5-(3,3-difluoro-azetidin-1-yl)-pyridine-2-carboxylic acid (1-methyl-5-oxo-pyrrolidin-3-yl)-amide;
3-{[6-Cyclopropylmethoxy-5-(3,3-difluoro-azetidin-1-yl)-pyridine-2-carbonyl]-amino}-3-phenyl-propionic acid ethyl ester;
3-{[6-Cyclopropylmethoxy-5-(3,3-difluoro-azetidin-1-yl)-pyridine-2-carbonyl]-amino}-3-methyl-butyric acid ethyl ester;
6-Cyclopropylmethoxy-5-(3,3-difluoro-azetidin-1-yl)-pyridine-2-carboxylic acid (1,1-dimethyl-2-methylcarbamoyl-ethyl)-amide;
6-Cyclopropylmethoxy-5-(3,3-difluoro-azetidin-1-yl)-pyridine-2-carboxylic acid (1-methylcarbamoylmethyl-hexyl)-amide;
6-Cyclopropylmethoxy-5-(3,3-difluoro-azetidin-1-yl)-pyridine-2-carboxylic acid (1-methylcarbamoylmethyl-3-phenyl-propyl)-amide;
(−)-5-Cyclopropyl-6-cyclopropylmethoxy-pyridine-2-carboxylic acid (1-carbamoylmethyl-pentyl)-amide;
(+)-5-Cyclopropyl-6-cyclopropylmethoxy-pyridine-2-carboxylic acid (1-carbamoylmethyl-pentyl)-amide;
2-[({[6-(Cyclopropylmethoxy)-5-(3,3-difluoroazetidin-1-yl)pyridin-2-yl]carbonyl}amino)methyl]-4-methylpentanoic acid;
5-Cyclopropyl-6-cyclopropylmethoxy-pyridine-2-carboxylic acid (rel-(1S,2R)-2-carbamoyl-cyclohexyl)-amide;
5-Cyclopropyl-6-cyclopropylmethoxy-pyridine-2-carboxylic acid ((R)-1-carbamoylmethyl-2-methyl-propyl)-amide;
5-Cyclopropyl-6-cyclopropylmethoxy-pyridine-2-carboxylic acid ((S)-1-carbamoylmethyl-2-methyl-propyl)-amide;
(+)-cis-5-Cyclopropyl-6-cyclopropylmethoxy-pyridine-2-carboxylic acid (2-carbamoyl-cyclohexyl)-amide;
(−)-trans-5-Cyclopropyl-6-cyclopropylmethoxy-pyridine-2-carboxylic acid (2-carbamoyl-cyclohexyl)-amide;
(−)-5-Cyclopropyl-6-cyclopropylmethoxy-pyridine-2-carboxylic acid (2-carbamoyl-1-cyclohexyl-ethyl)-amide;
(+)-5-Cyclopropyl-6-cyclopropylmethoxy-pyridine-2-carboxylic acid (2-carbamoyl-1-cyclohexyl-ethyl)-amide;
6-Cyclopropylmethoxy-5-(3,3-difluoro-azetidin-1-yl)-pyridine-2-carboxylic acid ((S)-1-carbamoylmethyl-2-methyl-propyl)-amide;
(+)-cis-6-Cyclopropylmethoxy-5-(3,3-difluoro-azetidin-1-yl)-pyridine-2-carboxylic acid (2-carbamoyl-cyclohexyl)-amide;
(−)-cis-6-Cyclopropylmethoxy-5-(3,3-difluoro-azetidin-1-yl)-pyridine-2-carboxylic acid (2-carbamoyl-cyclohexyl)-amide;
3-[(5-Cyclopropyl-6-cyclopropylmethoxy-pyridine-2-carbonyl)-amino]-5-methyl-hexanoic acid ethyl ester;
5-Cyclopropyl-6-cyclopropylmethoxy-pyridine-2-carboxylic acid (3-carbamoylmethyl-oxetan-3-yl)-amide;
(−)-5-Cyclopropyl-6-cyclopropylmethoxy-pyridine-2-carboxylic acid (1-carbamoylmethyl-3-methyl-butyl)-amide;
(+)-5-Cyclopropyl-6-cyclopropylmethoxy-pyridine-2-carboxylic acid (1-carbamoylmethyl-3-methyl-butyl)-amide;
6-Cyclopropylmethoxy-5-(3,3-difluoro-azetidin-1-yl)-pyridine-2-carboxylic acid (3-carbamoylmethyl-oxetan-3-yl)-amide;
(−)-5-Cyclopropyl-6-cyclopropylmethoxy-pyridine-2-carboxylic acid (2-carbamoyl-1-cyclopropyl-ethyl)-amide;
(+)-5-Cyclopropyl-6-cyclopropylmethoxy-pyridine-2-carboxylic acid (2-carbamoyl-1-cyclopropyl-ethyl)-amide;
5-Cyclopropyl-6-cyclopropylmethoxy-pyridine-2-carboxylic acid ((R)-1-carbamoylmethyl-2,2-dimethyl-propyl)-amide;
5-Cyclopropyl-6-cyclopropylmethoxy-pyridine-2-carboxylic acid [2-carbamoyl-1-(tetrahydro-pyran-4-yl)-ethyl]-amide;
(−)-5-Cyclopropyl-6-cyclopropylmethoxy-pyridine-2-carboxylic acid (1-carbamoylmethyl-2,2,2-trifluoro-ethyl)-amide;
(+)-5-Cyclopropyl-6-cyclopropylmethoxy-pyridine-2-carboxylic acid (1-carbamoylmethyl-2,2,2-trifluoro-ethyl)-amide;
5-Cyclopropyl-6-(2,2,2-trifluoro-1-methyl-ethoxy)-pyridine-2-carboxylic acid (3-carbamoylmethyl-oxetan-3-yl)-amide;
(−)-5-Cyclopropyl-6-cyclopropylmethoxy-pyridine-2-carboxylic acid [2-carbamoyl-1-(tetrahydro-pyran-4-yl)-ethyl]-amide;
5-Cyclopropyl-6-cyclopropylmethoxy-pyridine-2-carboxylic acid ((S)-1-carbamoylmethyl-2,2-dimethyl-propyl)-amide;
5-Cyclopropyl-6-(2-methyl-propane-1-sulfonyl)-pyridine-2-carboxylic acid (3-carbamoylmethyl-oxetan-3-yl)-amide;
6-Cyclopropylmethoxy-5-(3,3-difluoro-azetidin-1-yl)-pyridine-2-carboxylic acid (3-methylcarbamoylmethyl-oxetan-3-yl)-amide;
5-Cyclopropyl-6-cyclopropylmethoxy-pyridine-2-carboxylic acid (3-methylcarbamoylmethyl-oxetan-3-yl)-amide;
6-Cyclopropylmethoxy-5-trifluoromethyl-pyridine-2-carboxylic acid (3-methylcarbamoylmethyl-oxetan-3-yl)-amide;
5-Cyclopropyl-6-cyclopropylmethoxy-pyridine-2-carboxylic acid (3-dimethylcarbamoylmethyl-oxetan-3-yl)-amide;
6-Cyclopropylmethoxy-5-(3,3-difluoro-azetidin-1-yl)-pyridine-2-carboxylic acid (3-dimethylcarbamoylmethyl-oxetan-3-yl)-amide;
6-Cyclopropylmethoxy-5-trifluoromethyl-pyridine-2-carboxylic acid (3-dimethylcarbamoylmethyl-oxetan-3-yl)-amide;
5-Cyclopropyl-6-cyclopropylmethoxy-pyridine-2-carboxylic acid [(R)-2-carbamoyl-1-(3-chloro-phenyl)-ethyl]-amide;
5-Bromo-6-(propane-2-sulfinyl)-pyridine-2-carboxylic acid (3-carbamoylmethyl-oxetan-3-yl)-amide;
4-[(5-Cyclopropyl-6-cyclopropylmethoxy-pyridine-2-carbonyl)-amino]-4-methoxycarbonylmethyl-piperidine-1-carboxylic acid tert-butyl ester;
6-Cyclopropylmethoxy-5-trifluoromethoxy-pyridine-2-carboxylic acid (3-carbamoylmethyl-oxetan-3-yl)-amide;
6-Chloro-5-cyclopropylmethoxy-pyridine-2-carboxylic acid (3-carbamoylmethyl-oxetan-3-yl)-amide;
6-Cyclopropylmethoxy-5-(3,3-difluoro-azetidin-1-yl)-pyridine-2-carboxylic acid (2-carbamoyl-1,1-dimethyl-ethyl)-amide;
5-Cyclopropyl-6-(2,2,3,3,3-pentafluoro-propoxy)-pyridine-2-carboxylic acid (3-carbamoylmethyl-oxetan-3-yl)-amide;
(3-{[6-Cyclopropylmethoxy-5-(3,3-difluoro-azetidin-1-yl)-pyridine-2-carbonyl]-amino}-5-oxo-pyrrolidin-3-yl)-acetic acid methyl ester;

(3-{[6-Cyclopropylmethoxy-5-(3,3-difluoro-azetidin-1-yl)-pyridine-2-carbonyl]-amino}-1,1-dioxo-1λ6-thietan-3-yl)-acetic acid ethyl ester;
(4-{[6-Cyclopropylmethoxy-5-(3,3-difluoro-azetidin-1-yl)-pyridine-2-carbonyl]-amino}-tetrahydro-pyran-4-yl)-acetic acid methyl ester;
6-Cyclopropylmethoxy-5-(3,3-difluoro-azetidin-1-yl)-pyridine-2-carboxylic acid [2-carbamoyl-1-(tetrahydro-pyran-4-yl)-ethyl]-amide;
6-Cyclopropylmethoxy-5-(3,3-difluoro-azetidin-1-yl)-pyridine-2-carboxylic acid (3-carbamoylmethyl-5-oxo-pyrrolidin-3-yl)-amide;
6-Cyclopropylmethoxy-5-(3,3-difluoro-azetidin-1-yl)-pyridine-2-carboxylic acid (1-carbamoylmethyl-2,2,2-trifluoro-ethyl)-amide;
(3-{[6-Cyclopropylmethoxy-5-(3,3-difluoro-azetidin-1-yl)-pyridine-2-carbonyl]-amino}-1,1-dioxo-1λ6-thietan-3-yl)-acetic acid;
(4-{[6-Cyclopropylmethoxy-5-(3,3-difluoro-azetidin-1-yl)-pyridine-2-carbonyl]-amino}-tetrahydro-pyran-4-yl)-acetic acid;
(−)-6-Cyclopropylmethoxy-5-(3,3-difluoro-azetidin-1-yl)-pyridine-2-carboxylic acid [2-carbamoyl-1-(tetrahydro-pyran-4-yl)-ethyl]-amide;
(+)-6-Cyclopropylmethoxy-5-(3,3-difluoro-azetidin-1-yl)-pyridine-2-carboxylic acid [2-carbamoyl-1-(tetrahydro-pyran-4-yl)-ethyl]-amide;
6-Cyclopropylmethoxy-5-(3,3-difluoro-azetidin-1-yl)-pyridine-2-carboxylic acid (4-carbamoylmethyl-tetrahydro-pyran-4-yl)-amide;
6-Cyclopropylmethoxy-5-(3,3-difluoro-azetidin-1-yl)-pyridine-2-carboxylic acid (3-carbamoylmethyl-1,1-dioxo-1λ6-thietan-3-yl)-amide; and
6-Cyclopropylmethoxy-5-(3,3-difluoro-azetidin-1-yl)-pyridine-2-carboxylic acid (4-carbamoylmethyl-tetrahydro-thiopyran-4-yl)-amide.

The invention further relates in particular to a compound of formula (I) selected from:
6-Cyclopropylmethoxy-5-(3,3-difluoro-azetidin-1-yl)-pyridine-2-carboxylic acid (1-carbamoylmethyl-cyclobutyl)-amide;
6-Cyclopropylmethoxy-5-(3,3-difluoro-azetidin-1-yl)-pyridine-2-carboxylic acid (3-carbamoylmethyl-thietan-3-yl)-amide;
6-Cyclopropylmethoxy-5-(3,3-difluoro-azetidin-1-yl)-pyridine-2-carboxylic acid (3-carbamoylmethyl-azetidin-3-yl)-amide;
6-Cyclopropylmethoxy-5-(3,3-difluoro-azetidin-1-yl)-pyridine-2-carboxylic acid (1-carbamoylmethyl-3,3-difluoro-cyclobutyl)-amide;
6-Cyclopropylmethoxy-5-(3,3-difluoro-azetidin-1-yl)-pyridine-2-carboxylic acid (6-carbamoylmethyl-2-oxa-Spiro[3.3]hept-6-yl)-amide;
6-Cyclopropylmethoxy-5-(3,3-difluoro-azetidin-1-yl)-pyridine-2-carboxylic acid (3-carbamoylmethyl-tetrahydro-furan-3-yl)-amide;
6-Cyclopropylmethoxy-5-(3,3-difluoro-azetidin-1-yl)-pyridine-2-carboxylic acid (3-carbamoylmethyl-pyrrolidin-3-yl)-amide;
6-Cyclopropylmethoxy-5-(3,3-difluoro-azetidin-1-yl)-pyridine-2-carboxylic acid (4-carbamoylmethyl-1,1-dioxo-1λ6-isothiazolidin-4-yl)-amide;
6-Cyclopropylmethoxy-5-(3,3-difluoro-azetidin-1-yl)-pyridine-2-carboxylic acid (3-carbamoylmethyl-1,1-dioxo-tetrahydro-1λ6-thiophen-3-yl)-amide;
6-Cyclopropylmethoxy-5-(3,3-difluoro-azetidin-1-yl)-pyridine-2-carboxylic acid (3-carbamoylmethyl-tetrahydro-thiophen-3-yl)-amide;
6-Cyclopropylmethoxy-5-(3,3-difluoro-azetidin-1-yl)-pyridine-2-carboxylic acid (4-carbamoylmethyl-piperidin-4-yl)-amide;
6-Cyclopropylmethoxy-5-(3,3-difluoro-azetidin-1-yl)-pyridine-2-carboxylic acid (4-carbamoylmethyl-2-oxo-piperidin-4-yl)-amide;
6-Cyclopropylmethoxy-5-(3,3-difluoro-azetidin-1-yl)-pyridine-2-carboxylic acid (5-carbamoylmethyl-2-oxo-[1,3]oxazinan-5-yl)-amide;
6-Cyclopropylmethoxy-5-(3,3-difluoro-azetidin-1-yl)-pyridine-2-carboxylic acid (4-carbamoylmethyl-1,1-dioxo-hexahydro-1λ6-thiopyran-4-yl)-amide;
6-Cyclopropylmethoxy-5-(3,3-difluoro-azetidin-1-yl)-pyridine-2-carboxylic acid (4-carbamoylmethyl-1,1-dioxo-1λ6-[1,2]thiazinan-4-yl)-amide;
6-Cyclopropylmethoxy-5-(3,3-difluoro-azetidin-1-yl)-pyridine-2-carboxylic acid (3-carbamoylmethyl-6-oxo-piperidin-3-yl)-amide;
6-Cyclopropylmethoxy-5-(3,3-difluoro-azetidin-1-yl)-pyridine-2-carboxylic acid (5-carbamoylmethyl-2-oxo-hexahydro-pyrimidin-5-yl)-amide;
6-Cyclopropylmethoxy-5-(3,3-difluoro-azetidin-1-yl)-pyridine-2-carboxylic acid (3-carbamoylmethyl-1,1-dioxo-hexahydro-1λ6-thiopyran-3-yl)-amide;
6-Cyclopropylmethoxy-5-(3,3-difluoro-azetidin-1-yl)-pyridine-2-carboxylic acid (5-carbamoylmethyl-2-oxo-[1,3]dioxan-5-yl)-amide;
6-Cyclopropylmethoxy-5-(3,3-difluoro-azetidin-1-yl)-pyridine-2-carboxylic acid (3-carbamoylmethyl-tetrahydro-pyran-3-yl)-amide;
6-Cyclopropylmethoxy-5-(3,3-difluoro-azetidin-1-yl)-pyridine-2-carboxylic acid (3-carbamoylmethyl-piperidin-3-yl)-amide;
6-Cyclopropylmethoxy-5-(3,3-difluoro-azetidin-1-yl)-pyridine-2-carboxylic acid (3-carbamoylmethyl-tetrahydro-thiopyran-3-yl)-amide; and
6-Cyclopropylmethoxy-5-(3,3-difluoro-azetidin-1-yl)-pyridine-2-carboxylic acid (5-carbamoylmethyl-1,1-dioxo-1λ6-[1,2]thiazinan-5-yl)-amide.

The invention further relates in particular to a compound of formula (I) selected from:
N-[4-(2-Amino-2-oxoethyl)-1,1-dioxothian-4-yl]-6-(cyclopropylmethoxy)-5-(3,3-difluoroazetidin-1-yl)pyridine-2-carboxamide;
N-[3-Amino-3-oxo-1-(oxolan-3-yl)propyl]-5-cyclopropyl-6-(cyclopropylmethoxy)pyridine-2-carboxamide;
N-[3-(2-Amino-2-oxoethyl)azetidin-3-yl]-6-(cyclopropylmethoxy)-5-(3,3-difluoroazetidin-1-yl)pyridine-2-carboxamide;
N-[4-(2-Amino-2-oxoethyl)piperidin-4-yl]-5-cyclopropyl-6-[(4-fluorophenyl)methyl]pyridine-2-carboxamide; hydrochloride;
N-[3-Amino-3-oxo-1-(oxolan-3-yl)propyl]-6-(cyclopropylmethoxy)-5-(3,3-difluoroazetidin-1-yl)pyridine-2-carboxamide;
Methyl 2-[1-[[6-(cyclopropylmethoxy)-5-(3,3-difluoroazetidin-1-yl)pyridine-2-carbonyl]amino]cyclobutyl]acetate;
2-[1-[[6-(Cyclopropylmethoxy)-5-(3,3-difluoroazetidin-1-yl)pyridine-2-carbonyl]amino]cyclobutyl]acetic acid;
N-[1-(2-Amino-2-oxoethyl)cyclobutyl]-6-(cyclopropylmethoxy)-5-(3,3-difluoroazetidin-1-yl)pyridine-2-carboxamide;

Ethyl 1-[[[6-(cyclopropylmethoxy)-5-(3,3-difluoroazetidin-1-yl)pyridine-2-carbonyl]amino]methyl]cyclopropane-1-carboxylate;

N-[1-Acetyl-4-(2-amino-2-oxoethyl)piperidin-4-yl]-5-cyclopropyl-6-[(4-fluorophenyl)methyl]pyridine-2-carboxamide;

N-[1-Acetyl-3-(2-amino-2-oxoethyl)azetidin-3-yl]-6-(cyclopropylmethoxy)-5-(3,3-difluoroazetidin-1-yl)pyridine-2-carboxamide;

Benzyl 3-(2-amino-2-oxoethyl)-3-[[5-cyclopropyl-6-[(4-fluorophenyl)methyl]pyridine-2-carbonyl]amino]azetidine-1-carboxylate;

N-[3-(2-Amino-2-oxoethyl)-1,1-dioxothietan-3-yl]-5-cyclopropyl-6-(2-methylpropylsulfanyl)pyridine-2-carboxamide;

N-[3-(2-Amino-2-oxoethyl)-1,1-dioxothietan-3-yl]-5-cyclopropyl-6-[(4-fluorophenyl)methyl]pyridine-2-carboxamide;

N-[3-(2-Amino-2-oxoethyl)-1,1-dioxothietan-3-yl]-5-cyclopropyl-6-(cyclopropylmethoxy)pyridine-2-carboxamide;

N-[3-(2-Amino-2-oxoethyl)-1,1-dioxothietan-3-yl]-6-(oxan-4-ylmethoxy)-5-(trifluoromethyl)pyridine-2-carboxamide;

N-[3-(2-Amino-2-oxoethyl)-1,1-dioxothietan-3-yl]-6-(3-chloro-4-fluorophenyl)pyridine-2-carboxamide;

N-[3-(2-Amino-2-oxoethyl)-1,1-dioxothietan-3-yl]-5-cyclopropyl-6-(oxolan-2-ylmethoxy)pyridine-2-carboxamide;

N-[3-(2-Amino-2-oxoethyl)azetidin-3-yl]-5-cyclopropyl-6-[(4-fluorophenyl)methyl]pyridine-2-carboxamide;

N-[3-(2-Amino-2-oxoethyl)oxolan-3-yl]-6-(cyclopropylmethoxy)-5-(3,3-difluoroazetidin-1-yl)pyridine-2-carboxamide;

Benzyl 3-(2-amino-2-oxoethyl)-3-[[6-(cyclopropylmethoxy)-5-(3,3-difluoroazetidin-1-yl)pyridine-2-carbonyl]amino]pyrrolidine-1-carboxylate;

N-[3-(2-Amino-2-oxoethyl)pyrrolidin-3-yl]-6-(cyclopropylmethoxy)-5-(3,3-difluoroazetidin-1-yl)pyridine-2-carboxamide;

N-[4-(2-Amino-2-oxoethyl)piperidin-4-yl]-6-(cyclopropylmethoxy)-5-(3,3-difluoroazetidin-1-yl)pyridine-2-carboxamide;

N-[4-(2-Amino-2-oxoethyl)piperidin-4-yl]-5-cyclopropyl-6-(cyclopropylmethoxy)pyridine-2-carboxamide;

N-[3-(2-Amino-2-oxoethyl)oxolan-3-yl]-5-cyclopropyl-6-[(4-fluorophenyl)methyl]pyridine-2-carboxamide;

N-[3-(2-Amino-2-oxoethyl)oxolan-3-yl]-5-cyclopropyl-6-(cyclopropylmethoxy)pyridine-2-carboxamide;

N-[3-(2-Amino-2-oxoethyl)oxetan-3-yl]-6-(cyclopropylmethoxy)-5-(1-fluorocyclobutyl)pyridine-2-carboxamide;

N-[3-(2-Amino-2-oxoethyl)oxetan-3-yl]-6-(cyclopropylmethoxy)-5-(1-hydroxycyclobutyl)pyridine-2-carboxamide;

N-[3-(2-Amino-2-oxoethyl)thietan-3-yl]-6-(cyclopropylmethoxy)-5-(3,3-difluoroazetidin-1-yl)pyridine-2-carboxamide;

N-[3-(2-Amino-2-oxoethyl)-1,1-dioxothietan-3-yl]-6-(cyclopropylmethoxy)-5-(1-hydroxycyclobutyl)pyridine-2-carboxamide;

N-[3-(2-Amino-2-oxoethyl)oxetan-3-yl]-6-(cyclopropylmethoxy)-5-(3-fluorooxetan-3-yl)pyridine-2-carboxamide;

N-[3-(2-Amino-2-oxoethyl)oxetan-3-yl]-6-(cyclopropylmethoxy)-5-(3-hydroxyoxetan-3-yl)pyridine-2-carboxamide;

N-[3-(2-Amino-2-oxoethyl)thietan-3-yl]-6-(cyclopropylmethoxy)-5-(1-hydroxycyclobutyl)pyridine-2-carboxamide;

N-[3-(2-Amino-2-oxoethyl)thietan-3-yl]-5-cyclopropyl-6-(cyclopropylmethoxy)pyridine-2-carboxamide;

N-[3-(2-Amino-2-oxoethyl)thietan-3-yl]-6-(cyclopropylmethoxy)-5-(trifluoromethyl)pyridine-2-carboxamide; and N-[3-(2-Amino-2-oxoethyl)thietan-3-yl]-6-(cyclopropylmethoxy)-5-(3-fluorooxetan-3-yl)pyridine-2-carboxamide.

The invention relates in particular to a compound of formula (I) selected from:

3-{[6-Cyclopropylmethoxy-5-(3,3-difluoro-azetidin-1-yl)-pyridine-2-carbonyl]-amino}-3-phenyl-propionic acid ethyl ester;

(+)-cis-5-Cyclopropyl-6-cyclopropylmethoxy-pyridine-2-carboxylic acid (2-carbamoyl-cyclohexyl)-amide;

(+)-5-Cyclopropyl-6-cyclopropylmethoxy-pyridine-2-carboxylic acid (2-carbamoyl-1-cyclohexyl-ethyl)-amide;

5-Cyclopropyl-6-cyclopropylmethoxy-pyridine-2-carboxylic acid (3-carbamoylmethyl-oxetan-3-yl)-amide;

6-Cyclopropylmethoxy-5-(3,3-difluoro-azetidin-1-yl)-pyridine-2-carboxylic acid (3-carbamoylmethyl-oxetan-3-yl)-amide;

(+)-5-Cyclopropyl-6-cyclopropylmethoxy-pyridine-2-carboxylic acid (2-carbamoyl-1-cyclopropyl-ethyl)-amide;

5-Cyclopropyl-6-cyclopropylmethoxy-pyridine-2-carboxylic acid [2-carbamoyl-1-(tetrahydro-pyran-4-yl)-ethyl]-amide;

6-Cyclopropylmethoxy-5-(3,3-difluoro-azetidin-1-yl)-pyridine-2-carboxylic acid (2-carbamoyl-1,1-dimethyl-ethyl)-amide;

5-Cyclopropyl-6-(2,2,3,3,3-pentafluoro-propoxy)-pyridine-2-carboxylic acid (3-carbamoylmethyl-oxetan-3-yl)-amide;

6-Cyclopropylmethoxy-5-(3,3-difluoro-azetidin-1-yl)-pyridine-2-carboxylic acid (1-carbamoylmethyl-2,2,2-trifluoro-ethyl)-amide; and 6-Cyclopropylmethoxy-5-(3,3-difluoro-azetidin-1-yl)-pyridine-2-carboxylic acid (3-carbamoylmethyl-1,1-dioxo-1λ6-thietan-3-yl)-amide.

The invention further relates in particular to a compound of formula (I) selected from:

N-[4-(2-Amino-2-oxoethyl)piperidin-4-yl]-5-cyclopropyl-6-[(4-fluorophenyl)methyl]pyridine-2-carboxamide; hydrochloride;

N-[1-(2-Amino-2-oxoethyl)cyclobutyl]-6-(cyclopropylmethoxy)-5-(3,3-difluoroazetidin-1-yl)pyridine-2-carboxamide;

N-[3-(2-Amino-2-oxoethyl)-1,1-dioxothietan-3-yl]-5-cyclopropyl-6-(cyclopropylmethoxy)pyridine-2-carboxamide;

N-[3-(2-Amino-2-oxoethyl)-1,1-dioxothietan-3-yl]-5-cyclopropyl-6-(oxolan-2-ylmethoxy)pyridine-2-carboxamide;

N-[3-(2-Amino-2-oxoethyl)oxolan-3-yl]-6-(cyclopropylmethoxy)-5-(3,3-difluoroazetidin-1-yl)pyridine-2-carboxamide;

N-[3-(2-Amino-2-oxoethyl)oxetan-3-yl]-6-(cyclopropylmethoxy)-5-(1-fluorocyclobutyl)pyridine-2-carboxamide;

N-[3-(2-Amino-2-oxoethyl)-1,1-dioxothietan-3-yl]-6-(cyclopropylmethoxy)-5-(1-hydroxycyclobutyl)pyridine-2-carboxamide;

N-[3-(2-Amino-2-oxoethyl)thietan-3-yl]-6-(cyclopropyl-methoxy)-5-(trifluoromethyl)pyridine-2-carboxamide; and N-[3-(2-Amino-2-oxoethyl)thietan-3-yl]-6-(cyclopropyl-methoxy)-5-(3-fluorooxetan-3-yl)pyridine-2-carboxamide.

6-Cyclopropylmethoxy-5-(3,3-difluoro-azetidin-1-yl)-pyridine-2-carboxylic acid (3-carbamoylmethyl-oxetan-3-yl)-amide is a particular object of the present invention.

The synthesis of the compound of formula (I) can, for example, be accomplished according to the following schemes.

Unless otherwise specified, $R^1$ to $R^3$ have in the following schemes the meaning as defined above.

Following the procedure according to scheme 1, compound AA (R'=H, methyl, ethyl, isopropyl, tert. butyl or another suitable protecting group described for example in T. W. Greene et al., Protective Groups in Organic Chemistry, John Wiley and Sons Inc. New York 1999, $3^{rd}$ edition) can be used as starting material. AA is either commercially available, described in the literature or can be synthesized by a person skilled in the art.

Compound AE can be further elaborated to compounds II by saponification (for compounds AE with R'≠H) by methods well known to the ones skilled in the art—using e.g. aqueous LiOH, NaOH or KOH in tetrahydrofuran/ethanol or another suitable solvent at temperatures between 0° C. and the reflux temperature of the solvent employed.

Compounds of formula I can be prepared from compounds of formula II by amide coupling methods known in the art as already described.

If one of the starting materials, compounds of formulae AA, AD or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae AA to AE, AC, II or III contain chiral centers, picolines of formula I can be

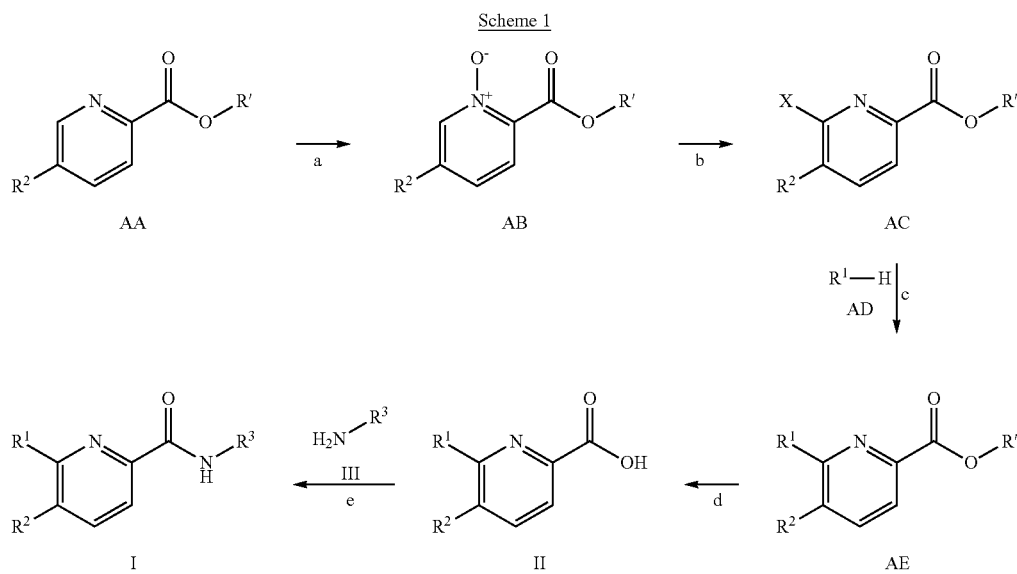

Scheme 1

Compound AB can be prepared from AA by oxidation with a suitable oxidizing reagent under conditions known to a person skilled in the art (step a), e.g. by treatment with 3-chloro perbenzoic acid in dichloromethane at ambient temperature.

Conversion of compound AB to 6-chloro or 6-bromo-picoline AC (X=Cl, Br) can be achieved e.g. by treatment with phosphoryl trichloride or tribromide either without an additional solvent or in a suitable solvent such as chloroform at temperatures between 20° C. and the boiling point of the solvent, or by using other conditions known in the literature (step b).

6-Chloro- or bromo-picoline AC (X=Cl, Br) can be transformed to compound AE by reaction with a suitably substituted primary or secondary alcohol AD in the presence of a base, for example sodium hydride, with or without an inert solvent, for example dimethylformamide, at temperatures ranging from room temperature to the reflux temperature of the solvent, particularly at room temperature (step c).

obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 2, compound BA (R'=H, methyl, ethyl, isopropyl, tert. butyl or another suitable protecting group described for example in T. W. Greene et al., Protective Groups in Organic Chemistry, John Wiley and Sons Inc. New York 1999, $3^{rd}$ edition) can be used as starting material. BA is either commercially available (e.g. for R'=methyl:5-bromo-6-chloro-pyridine-2-carboxylic acid methyl ester CAN 1214353-79-3), described in the literature or can be synthesized by a person skilled in the art.

Scheme 2

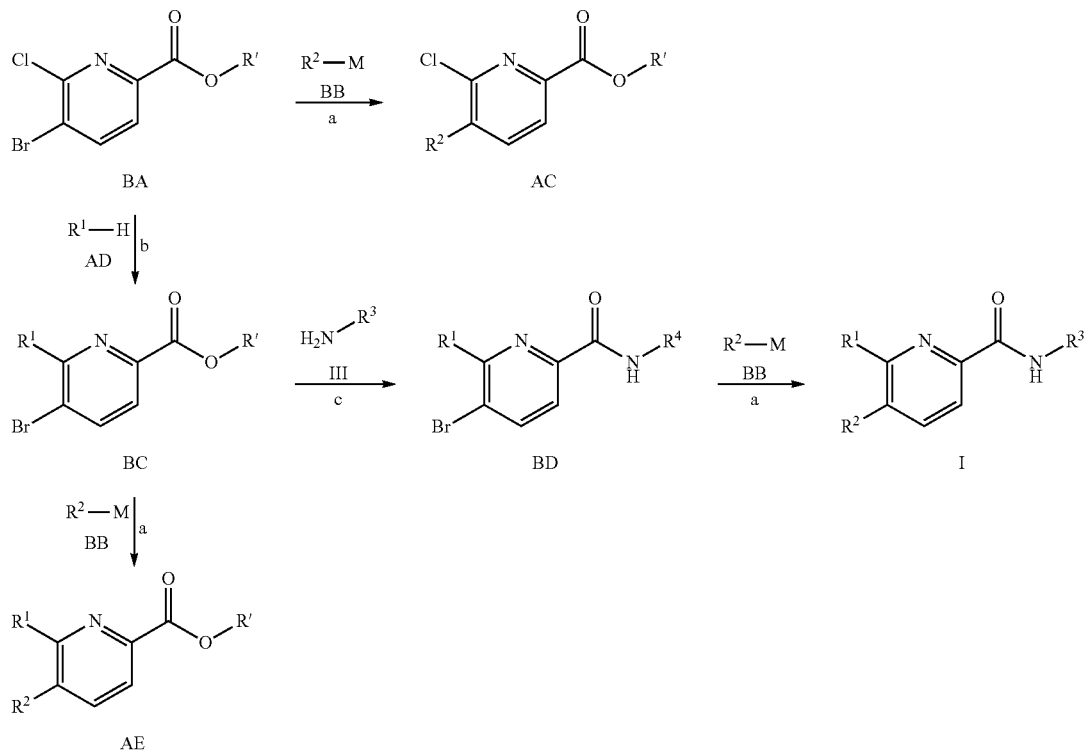

Compound AC can be prepared from BA by coupling a suitably substituted cycloalkyl or cycloalkenyl metal species of formula BB (M is e.g. a trifluoroborate $[BF_3]^-K^+$, a boronic acid $B(OH)_2$ or a boronic acid pinacol ester) (step a), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1′-bis(diphenylphosphino)ferrocene) complexes and a base such as triethylamine, sodium carbonate or potassium phosphate in an inert solvent such as dimethylformamide, toluene, tetrahydrofuran, acetonitrile or dimethoxyethane. Optionally, compound BB can also be an amine which is coupled to BA by methods well known to a person skilled in the art, e.g. using a palladium catalyst such as tris(dibenzylideneacetone)dipalladium/dimethylbisdiphenyl-phosphinoxanthene and a base such as cesium carbonate in a solvent such as 1,4-dioxane, preferentially at the boiling point of the solvent. Optionally, alkenyl containing $R^2$ residues can be transformed to the corresponding alkyl congeners AC using conditions described in the literature such as e.g. a hydrogenation reaction using hydrogen gas in the presence of a catalyst such as palladium on carbon in a solvent such as ethanol or ethyl acetate particularly at ambient temperature.

Compound AC can be further elaborated to compound I by: i) reaction with compound AD to form compound AE as described in step c of scheme 1; ii) saponification as described in step d of scheme 1; and iii) amide bond formation as described in step e of scheme 1.

Furthermore, compound BA can be converted into compound BC by treatment with compound AD as described in step c of scheme 1 (step b).

Subsequent transformation of compound BC into compound AE can be achieved as discussed for the conversion of BA into AC (step a).

Compound AE can be further elaborated to compound I by: i) saponification as described in step d of scheme 1; ii) amide bond formation as described in step e of scheme 1.

Alternatively, compound BC (R′=methyl, ethyl, isopropyl, tert. butyl or another suitable protecting group described for example in T. W. Greene et al., Protective Groups in Organic Chemistry, John Wiley and Sons Inc. New York 1999, $3^{rd}$ edition) can be: i) converted into its acid congener BC (R′=H) as described in step d of scheme 1; ii) transformed into the corresponding amide BD by treatment with amine III as described in step e of scheme 1; and iii) reacted with BB as described in step a to arrive at compound I.

In addition, compounds of formula I with $R^1$ being an alkylsulfonyl residue can be synthesized using the following reaction sequence: i) Reaction of compound BA (e.g. for R′=H: 5-bromo-6-chloro-pyridine-2-carboxylic acid; CAN 959958-25-9) with a thiol AD to yield thioether BC, e.g. in the presence of a base such as cesium carbonate in a solvent such as DMSO, preferentially at temperatures between 100 and 150° C.; ii) conversion of thioethers BC($R^1$=S-Alkyl) to its corresponding sulfonyl congeners BC($R^1$=$S(O)_2$-Alkyl), e.g. by using an oxidizing reagent such as 3-chlorobenzoperoxoic acid in a solvent such as dichloromethane, preferentially at ambient temperature; iii) transformation of sulfonyl derivatives BC into compound AE as discussed for the conversion of BA into AC (step a); and iv) further elaboration to sulfonyl derivative I via saponification as described in step d of scheme 1 followed by an amide bond formation as described in step e of scheme 1. Optionally, the row order of the reaction sequence can be interchanged. Compounds of formula I with $R^1$ being an alkylsulfinyl residue can be synthesized in analogy to their alkylsulfonyl congeners but omitting the conversion of thioethers BC(R¹=S-Alkyl) to the corresponding sulfonyl congeners BC(R¹=S(O)₂-Alkyl).

Furthermore, compound I can also be synthesized applying the following reaction sequence: i) saponification of compound BA (R'=methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) to its acid congener BC (R'=H) as described in step d of scheme 1; ii) conversion to the corresponding amide by treatment with amine III as described in step e of scheme 1; iii) reaction with compound BB as described in step a; and iv) reaction with compound AD as described in step b. Optionally step iii) and step iv) can be interchanged.

If one of the starting materials, compounds of formulae BA, BB, AD or III contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae BA, BB or AD contain chiral centers, picolines of formula AC and AE can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 3, compound BC (R'=H, methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be used as starting material. BC is either commercially available, described in the literature, can be synthesized by methods described in scheme 3 or by other methods known to a person skilled in the art.

Scheme 3

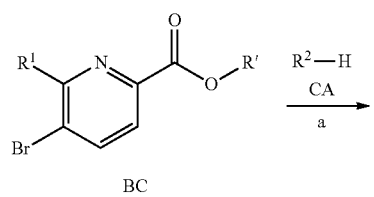

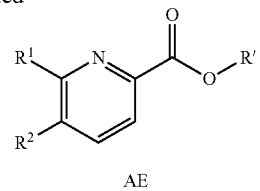

Compound AE (with R² being in this case haloazetidinyl or pyrrolidinyl) can be prepared from BC by coupling a suitably substituted amine CA applying methods well known in the art (step a), for example using a palladium promoted amination with palladium(II)acetate/2-(dicyclohexylphosphino) biphenyl in the presence of a base such as potassium carbonate in dioxane under reflux conditions or by using tris(dibenzylideneacetone)dipalladium/rac-BINAP (2,2'-bis(diphenylphosphino)-1,1'-binaphthyl) in the presence of a base such as cesium carbonate in toluene at 100° C.

Compound AE can be further elaborated to compound I by: i) saponification as described in step d of scheme 1; ii) amide bond formation as described in step e of scheme 1.

If one of the starting materials, compounds of formulae BC or CA, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae BC or CA, contain chiral centers, picolines of formula AE can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbens or a chiral eluent.

Following the procedure according to scheme 4, compound EA (X=Cl, Br, I, trifluoromethanesulfonate; R'=H, methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be used as starting material. EA is either commercially available, described in the literature or can be synthesized by a person skilled in the art.

Scheme 4

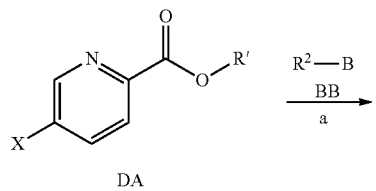

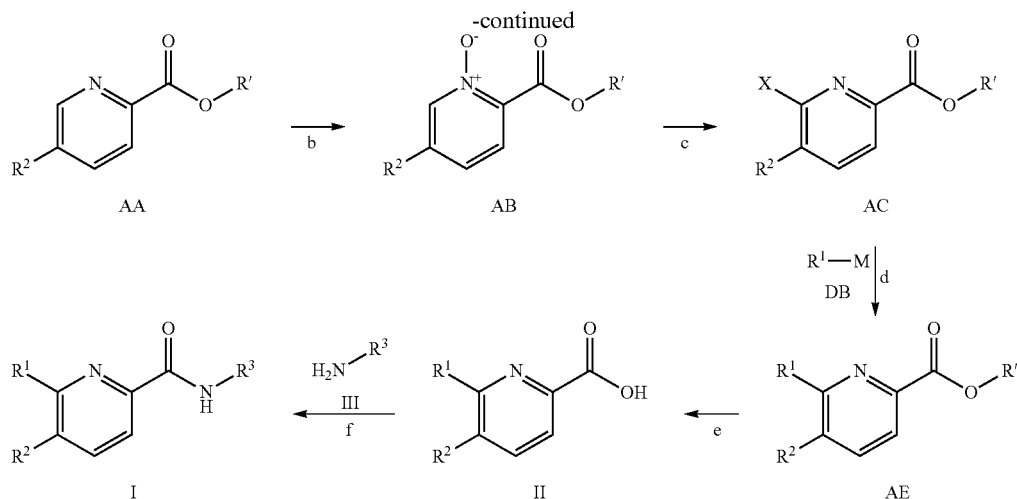

Compound AA can be prepared from DA by coupling a suitably substituted aryl, heteroaryl or alkenyl metal species of formula BB (M is e.g. a trifluoroborate [$BF_3$]—$K^+$, a boronic acid $B(OH)_2$ or a boronic acid pinacol ester) (step a), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenyl-phosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^2$ residues can be transformed to the corresponding alkyl congeners AA using conditions described in the literature such as e.g. a hydrogenation reaction using hydrogen gas in the presence of a catalyst such as palladium on carbon in a solvent such as ethanol or ethyl acetate particularly at ambient temperature.

Compound AB can be prepared from AA by oxidation with a suitable oxidizing reagent as described in step a of scheme 1 (step b).

Conversion of compound AB to 6-chloro- or 6-bromo-picoline AC (X=Cl, Br) can be achieved as described in step b of scheme 1 (step c).

Compound AE can be prepared from AC by coupling a suitably substituted cycloalkyl or cycloalkenyl metal species of formula DB (M is e.g. a trifluoroborate [$BF_3$]$K^+$, a boronic acid $B(OH)_2$ or a boronic acid pinacol ester) (step d), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile or dimethoxyethane. Optionally, alkenyl containing $R^1$ residues can be transformed to the corresponding alkyl congeners AE using conditions described in the literature such as e.g. a hydrogenation reaction using hydrogen gas in the presence of a catalyst such as palladium on carbon in a solvent such as ethanol or ethyl acetate particularly at ambient temperature.

Compound AE can be further elaborated to compound I by: i) saponification as described in step d of scheme 1 (step e); ii) amide bond formation as described in step e of scheme 1 (step f).

If one of the starting materials, compounds of formulae DA, BB, DB or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae DA, BB, AA, AB, AC, DB, AE, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 6, compound EA can be used as starting material. EA is either commercially available, described in the literature or can be synthesized by a person skilled in the art.

Scheme 5

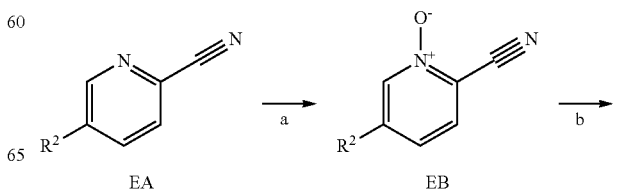

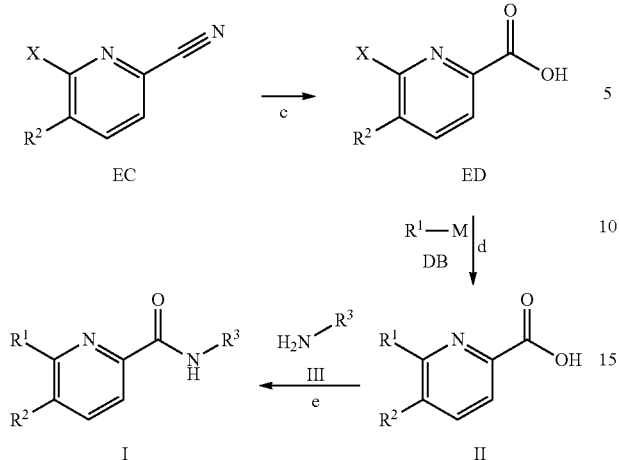

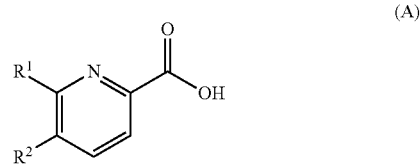

Compound EB can be prepared from EA by oxidation with a suitable oxidizing reagent under conditions known to a person skilled in the art (step a), e.g. by treatment with 3-chloro perbenzoic acid in dichloromethane at ambient temperature.

Conversion of compound EB to 6-chloro or 6-bromo compound EC (X=Cl, Br) can be achieved e.g. by treatment with phosphoryl trichloride or tribromide either without an additional solvent or in a suitable solvent such as chloroform at temperatures between 20° C. and the boiling point of the solvent or by using other conditions known in the literature (step b).

Hydrolysis of compound EC leads to picoline ED and can be performed under acidic or basic conditions known to a person skilled in the art, e.g. by treatment with an aqueous solution of sodium hydroxide at 100° C. (step c).

Compound II can be prepared from ED by coupling a suitably substituted cycloalkyl or cycloalkenyl metal species of formula DB (M is e.g. a trifluoroborate [$BF_3$]—$K^+$, a boronic acid $B(OH)_2$ or a boronic acid pinacol ester) (step d) as described in step d of scheme 6. Optionally, alkenyl containing $R^1$ residues can be transformed to the corresponding alkyl congeners II using conditions described in the literature such as e.g. a hydrogenation reaction using hydrogen gas in the presence of a catalyst such as palladium on carbon in a solvent such as ethanol or ethyl acetate particularly at ambient temperature. In cases where the acid group of compound ED is not compatible with the conditions applied to introduce the $R^1$ residue, suitable protecting groups such as ester protecting groups e.g. a methyl ester can be introduced prior to step d and removed at a later point of the synthesis. Protecting group introduction and removal can be carried out by suitable methods known in the art (for more details see T. W. Greene et al., Protective Groups in Organic Chemistry, John Wiley and Sons Inc. New York 1999, 3$^{rd}$ edition).

Further conversion of compound II to compound I can be done by applying amide bond formation conditions as depicted in step e of scheme 1 (step e).

If one of the starting materials, compounds of formulae EA, DB or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae EA to ED, DB, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention also relates to a process for the preparation of formula (I), comprising the reaction of a compound of formula (A)

(A)

$R^1$ \ / N \ / OH
  \  /      \  /
   \/        \/
   /\        /\
  /  \      /  \
$R^2$ in the presence of $R^3$—$NH_2$, an amide coupling agent and a base;
wherein $R^1$ to $R^3$ are as defined in any one of claims 1 to 10.

If desired, the compound of formula (I) can be converted into a pharmaceutically acceptable salt thereof.

Compounds of formula $R^3$—$NH_2$ or (A) may contain functional groups that would interfere with the coupling procedures described for the amide coupling step (A) to (I). In this case it is understood that $R^3$—$NH_2$ or (A) need to be suitably protected by methods known in the art before conducting the amide coupling procedure and compounds need to be deprotected after the coupling step by methods known in the art to deliver compounds of formula (I).

Amide coupling agents for the reaction of compounds of formula (A) with amines of formula $R^3$—$NH_2$ are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), or O-benzotriazole-N,N,N',N'-tetramethyl-uronium-hexafluoro-phosphate (HBTU). Particular coupling agents are TBTU and HATU. Suitable bases include triethylamine, N-methylmorpholine and particularly diisopropylethylamine. Alternative methods known in the art may commence by preparing the acid chloride from (A) and coupling with an amine of formula $R^3$—$NH_2$ in the presence of a suitable base.

The invention also relates in particular to:

The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

A compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention further particularly relates to a compound of formula (I) for the treatment or prophylaxis of diabetic retinopathy, retinal vein occlusion or uveitis.

The invention is further directed to a compound of formula (I), when manufactured according to a process according to the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration.

Parenteral infusions include intramuscular, intravenous, intraarterial, intraperitoneal, or subcutaneous administration. The compounds of the invention may be administered in particular by intravitreal administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

BEP=2-bromo-1-ethylpyridinium tetrafluoroborate; CAN=CAS Registry Number; CDI=N,N'-carbonyldiimidazole; DCM=dichloromethane; DIEA=N-ethyl-N-isopropyl-propan-2-amine; DMF=dimethylformamide; DMSO=dimethyl-sulfoxide; dppf=1,1'-bis(diphenylphosphino)ferrocene; EI=electron ionization; ESI=electrospray; HATU=2-(3H-[1,2,3]triazolo[4,5-b]pyridin-3-yl)-1,1,3,3-tetramethylisouronium hexafluorophosphate(V); HBTU=O-benzotriazole-N,N,N',N'-tetramethyl-uronium-hexafluoro-phosphate; HPLC=LC=high performance liquid chromatography; m-CPBA=meta-chloroperoxybenzoic acid; MS=mass spectrometry; NMR=nuclear magnetic resonance; TBTU=O-(benzotriazol-1-yl)-N,N,N',N'-tetramethyl-uronium-tetrafluoroborate; TBME=methyl tert-butylether, TEMPO=(2,2,6,6-tetramethylpiperidin-1-yl)oxidanyl; THF=tetrahydrofuran; tlc=thin layer chromatography.

Example 1

{3-[(5-Cyclopropyl-6-cyclopropylmethoxy-pyridine-2-carbonyl)-amino]-oxetan-3-yl}-acetic acid ethyl ester a) 5-Bromo-6-chloro-pyridine-2-carboxylic acid methyl ester

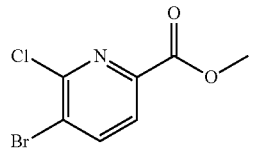

A mixture of 5-bromo-pyridine-2-carboxylic acid methyl ester (CAN 29682-15-3, 50 g, 0.23 mol) and m-CPBA (CAN 937-14-4, 80 g, 0.46 mol) in 400 mL dry methylene chloride was heated to 60° C. for 20 h. After that, the mixture was quenched with saturated sodium sulfite solution and extracted with ethyl acetate (2×200 mL). The organic layer was washed with brine (2×200 mL) and evaporated to dryness. The residue was purified with by column chromatography (silica gel, 300 g, eluting with 15% ethyl acetate in petroleum ether) to obtain a brown oil. The brown oil, 5-bromo-2-(methoxycarbonyl)pyridine 1-oxide (30 g, 0.13 mol) was added into phosphoryl trichloride (CAN 10025-87-3, 80 mL) at 0° C. over 1 h, then the mixture was heated to 95° C. for 1 h. After that the mixture was evaporated to dryness, the residue was dissolved in water (50 mL), extracted with ethyl acetate (3×50 mL) and the organic layer was evaporated to dryness to obtain the product as a white solid (19 g, 59%); MS (EI): m/e=249.9 [MH$^+$].

b) 5-Bromo-6-cyclopropylmethoxy-pyridine-2-carboxylic acid

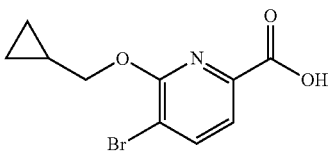 [SMILES: O=C(O)c1ccc(Br)c(OCC2CC2)n1]

Sodium hydride (4.83 g, 0.12 mol) was added into cyclopropanemethanol (CAN 2516-33-8, 30 g) at 0° C. and the mixture was stirred at 0° C. for 1 h. Then to the mixture was added methyl 5-bromo-6-chloro-pyridine-2-carboxylic acid methyl ester (3 g, 12.75 mmol). The obtained solution was heated to 90° C. for 2 h. Then the mixture was evaporated to dryness, the residue was dissolved in 40 mL of water, and adjusted to pH=4 with hydrochloric acid (3 N), and extracted with ethyl acetate (3×30 mL). The combined organic layer was washed with water (2×30 mL) and brine (2×50 mL) then evaporated to dryness to obtain the product as a white solid (2.5 g, 76.7%); MS (EI): m/e=272.0 [MH$^+$].

c) 5-Cyclopropyl-6-cyclopropylmethoxy-pyridine-2-carboxylic acid

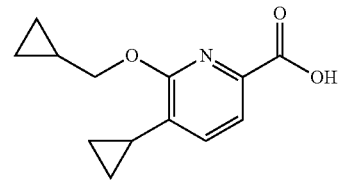 [SMILES: O=C(O)c1ccc(C2CC2)c(OCC2CC2)n1]

A mixture of 5-bromo-6-(cyclopropylmethoxy)-pyridine-2-carboxylic acid (1.5 g, 5.5 mmol), cyclopropylboronic acid (CAN 411235-57-9, 0.57 g, 7 mmol), palladium diacetate (CAN 3375-31-3, 62 mg, 0.28 mmol), tricyclohexylphosphine (CAN 2622-14-2, 154 mg, 0.1 mmol) and potassium phosphate (4.1 g, 19 mmol) in toluene/water (20/1 v/v, 30 mL) was heated to 100° C. overnight. After that the mixture was evaporated to dryness, dissolved in 30 mL of water, extracted with ethyl acetate (30 mL) and the organic layer was dropped. The water layer was adjusted to pH=3 and extracted with ethyl acetate (2×30 mL), this organic layer was washed with water (30 mL) and brine (30 mL), dried over anhydrous sodium sulfate then evaporated to dryness. The residue was purified by column chromatography (silica gel, 10 g, eluting with 15% ethyl acetate in petroleum ether) to obtain the title compound (0.96 g, 75%) as white solid; MS (LC/MS): 234.1 [MH$^+$].

d) {3-[(5-Cyclopropyl-6-cyclopropylmethoxy-pyridine-2-carbonyl)-amino]-oxetan-3-yl}-acetic acid ethyl ester

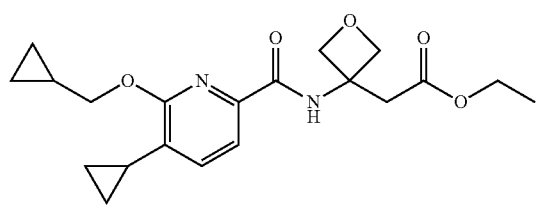 [SMILES: CCOC(=O)CC1(NC(=O)c2ccc(C3CC3)c(OCC3CC3)n2)COC1]

5-Cyclopropyl-6-cyclopropylmethoxy-pyridine-2-carboxylic acid (70 mg, 300 μmol) was dissolved in DMF (3 mL). TBTU (106 mg, 330 μmol), DIEA (257 μl, 1.5 mmol) and 3-amino-3-oxetaneacetic acid ethyl ester (CAN 1207175-54-9, 52.5 mg, 330 μmol) were added and the reaction mixture was stirred at room temperature for 16 hours. Ethyl acetate (3 mL) and 1 N sodium hydroxide solution (2 mL) were added; the mixture was dried by passage through ChemElut® and concentrated in vacuo. The crude material was purified by flash chromatography (silica gel, ethyl acetate/n-heptane gradient) to give the title compound (108 mg, 96%) as white solid; LC-MS (UV peak area, ESI) 96%, 375.1914 [MH⁺].

Example 2 tert-Butyl 3-({[6-(cyclopropylmethoxy)-5-(3,3-difluoroazetidin-1-yl)pyridin-2-yl]carbonyl}amino)-5-methylhexanoate a) 6-Chloro-5-(3,3-difluoro-azetidin-1-yl)-pyridine-2-carboxylic acid methyl ester

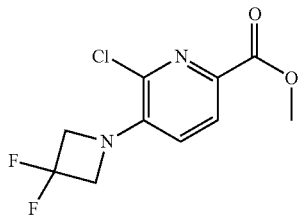 [SMILES: COC(=O)c1ccc(N2CC(F)(F)C2)c(Cl)n1]

Under a nitrogen atmosphere a mixture of methyl 5-bromo-6-chloro-pyridine-2-carboxylic acid methyl ester (Example 1 a), 2 g, 8 mmol), 3,3-difluoroazetidine hydrochloride (CAN 288315-03-7, 1 g, 8 mmol), tris(dibenzylideneacetone)dipalladium (CAN 51364-51-3, 0.16 g, 0.16 mmol), (R)-(+)-2,2'-bis(diphenylphosphino)-1,1'-binaphthyl (CAN 76189-55-4, 0.19 g, 0.32 mmol) and cesium carbonate (3.9 g, 12 mmol) in toluene (50 mL) was stirred at 110° C. overnight. After concentration, the residue was partitioned between water (50 mL) and ethyl acetate (40 mL), the aqueous phase was extracted with ethyl acetate (2×40 mL). The combined organic phase was washed with brine (40 mL), dried over anhydrous sodium sulfate, filtered and concentrated to give a residue. The residue was purified by column chromatography (silica gel, 20 g, 10% ethyl acetate in petroleum ether) to give the target compound (0.44 g, 21%) as light-yellow solid; MS (EI): m/e=263.0 [MH⁺].

b) 6-Cyclopropylmethoxy-5-(3,3-difluoro-azetidin-1-yl)-pyridine-2-carboxylic acid

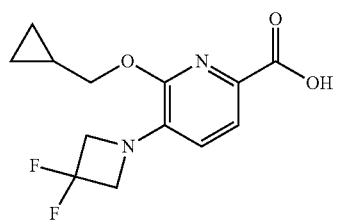 [SMILES: O=C(O)c1ccc(N2CC(F)(F)C2)c(OCC2CC2)n1]

Sodium hydride (0.29 g, 8.4 mmol) was added in portion to a solution of cyclopropylmethanol (CAN 2516-33-8, 0.36 g, 5 mmol) in DMF (3 mL) and the mixture was stirred at room temperature for 2 h. 6-Chloro-5-(3,3-difluoro-azetidin-1-yl)-pyridine-2-carboxylic acid methyl ester (0.44 g, 1.68 mmol) was added to the mixture and the resulting solution was stirred at 110° C. overnight. After concentration, water (20 mL) was added to the residue and the solution was acidified with an aqueous solution of hydrochloride (6 N), then extracted with ethyl acetate (2×20 mL). The combined organic phase was washed with brine (20 mL), dried over anhydrous sodium sulfate, filtered and concentrated to give a residue. The residue was purified by prep-TLC (eluting with 50% ethyl acetate in petroleum ether) to give the target compound (0.07 g, 14%); MS (EI): m/e=285.1 [MH⁺].

c) tert-Butyl 3-({[6-(cyclopropylmethoxy)-5-(3,3-difluoroazetidin-1-yl)pyridin-2-yl]carbonyl}amino)-5-methylhexanoate

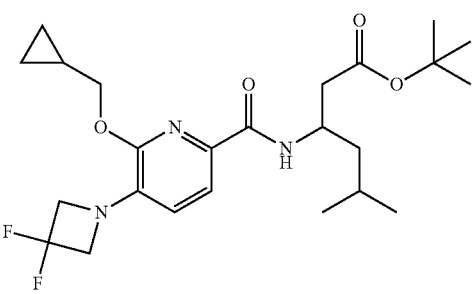 [SMILES: CC(C)CC(CC(=O)OC(C)(C)C)NC(=O)c1ccc(N2CC(F)(F)C2)c(OCC2CC2)n1]

In analogy to the procedure described in Example 1 d), 6-cyclopropylmethoxy-5-(3,3-difluoro-azetidin-1-yl)-pyridine-2-carboxylic acid was reacted with tert-butyl 3-amino-5-methylhexanoate (902146-26-3) in the presence of TBTU and DIEA to obtain the title compound as colorless oil; MS (EI): m/e=468.0 [MH⁺].

Example 3

6-Cyclopropylmethoxy-5-(3,3-difluoro-azetidin-1-yl)-pyridine-2-carboxylic acid (1-methyl-5-oxo-pyrrolidin-3-yl)-amide

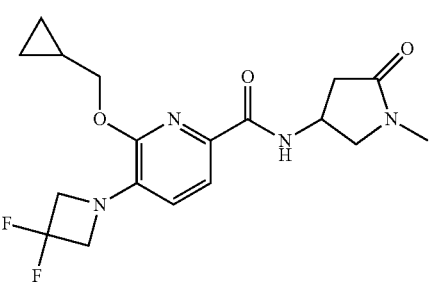 [SMILES: CN1CC(NC(=O)c2ccc(N3CC(F)(F)C3)c(OCC3CC3)n2)CC1=O]

In analogy to the procedure described in Example 1 d), 6-cyclopropylmethoxy-5-(3,3-difluoro-azetidin-1-yl)-pyridine-2-carboxylic acid (Example 2 b)) was reacted with 4-amino-1-methylpyrrolidin-2-one hydrochloride (1228838-07-0) in the presence of TBTU and DIEA to obtain the title compound as white wax; MS (EI): m/e=381.3 [MH$^+$].

Example 4

3-{[6-Cyclopropylmethoxy-5-(3,3-difluoro-azetidin-1-yl)-pyridine-2-carbonyl]-amino}-3-phenyl-propionic acid ethyl ester

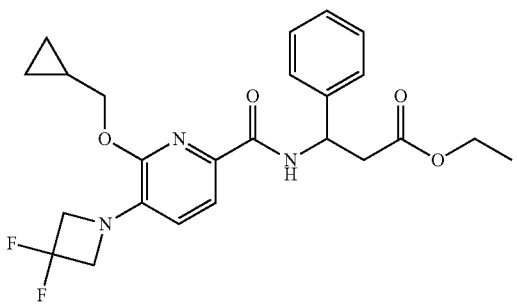 [SMILES: CCOC(=O)CC(NC(=O)c1ccc(N2CC(F)(F)C2)c(OCC2CC2)n1)c1ccccc1]

In analogy to the procedure described in Example 1 d), 6-cyclopropylmethoxy-5-(3,3-difluoro-azetidin-1-yl)-pyridine-2-carboxylic acid (Example 2 b)) was reacted with ethyl 3-amino-3-phenylpropanoate hydrochloride (29754-04-9) in the presence of TBTU and DIEA to obtain the title compound as light yellow oil; MS (EI): m/e=460.3 [MH$^+$].

Example 5

3-{[6-Cyclopropylmethoxy-5-(3,3-difluoro-azetidin-1-yl)-pyridine-2-carbonyl]-amino}-3-methyl-butyric acid ethyl ester

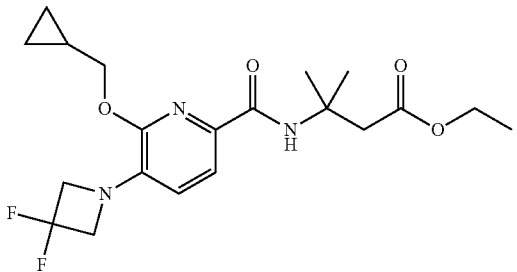 [SMILES: CCOC(=O)CC(C)(C)NC(=O)c1ccc(N2CC(F)(F)C2)c(OCC2CC2)n1]

In analogy to the procedure described in Example 1 d), 6-cyclopropylmethoxy-5-(3,3-difluoro-azetidin-1-yl)-pyridine-2-carboxylic acid (Example 2 b)) was reacted with ethyl 3-amino-3-methylbutanoate hydrochloride (85532-40-7) in the presence of TBTU and DIEA to obtain the title compound as yellow oil; MS (EI): m/e=412.3 [MH$^+$].

Example 6

6-Cyclopropylmethoxy-5-(3,3-difluoro-azetidin-1-yl)-pyridine-2-carboxylic acid (1,1-dimethyl-2-methylcarbamoyl-ethyl)-amide a) 3-{[6-Cyclopropylmethoxy-5-(3,3-difluoro-azetidin-1-yl)-pyridine-2-carbonyl]-amino}-3-methyl-butyric acid

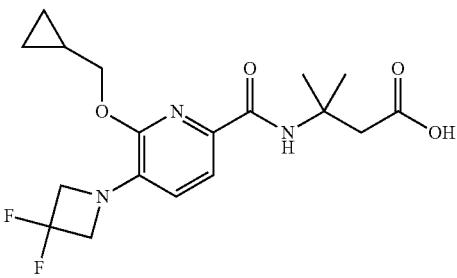 [SMILES: CC(C)(CC(=O)O)NC(=O)c1ccc(N2CC(F)(F)C2)c(OCC2CC2)n1]

A mixture of 3-{[6-cyclopropylmethoxy-5-(3,3-difluoro-azetidin-1-yl)-pyridine-2-carbonyl]-amino}-3-methyl-butyric acid ethyl ester (Example 5, 45 mg, 109 μmol) and lithium hydroxide hydrate (5.5 mg, 131 μmol) in THF (0.35 mL) and water (88 μL) was stirred at ambient temperature for 48 h. The mixture was poured onto ice-water/brine/1N aqueous HCl solution (25 mL) and extracted with EtOAc (3×30 mL). The combined extracts were washed with ice-water/brine (25 mL), dried over Na$_2$SO$_4$ and brought to dryness to give the title compound (40 mg, 95%) as light yellow wax; MS (EI): m/e=382.3 [M−H$^-$].

b) 6-Cyclopropylmethoxy-5-(3,3-difluoro-azetidin-1-yl)-pyridine-2-carboxylic acid (1,1-dimethyl-2-methylcarbamoyl-ethyl)-amide

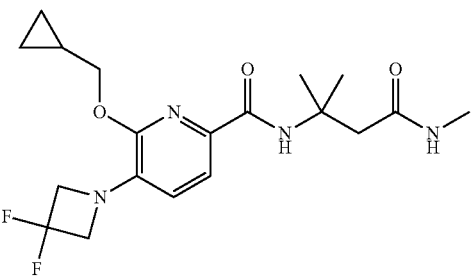 [SMILES: CNC(=O)CC(C)(C)NC(=O)c1ccc(N2CC(F)(F)C2)c(OCC2CC2)n1]

In analogy to the procedure described in Example 1 d), 3-{[6-cyclopropylmethoxy-5-(3,3-difluoro-azetidin-1-yl)-pyridine-2-carbonyl]-amino}-3-methyl-butyric acid was reacted with methanamine hydrochloride (593-51-1) in the presence of TBTU and DIEA to obtain the title compound as light yellow solid; MS (EI): m/e=397.0 [MH$^+$].

Example 7

6-Cyclopropylmethoxy-5-(3,3-difluoro-azetidin-1-yl)-pyridine-2-carboxylic acid (1-methylcarbamoyl-methyl-hexyl)-amide a) Methyl 3-(6-(cyclopropylmethoxy)-5-(3,3-difluoroazetidin-1-yl)picolinamido)octanoate

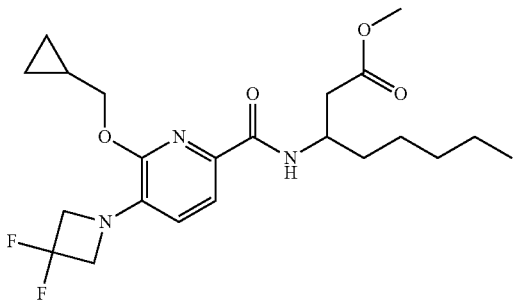 [SMILES: CCCCCC(CC(=O)OC)NC(=O)c1ccc(N2CC(F)(F)C2)c(OCC2CC2)n1]

In analogy to the procedure described in Example 1 d), 6-cyclopropylmethoxy-5-(3,3-difluoro-azetidin-1-yl)-pyridine-2-carboxylic acid (Example 2 b)) was reacted with methyl 3-aminooctanoate (1378525-06-4) in the presence of TBTU and DIEA to obtain the title compound as yellow oil; MS (EI): m/e=440.3 [MH$^+$].

b) 3-(6-(Cyclopropylmethoxy)-5-(3,3-difluoroazetidin-1-yl)picolinamido)octanoic acid

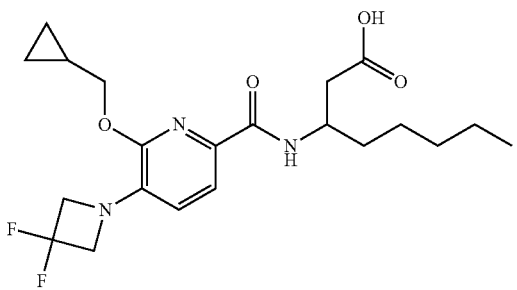 [SMILES: CCCCCC(CC(=O)O)NC(=O)c1ccc(N2CC(F)(F)C2)c(OCC2CC2)n1]

In analogy to the procedure described in Example 6 a), methyl 3-(6-(cyclopropylmethoxy)-5-(3,3-difluoroazetidin-1-yl)picolinamido)octanoate was saponified with lithium hydroxide to give the title compound as light yellow oil; MS (EI): m/e=424.4 [M–H$^-$].

c) 6-Cyclopropylmethoxy-5-(3,3-difluoro-azetidin-1-yl)-pyridine-2-carboxylic acid (1-methylcarbamoylmethyl-hexyl)-amide

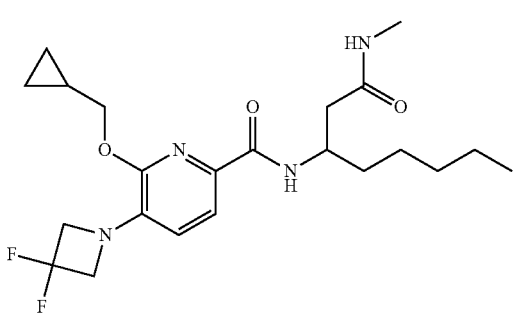 [SMILES: CCCCCC(CC(=O)NC)NC(=O)c1ccc(N2CC(F)(F)C2)c(OCC2CC2)n1]

In analogy to the procedure described in Example 1 d), 3-(6-(cyclopropylmethoxy)-5-(3,3-difluoroazetidin-1-yl)picolinamido)octanoic acid was reacted with methanamine hydrochloride (593-51-1) in the presence of TBTU and DIEA to obtain the title compound as white solid; MS (EI): m/e=439.1 [MH$^+$].

Example 8

6-Cyclopropylmethoxy-5-(3,3-difluoro-azetidin-1-yl)-pyridine-2-carboxylic acid (1-methylcarbamoyl-methyl-3-phenyl-propyl)-amide a) Methyl 3-(6-(cyclopropylmethoxy)-5-(3,3-difluoroazetidin-1-yl)picolinamido)-5-phenylpentanoate

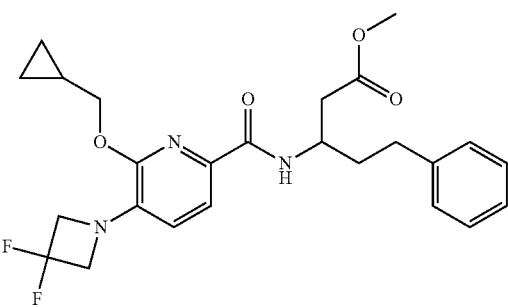 [SMILES: COC(=O)CC(CCc1ccccc1)NC(=O)c1ccc(N2CC(F)(F)C2)c(OCC2CC2)n1]

In analogy to the procedure described in Example 1 d), 6-cyclopropylmethoxy-5-(3,3-difluoro-azetidin-1-yl)-pyridine-2-carboxylic acid (Example 2 b)) was reacted with methyl 3-amino-5-phenylpentanoate hydrochloride (124082-03-7) in the presence of TBTU and DIEA to obtain the title compound as colorless oil; MS (EI): m/e=474.3 [MH$^+$].

b) 3-(6-(Cyclopropylmethoxy)-5-(3,3-difluoroazetidin-1-yl)picolinamido)-5-phenylpentanoic acid

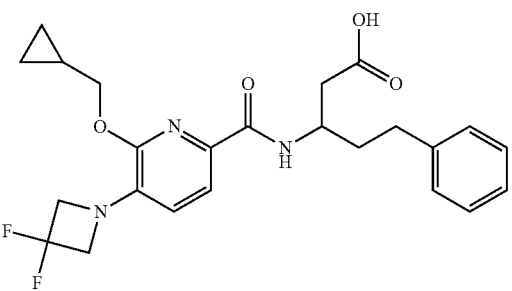 [SMILES: O=C(O)CC(CCc1ccccc1)NC(=O)c1ccc(N2CC(F)(F)C2)c(OCC2CC2)n1]

In analogy to the procedure described in Example 6 a), methyl 3-(6-(cyclopropylmethoxy)-5-(3,3-difluoroazetidin-1-yl)picolinamido)-5-phenylpentanoate was saponified with lithium hydroxide to give the title compound as white waxy solid; MS (EI): m/e=458.4 [M–H$^-$].

c) 6-Cyclopropylmethoxy-5-(3,3-difluoro-azetidin-1-yl)-pyridine-2-carboxylic acid (1-methylcarbamoylmethyl-3-phenyl-propyl)-amide

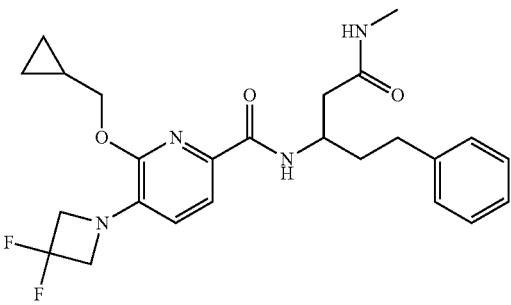 [SMILES: CNC(=O)CC(CCc1ccccc1)NC(=O)c1ccc(N2CC(F)(F)C2)c(OCC2CC2)n1]

In analogy to the procedure described in Example 1 d), 3-(6-(cyclopropylmethoxy)-5-(3,3-difluoroazetidin-1-yl)picolinamido)-5-phenylpentanoic acid was reacted with methanamine hydrochloride (593-51-1) in the presence of TBTU and DIEA to obtain the title compound as white solid; MS (EI): m/e=473.0 [MH$^+$].

Example 9

(−)-5-Cyclopropyl-6-cyclopropylmethoxy-pyridine-2-carboxylic acid (1-carbamoylmethyl-pentyl)-amide a) 5-Cyclopropyl-6-cyclopropylmethoxy-pyridine-2-carboxylic acid (1-carbamoylmethyl-pentyl)-amide

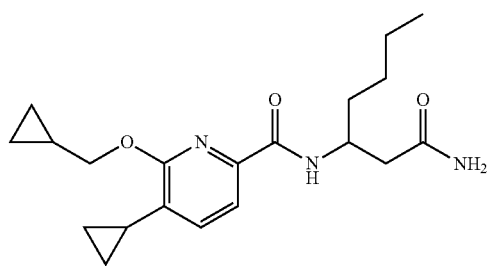 [SMILES: CCCCC(CC(N)=O)NC(=O)c1ccc(C2CC2)c(OCC2CC2)n1]

The title compound was synthesized in analogy to Example 1 d), using 5-cyclopropyl-6-cyclopropylmethoxy-pyridine-2-carboxylic acid (Example 1 c, 60 mg, 257 μmol) and 3-amino-heptanamide (771528-67-7; 40.8 mg, 283 μmol) as starting materials and isolated (75 mg, 81%) as white solid; LC-MS (UV peak area, ESI) 100%, 360.2286 [MH$^+$].

b) (−)-5-Cyclopropyl-6-cyclopropylmethoxy-pyridine-2-carboxylic acid (1-carbamoylmethyl-pentyl)-amide

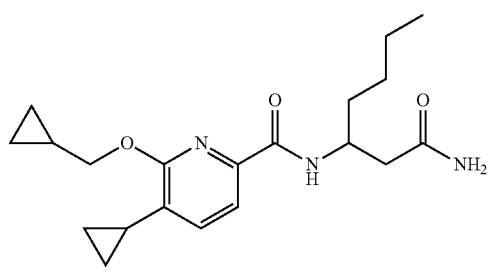 [SMILES: CCCCC(CC(N)=O)NC(=O)c1ccc(C2CC2)c(OCC2CC2)n1]

The enantiomers of 5-cyclopropyl-6-cyclopropylmethoxy-pyridine-2-carboxylic acid (1-carbamoylmethyl-pentyl)-amide (Example 9 a) were separated by chiral HPLC (Reprosil Chiral NR, 15% ethanol in n-heptane). The (−) enantiomer (27 mg, 38%) was isolated as white solid; LC-MS (UV peak area/ESI) 100%, 360.2289 [MH$^+$]; $\alpha_D^{20}$ (MeOH)=−24.5°.

Example 10

(+)-5-Cyclopropyl-6-cyclopropylmethoxy-pyridine-2-carboxylic acid (1-carbamoylmethyl-pentyl)-amide

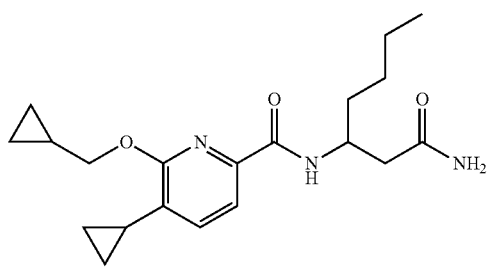 [SMILES: CCCCC(CC(N)=O)NC(=O)c1ccc(C2CC2)c(OCC2CC2)n1]

The enantiomers of 5-cyclopropyl-6-cyclopropylmethoxy-pyridine-2-carboxylic acid (1-carbamoylmethyl-pentyl)-amide (Example 9 a) were separated by chiral HPLC (Reprosil Chiral NR, 15% ethanol in n-heptane). The (+) enantiomer (27 mg, 38%) was isolated as white solid; LC-MS (UV peak area/ESI) 100%, 360.2289 [MH$^+$]; $\alpha_D^{20}$ (MeOH)=+25.1°.

Example 11

2-[({[6-(Cyclopropylmethoxy)-5-(3,3-difluoroazetidin-1-yl)pyridin-2-yl]carbonyl}amino)methyl]-4-methylpentanoic acid a) 2-[({[6-(Cyclopropylmethoxy)-5-(3,3-difluoro-azetidin-1-yl)pyridin-2-yl]carbonyl}amino)methyl]-4-methylpentanoic acid methyl ester

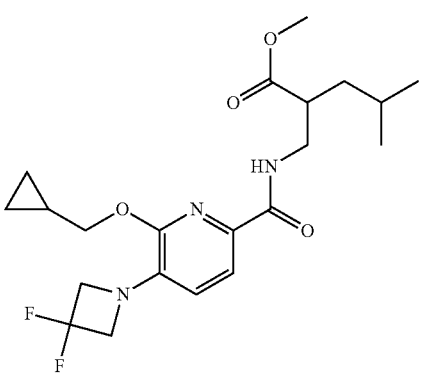 [SMILES: COC(=O)C(CNC(=O)c1ccc(N2CC(F)(F)C2)c(OCC2CC2)n1)CC(C)C]

In analogy to the procedure described in Example 1 d), 6-cyclopropylmethoxy-5-(3,3-difluoro-azetidin-1-yl)-pyridine-2-carboxylic acid (Example 2 b)) was reacted with methyl 2-(aminomethyl)-4-methylpentanoate hydrochloride (864182-44-5) in the presence of TBTU and DIEA to obtain the title compound as colorless oil; MS (EI): m/e=426.1 [MH+].

b) 2-[({[6-(Cyclopropylmethoxy)-5-(3,3-difluoro-azetidin-1-yl)pyridin-2-yl]carbonyl}amino)methyl]-4-methylpentanoic acid

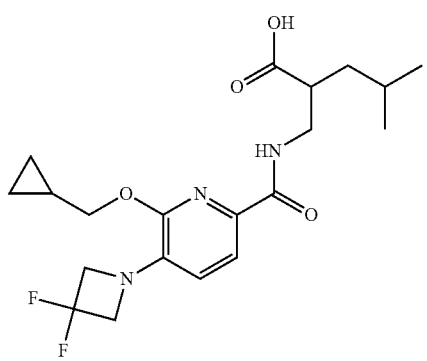 [SMILES: CC(C)CC(CNC(=O)c1ccc(N2CC(F)(F)C2)c(OCC2CC2)n1)C(=O)O]

In analogy to the procedure described in Example 6 a), 2-[({[6-(cyclopropylmethoxy)-5-(3,3-difluoroazetidin-1-yl)pyridin-2-yl]carbonyl}amino)methyl]-4-methylpentanoic acid methyl ester was saponified with lithium hydroxide to give the title compound as colorless oil; MS (EI): m/e=410.0 [M−H−].

Example 12

5-Cyclopropyl-6-cyclopropylmethoxy-pyridine-2-carboxylic acid (rel-(1S,2R)-2-carbamoyl-cyclohexyl)-amide

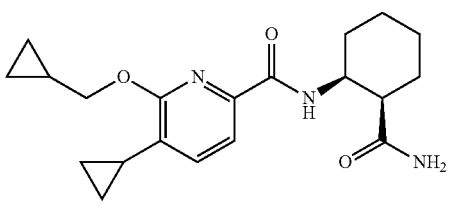 [SMILES: NC(=O)[C@@H]1CCCC[C@@H]1NC(=O)c1ccc(C2CC2)c(OCC2CC2)n1]

The title compound was synthesized in analogy to Example 1 d), using 5-cyclopropyl-6-cyclopropylmethoxy-pyridine-2-carboxylic acid (Example 1 c, 70 mg, 300 µmol) and rel-(1R,2S)-2-amino-cyclohexanecarboxamide (24717-01-9; 46.9 mg, 330 µmol) as starting materials and isolated (100 mg, 93%) as white solid; LC-MS (UV peak area, ESI) 95%, 358.2121 [MH+].

Example 13

5-Cyclopropyl-6-cyclopropylmethoxy-pyridine-2-carboxylic acid ((R)-1-carbamoylmethyl-2-methyl-propyl)-amide a) (R)-3-Amino-4-methyl-pentanamide hydrochloride

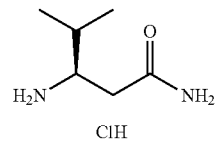

To a solution of (3R)-3-amino-4-methyl-pentanoic acid methyl ester hydrochloride (1:1) (CAN 172823-13-1, 200 mg, 1.1 mmol) in toluene (4.0 mL) was added ammonium hydroxide in water (25%, 4.0 mL, 25.7 mmol). The mixture was stirred in a closed tube at room temperature for 4 days. Solvents were removed in vacuo and remaining water was removed by azeotropic distillation with toluene. The residue was dried in high-vacuum at 40° C. to give the desired product (183 mg, 99%) as white solid; LC-MS (ESI), 131.1182 [MH+].

b) 5-Cyclopropyl-6-cyclopropylmethoxy-pyridine-2-carboxylic acid ((R)-1-carbamoylmethyl-2-methyl-propyl)-amide

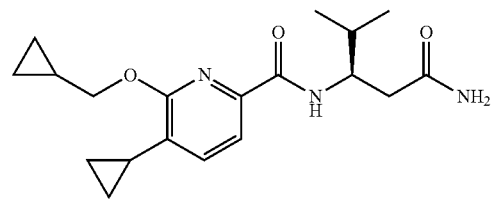 [SMILES: CC(C)[C@@H](CC(N)=O)NC(=O)c1ccc(C2CC2)c(OCC2CC2)n1]

The title compound was synthesized in analogy to Example 1 d), using 5-cyclopropyl-6-cyclopropylmethoxy-pyridine-2-carboxylic acid (Example 1 c, 40 mg, 171 µmol) and (R)-3-amino-4-methyl-pentanamide hydrochloride (31.4 mg, 189 µmol) as starting materials and isolated (51 mg, 86%) as white solid; ~95% ee by chiral NMR, LC-MS (UV peak area, ESI) 95%, 346.2122 [MH+]; $\alpha_D^{20}$ (MeOH)=+3.1°.

Example 14

5-Cyclopropyl-6-cyclopropylmethoxy-pyridine-2-carboxylic acid ((S)-1-carbamoylmethyl-2-methyl-propyl)-amide

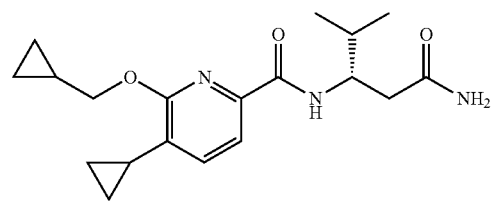 [SMILES: CC(C)[C@H](CC(N)=O)NC(=O)c1ccc(C2CC2)c(OCC2CC2)n1]

The title compound was synthesized in analogy to Example 1 d), using 5-cyclopropyl-6-cyclopropylmethoxy-pyridine-2-carboxylic acid (Example 1 c, 40 mg, 171 μmol) and (S)-3-amino-4-methyl-pentanamide hydrochloride (CAN 173336-51-1, 31.4 mg, 189 μmol) as starting materials and isolated (48 mg, 81%) as white solid; ~92% ee by chiral NMR, LC-MS (UV peak area, ESI) 95.5%, 346.2127 [MH⁺]; $\alpha_D^{20}$ (MeOH)=−2.3°.

Example 15

(+)-cis-5-Cyclopropyl-6-cyclopropylmethoxy-pyridine-2-carboxylic acid (2-carbamoyl-cyclohexyl)-amide

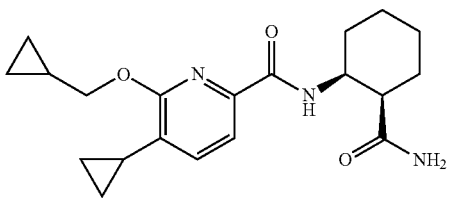 [SMILES: NC(=O)[C@@H]1CCCC[C@@H]1NC(=O)c1ccc(C2CC2)c(OCC2CC2)n1]

The enantiomers of 5-cyclopropyl-6-cyclopropylmethoxy-pyridine-2-carboxylic acid (rel-(1S,2R)-2-carbamoyl-cyclohexyl)-amide (Example 12) were separated by chiral HPLC (Reprosil Chiral NR, 10% isopropanol in n-heptane). The (+) enantiomer (33 mg, 38%) was isolated as white solid; LC-MS (UV peak area/ESI) 97%, 358.2120 [MH⁺].

Example 16

(−)-trans-5-Cyclopropyl-6-cyclopropylmethoxy-pyridine-2-carboxylic acid (2-carbamoyl-cyclohexyl)-amide a) 5-Cyclopropyl-6-cyclopropylmethoxy-pyridine-2-carboxylic acid (rel-(1R,2R)-2-carbamoyl-cyclohexyl)-amide

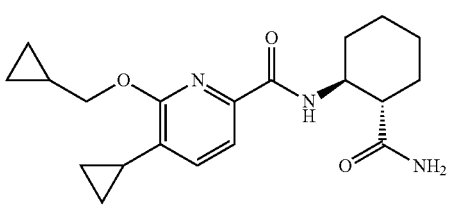 [SMILES: NC(=O)[C@H]1CCCC[C@@H]1NC(=O)c1ccc(C2CC2)c(OCC2CC2)n1]

The title compound was synthesized in analogy to Example 1 d), using 5-cyclopropyl-6-cyclopropylmethoxy-pyridine-2-carboxylic acid (Example 1 c, 70 mg, 300 μmol) and rel-(1R,2R)-2-amino-cyclohexanecarboxamide hydrochloride (1212336-68-9; 64.3 mg, 360 mol) as starting materials and isolated (69 mg, 64%) as white solid; LC-MS (UV peak area, ESI) 95%, 358.2135 [MH⁺].

b) (−)-trans-5-Cyclopropyl-6-cyclopropylmethoxy-pyridine-2-carboxylic acid (2-carbamoyl-cyclohexyl)-amide

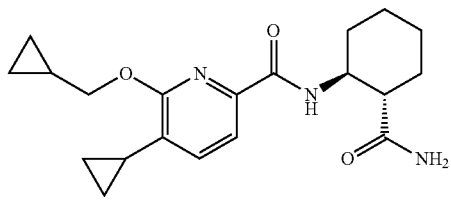 [SMILES: NC(=O)[C@H]1CCCC[C@@H]1NC(=O)c1ccc(C2CC2)c(OCC2CC2)n1]

The enantiomers of 5-cyclopropyl-6-cyclopropylmethoxy-pyridine-2-carboxylic acid (rel-(1R,2R)-2-carbamoyl-cyclohexyl)-amide (Example 16 a) were separated by chiral HPLC (Lux-5u Amylose-2, 20% ethanol in n-heptane). The (−)-enantiomer (28 mg, 42%) was isolated as white solid; LC-MS (UV peak area/ESI) 97%, 358.2123 [MH⁺].

Example 17

(−)-5-Cyclopropyl-6-cyclopropylmethoxy-pyridine-2-carboxylic acid (2-carbamoyl-1-cyclohexyl-ethyl)-amide a) 5-Cyclopropyl-6-cyclopropylmethoxy-pyridine-2-carboxylic acid (2-carbamoyl-1-cyclohexyl-ethyl)-amide

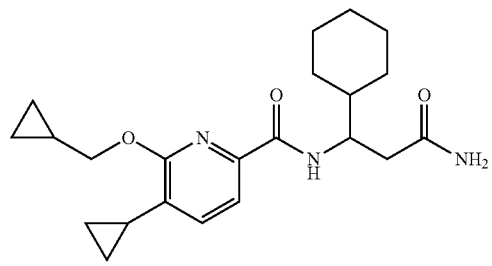 [SMILES: NC(=O)CC(NC(=O)c1ccc(C2CC2)c(OCC2CC2)n1)C1CCCCC1]

The title compound was synthesized in analogy to Example 1 d), using 5-cyclopropyl-6-cyclopropylmethoxy-pyridine-2-carboxylic acid (Example 1 c, 80 mg, 343 μmol) and β-amino-cyclohexanepropanamide hydrochloride (1:1) (1375473-18-9; 70.9 mg, 377 μmol) as starting materials and isolated (78 mg, 59%) as white solid; LC-MS (UV peak area, ESI) 94%, 386.2450 [MH⁺].

b) (−)-5-Cyclopropyl-6-cyclopropylmethoxy-pyridine-2-carboxylic acid (2-carbamoyl-1-cyclohexyl-ethyl)-amide

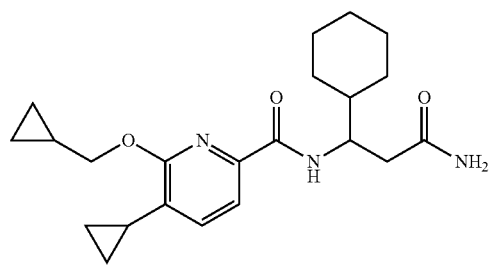 [SMILES: NC(=O)CC(NC(=O)c1ccc(C2CC2)c(OCC2CC2)n1)C1CCCCC1]

The enantiomers of 5-cyclopropyl-6-cyclopropylmethoxy-pyridine-2-carboxylic acid (2-carbamoyl-1-cyclohexyl-ethyl)-amide (Example 17a) were separated by chiral HPLC (Reprosil Chiral NR, 10% ethanol in n-heptane). The (−) enantiomer (31 mg, 41%) was isolated as white solid; (−)-enantiomer with ee ~100%, LC-MS (UV peak area/ESI) 100%, 386.2447 [MH+].

Example 18

(+)-5-Cyclopropyl-6-cyclopropylmethoxy-pyridine-2-carboxylic acid (2-carbamoyl-1-cyclohexyl-ethyl)-amide

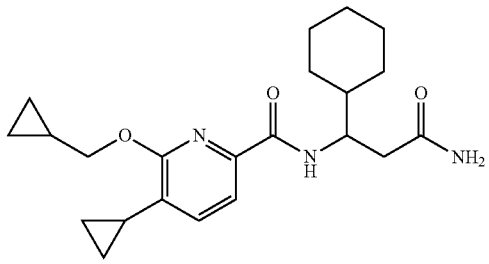 [SMILES: NC(=O)CC(NC(=O)c1ccc(C2CC2)c(OCC2CC2)n1)C1CCCCC1]

The enantiomers of 5-cyclopropyl-6-cyclopropylmethoxy-pyridine-2-carboxylic acid (2-carbamoyl-1-cyclohexyl-ethyl)-amide (Example 17a) were separated by chiral HPLC (Reprosil Chiral NR, 10% ethanol in n-heptane). The (+) enantiomer (29 mg, 38%) was isolated as white solid; (+)-enantiomer with ee ~100%, LC-MS (UV peak area/ESI) 98%, 386.2440 [MH+].

Example 19

6-Cyclopropylmethoxy-5-(3,3-difluoro-azetidin-1-yl)-pyridine-2-carboxylic acid ((S)-1-carbamoylmethyl-2-methyl-propyl)-amide

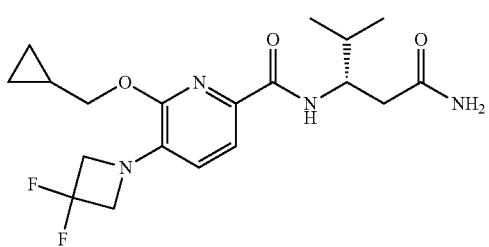 [SMILES: CC(C)[C@H](CC(N)=O)NC(=O)c1ccc(N2CC(F)(F)C2)c(OCC2CC2)n1]

The title compound was synthesized in analogy to Example 1 d), using 6-cyclopropylmethoxy-5-(3,3-difluoro-azetidin-1-yl)-pyridine-2-carboxylic acid (Example 2 b, 50 mg, 176 µmol) and (3S)-3-amino-4-methyl-pentanamide monohydrochloride (173336-51-1; 32.2 mg, 193 µmol) as starting materials and isolated (59 mg, 85%) as white solid; LC-MS (UV peak area, ESI) 97.9%, 397.2049 [MH+].

Example 20

(+)-cis-6-Cyclopropylmethoxy-5-(3,3-difluoro-azetidin-1-yl)-pyridine-2-carboxylic acid (2-carbamoyl-cyclohexyl)-amide a) 6-Cyclopropylmethoxy-5-(3,3-difluoro-azetidin-1-yl)-pyridine-2-carboxylic acid (rel-(1R,2S)-2-carbamoyl-cyclohexyl)-amide

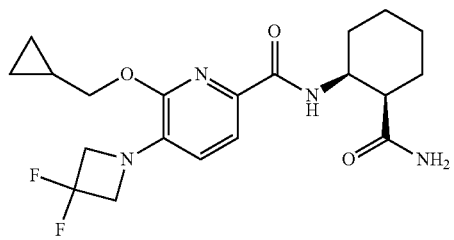 [SMILES: NC(=O)[C@@H]1CCCC[C@@H]1NC(=O)c1ccc(N2CC(F)(F)C2)c(OCC2CC2)n1]

The title compound was synthesized in analogy to Example 1 d), using 6-cyclopropylmethoxy-5-(3,3-difluoro-azetidin-1-yl)-pyridine-2-carboxylic acid (Example 2 b, 100 mg, 352 µmol) and rel-(1R,2S)-2-amino-cyclohexanecarboxamide (24717-01-9; 55.0 mg, 387 µmol) as starting materials and isolated (150 mg, quant.) as white solid; LC-MS (UV peak area, ESI) 100%, 409.2052 [MH+].

b) (+)-cis-6-Cyclopropylmethoxy-5-(3,3-difluoro-azetidin-1-yl)-pyridine-2-carboxylic acid (2-carbamoyl-cyclohexyl)-amide or enantiomer

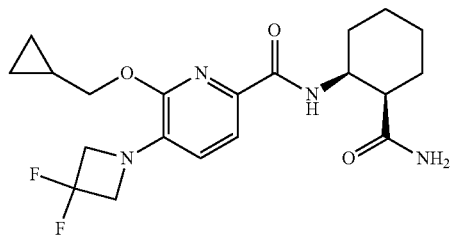 [SMILES: NC(=O)[C@@H]1CCCC[C@@H]1NC(=O)c1ccc(N2CC(F)(F)C2)c(OCC2CC2)n1]

The enantiomers of 6-cyclopropylmethoxy-5-(3,3-difluoro-azetidin-1-yl)-pyridine-2-carboxylic acid (rel-(1R,2S)-2-carbamoyl-cyclohexyl)-amide (Example 20 a) were separated by chiral HPLC (Chiralpak AD, 15% isopropanol in n-heptane). The (+) enantiomer (51 mg, 34%) was isolated as white solid; (+)-enantiomer with ee ~100%, LC-MS (UV peak area/ESI) 100%, 409.2047 [MH+].

Example 21

(−)-cis-6-Cyclopropylmethoxy-5-(3,3-difluoro-azetidin-1-yl)-pyridine-2-carboxylic acid (2-carbamoyl-cyclohexyl)-amide

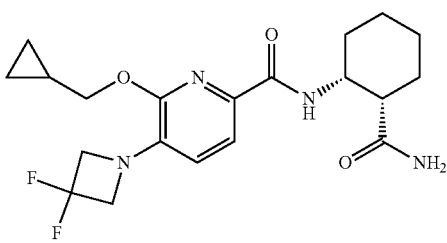 [SMILES: NC(=O)[C@H]1CCCC[C@H]1NC(=O)c1ccc(N2CC(F)(F)C2)c(OCC2CC2)n1]

The enantiomers of 6-cyclopropylmethoxy-5-(3,3-difluoro-azetidin-1-yl)-pyridine-2-carboxylic acid (rel-(1R, 2S)-2-carbamoyl-cyclohexyl)-amide (Example 20 a) were separated by chiral HPLC (Chiralpak AD, 15% isopropanol in n-heptane). The (−) enantiomer (50 mg, 34%) was isolated as white solid; (−)-enantiomer with ee ~96.6%, LC-MS (UV peak area/ESI) 98.3%, 409.2048 [MH$^+$].

Example 22

3-[(5-Cyclopropyl-6-cyclopropylmethoxy-pyridine-2-carbonyl)-amino]-5-methyl-hexanoic acid ethyl ester chain

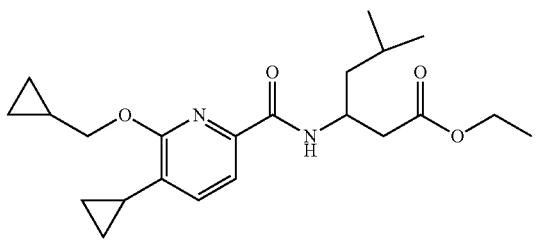 [SMILES: CCOC(=O)CC(CC(C)C)NC(=O)c1ccc(C2CC2)c(OCC2CC2)n1]

The title compound was synthesized in analogy to Example 1 d), using 5-cyclopropyl-6-cyclopropylmethoxy-pyridine-2-carboxylic acid (Example 1 c, 100 mg, 429 µmol) and 3-amino-5-methyl-hexanoic acid ethyl ester (90726-94-6; 89.1 mg, 514 µmol) as starting materials and isolated (63 mg, 38%) as light-yellow oil; MS (389.6 [MH$^+$].

Example 23

5-Cyclopropyl-6-cyclopropylmethoxy-pyridine-2-carboxylic acid (3-carbamoylmethyl-oxetan-3-yl)-amide a) 2-(3-Amino-oxetan-3-yl)-acetamide

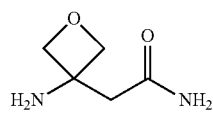

To a solution of 3-amino-3-oxetaneacetic acid ethyl ester (400 mg, 2.51 mmol) in toluene (8.0 mL) was added ammonium hydroxide in water (25%, 8.0 mL, 51.4 mmol). The mixture was stirred in a closed tube at room temperature for 6 days. Solvents were removed in vacuo and remaining water was removed by azeotropic distillation with toluene. The residue was dried in high-vacuum at 40° C. to give the desired product (290 mg, 89%) as white solid; GC-MS (ESI), 131.0817 [MH$^+$].

b) 5-Cyclopropyl-6-cyclopropylmethoxy-pyridine-2-carboxylic acid (3-carbamoylmethyl-oxetan-3-yl)-amide

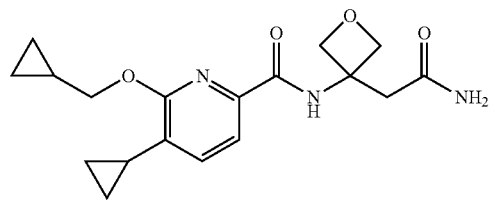 [SMILES: NC(=O)CC1(NC(=O)c2ccc(C3CC3)c(OCC3CC3)n2)COC1]

The title compound was synthesized in analogy to Example 1 d), using 5-cyclopropyl-6-cyclopropylmethoxy-pyridine-2-carboxylic acid (Example 1 c, 50 mg, 214 µmol) and 2-(3-amino-oxetan-3-yl)-acetamide (33.5 mg, 257 µmol) as starting materials and isolated (53 mg, 72%) as white solid; LC-MS (UV peak area, ESI) 100%, 346.1760 [MH$^+$].

Example 24

(−)-5-Cyclopropyl-6-cyclopropylmethoxy-pyridine-2-carboxylic acid (1-carbamoylmethyl-3-methyl-butyl)-amide a) 5-Cyclopropyl-6-cyclopropylmethoxy-pyridine-2-carboxylic acid (1-carbamoylmethyl-3-methyl-butyl)-amide

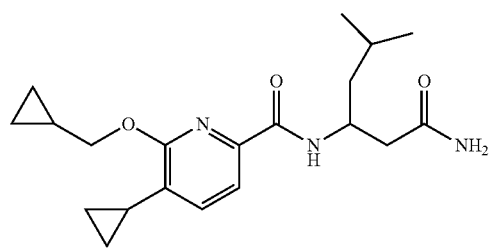

The title compound was synthesized in analogy to Example 1 d), using 5-cyclopropyl-6-cyclopropylmethoxy-pyridine-2-carboxylic acid (Example 1 c, 100 mg, 429 µmol) and 3-amino-5-methyl-hexanamide hydrochloride (1:1) (92.9 mg, 514 µmol) as starting materials and isolated (73 mg, 47%) as white solid; LC-MS (UV peak area, ESI) 98.5%, 360.2283 [MH$^+$].

b) (−)-5-Cyclopropyl-6-cyclopropylmethoxy-pyridine-2-carboxylic acid (1-carbamoylmethyl-3-methyl-butyl)-amide

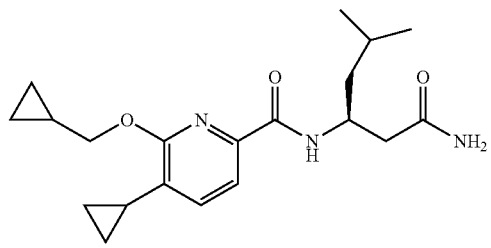 [SMILES: CC(C)CC(CC(N)=O)NC(=O)c1ccc(C2CC2)c(OCC2CC2)n1]

The enantiomers of 5-cyclopropyl-6-cyclopropylmethoxy-pyridine-2-carboxylic acid (1-carbamoylmethyl-3-methyl-butyl)-amide (Example 24 a) were separated by chiral HPLC (Reprosil chiral NR, 10% ethanol in n-heptane). The (−)-enantiomer (28 mg, 38%) was isolated as white solid; LC-MS (UV peak area/ESI) 100%, 360.2280 [MH$^+$].

Example 25

(+)-5-Cyclopropyl-6-cyclopropylmethoxy-pyridine-2-carboxylic acid (1-carbamoylmethyl-3-methyl-butyl)-amide

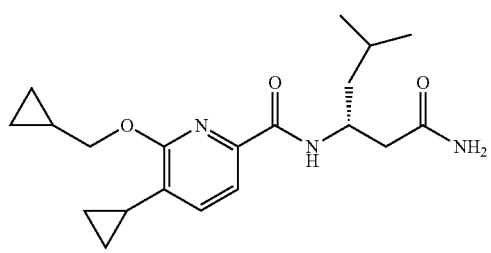 [SMILES: CC(C)C[C@H](CC(N)=O)NC(=O)c1ccc(C2CC2)c(OCC2CC2)n1]

The enantiomers of 5-cyclopropyl-6-cyclopropylmethoxy-pyridine-2-carboxylic acid (1-carbamoylmethyl-3-methyl-butyl)-amide (Example 24 a) were separated by chiral HPLC (Reprosil chiral NR, 10% ethanol in n-heptane). The (+)-enantiomer (30 mg, 41%) was isolated as white solid; LC-MS (UV peak area/ESI) 100%, 360.2294 [MH$^+$].

Example 26

6-Cyclopropylmethoxy-5-(3,3-difluoro-azetidin-1-yl)-pyridine-2-carboxylic acid (3-carbamoylmethyl-oxetan-3-yl)-amide

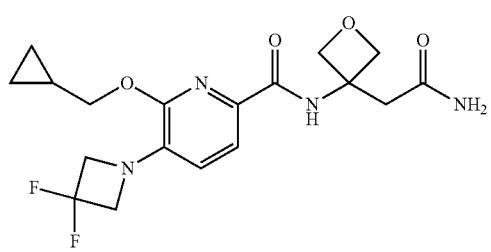 [SMILES: NC(=O)CC1(NC(=O)c2ccc(N3CC(F)(F)C3)c(OCC3CC3)n2)COC1]

The title compound was synthesized in analogy to Example 1 d, using 6-cyclopropylmethoxy-5-(3,3-difluoro-azetidin-1-yl)-pyridine-2-carboxylic acid (Example 2 b, 50 mg, 176 μmol) and 2-(3-amino-oxetan-3-yl)-acetamide (Example 23 a, 25.2 mg, 193 mol) as starting materials and isolated (34 mg, 49%) as white solid; LC-MS (UV peak area, ESI) 100%, 397.1689 [MH$^+$].

Example 27

(−)-5-Cyclopropyl-6-cyclopropylmethoxy-pyridine-2-carboxylic acid (2-carbamoyl-1-cyclopropyl-ethyl)-amide a) 5-Cyclopropyl-6-cyclopropylmethoxy-pyridine-2-carboxylic acid (2-carbamoyl-1-cyclopropyl-ethyl)-amide

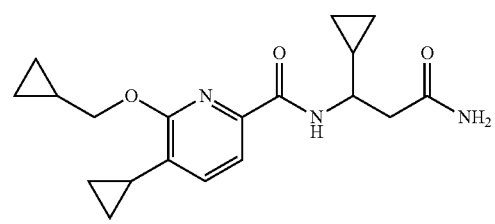 [SMILES: NC(=O)CC(NC(=O)c1ccc(C2CC2)c(OCC2CC2)n1)C1CC1]

The title compound was synthesized in analogy to Example 1 d), using 5-cyclopropyl-6-cyclopropylmethoxy-pyridine-2-carboxylic acid (Example 1 c, 100 mg, 429 μmol) and β-amino-cyclopropanepropanamide hydrochloride (1:1) (CAN 1354953-76-6, 70.6 mg, 472 mol) as starting materials and isolated (134 mg, 91%) as white solid; LC-MS (UV peak area, ESI) 100%, 344.1964 [MH$^+$].

b) (−)-5-Cyclopropyl-6-cyclopropylmethoxy-pyridine-2-carboxylic acid (2-carbamoyl-1-cyclopropyl-ethyl)-amide

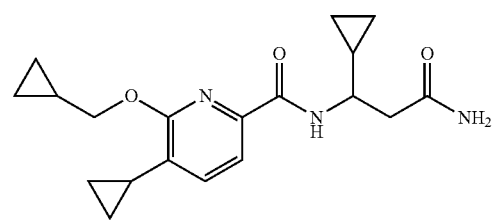 [SMILES: NC(=O)CC(NC(=O)c1ccc(C2CC2)c(OCC2CC2)n1)C1CC1]

The enantiomers of 5-cyclopropyl-6-cyclopropylmethoxy-pyridine-2-carboxylic acid (2-carbamoyl-1-cyclopropyl-ethyl)-amide (Example 27 a) were separated by chiral HPLC (Reprosil chiral NR, 10% ethanol in n-heptane). The (−)-enantiomer (59 mg, 45%) was isolated as white solid; LC-MS (UV peak area/ESI) 100%, 344.1960 [MH$^+$].

Example 28

(+)-5-Cyclopropyl-6-cyclopropylmethoxy-pyridine-2-carboxylic acid (2-carbamoyl-1-cyclopropyl-ethyl)-amide

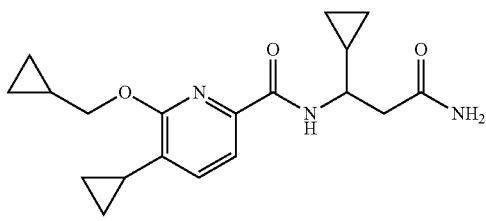 [SMILES: NC(=O)CC(NC(=O)c1ccc(C2CC2)c(OCC2CC2)n1)C1CC1]

The enantiomers of 5-cyclopropyl-6-cyclopropyl-methoxy-pyridine-2-carboxylic acid (2-carbamoyl-1-cyclopropyl-ethyl)-amide (Example 27 a) were separated by chiral HPLC (Reprosil chiral NR, 10% ethanol in n-heptane). The (+)-enantiomer (59 mg, 45%) was isolated as white solid; LC-MS (UV peak area/ESI) 100%, 344.1967 [MH$^+$].

Example 29

5-Cyclopropyl-6-cyclopropylmethoxy-pyridine-2-carboxylic acid ((R)-1-carbamoylmethyl-2,2-dimethyl-propyl)-amide

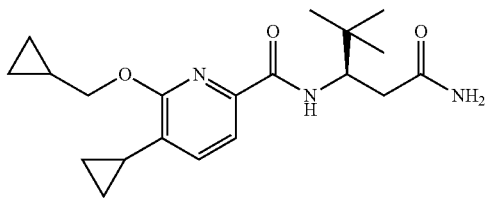 [SMILES: CC(C)(C)[C@@H](CC(N)=O)NC(=O)c1ccc(C2CC2)c(OCC2CC2)n1]

The title compound was synthesized in analogy to Example 1 d), using 5-cyclopropyl-6-cyclopropylmethoxy-pyridine-2-carboxylic acid (Example 1 c, 50 mg, 214 µmol) and (3R)-3-amino-4,4-dimethyl-pentanamide (CAN 1134859-25-8, 42.6 mg, 236 µmol) as starting materials and isolated (77.1 mg, 81%) as white solid; LC-MS (UV peak area, ESI) 100%, 360.2279 [MH$^+$].

Example 30

5-Cyclopropyl-6-cyclopropylmethoxy-pyridine-2-carboxylic acid [2-carbamoyl-1-(tetrahydro-pyran-4-yl)-ethyl]-amide

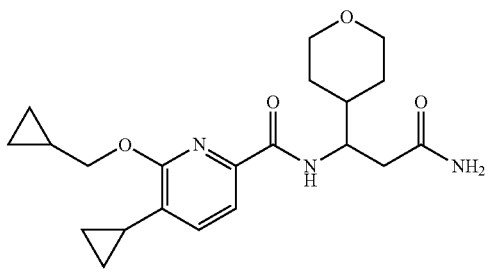 [SMILES: NC(=O)CC(NC(=O)c1ccc(C2CC2)c(OCC2CC2)n1)C1CCOCC1]

The title compound was synthesized in analogy to Example 1 d), using 5-cyclopropyl-6-cyclopropylmethoxy-pyridine-2-carboxylic acid (Example 1 c, 100 mg, 429 µmol) and β-aminotetrahydro-2H-pyran-4-propanamide hydrochloride (1:1) (CAN 1375473-17-8, 98.4 mg, 472 µmol) as starting materials and isolated (160 mg, 96%) as white solid; LC-MS (UV peak area, ESI) 100%, 388.2235 [MH$^+$].

Example 31

(−)-5-Cyclopropyl-6-cyclopropylmethoxy-pyridine-2-carboxylic acid (1-carbamoylmethyl-2,2,2-trifluoro-ethyl)-amide a) 5-Cyclopropyl-6-cyclopropylmethoxy-pyridine-2-carboxylic acid (1-carbamoylmethyl-2,2,2-trifluoro-ethyl)-amide

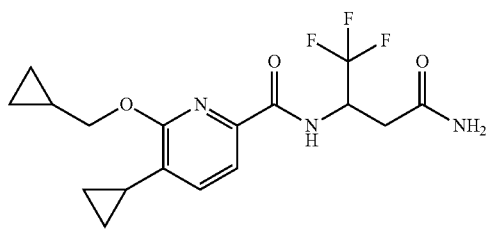 [SMILES: NC(=O)CC(NC(=O)c1ccc(C2CC2)c(OCC2CC2)n1)C(F)(F)F]

The title compound was synthesized in analogy to Example 1 d), using 5-cyclopropyl-6-cyclopropylmethoxy-pyridine-2-carboxylic acid (Example 1 c, 100 mg, 429 µmol) and 3-amino-4,4,4-trifluoro-butanamide (CAN 453-32-7, 73.6 mg, 472 µmol) as starting materials and isolated (129 mg, 81%) as white solid; LC-MS (UV peak area, ESI) 97.4%, 372.1529 [MH$^+$].

b) (−)-5-Cyclopropyl-6-cyclopropylmethoxy-pyridine-2-carboxylic acid (1-carbamoylmethyl-2,2,2-trifluoro-ethyl)-amide

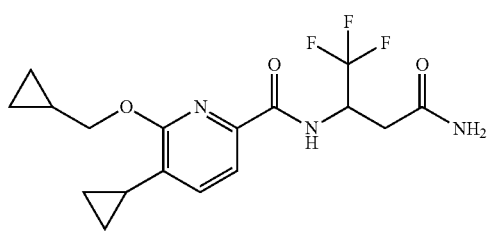 [SMILES: NC(=O)CC(NC(=O)c1ccc(C2CC2)c(OCC2CC2)n1)C(F)(F)F]

The enantiomers of 5-cyclopropyl-6-cyclopropyl-methoxy-pyridine-2-carboxylic acid (1-carbamoylmethyl-2,2,2-trifluoro-ethyl)-amide (Example 31 a) were separated by chiral HPLC (Lux 5u Amylose-2, 8% ethanol in n-heptane). The (−)-enantiomer (48 mg, 42%) was isolated as white solid; LC-MS (UV peak area/ESI) 100%, 372.1530 [MH$^+$].

Example 32

(+)-5-Cyclopropyl-6-cyclopropylmethoxy-pyridine-2-carboxylic acid (1-carbamoylmethyl-2,2,2-trifluoro-ethyl)-amide

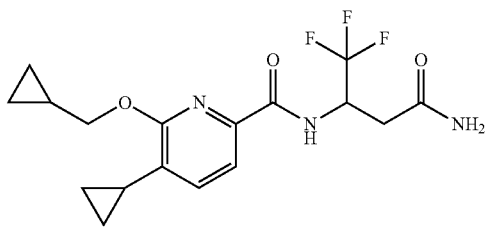 [SMILES: NC(=O)CC(NC(=O)c1ccc(C2CC2)c(OCC2CC2)n1)C(F)(F)F]

The enantiomers of 5-cyclopropyl-6-cyclopropylmethoxy-pyridine-2-carboxylic acid (1-carbamoylmethyl-2,2,2-trifluoro-ethyl)-amide (Example 31 a) were separated by chiral HPLC (Lux 5u Amylose-2, 8% ethanol in n-heptane). The (+)-enantiomer (49 mg, 43%) was isolated as white solid; LC-MS (UV peak area/ESI) 100%, 372.1530 [MH$^+$].

Example 33

5-Cyclopropyl-6-(2,2,2-trifluoro-1-methyl-ethoxy)-pyridine-2-carboxylic acid (3-carbamoylmethyl-oxetan-3-yl)-amide a)
5-Bromo-6-(1,1,1-trifluoropropan-2-yloxy)picolinic acid

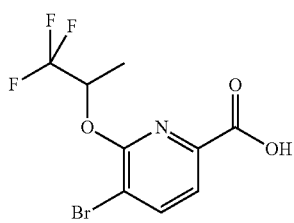 [SMILES: CC(Oc1nc(C(=O)O)ccc1Br)C(F)(F)F]

5-Bromo-6-chloropicolinic acid (5 g, 21.1 mmol; CAN 959958-25-9) was dissolved in DMSO (100 mL) to give a colorless solution. To this solution potassium hydroxide (4.75 g, 84.6 mmol) was added. The reaction mixture turned into a white suspension which was stirred for 15 min. Then 1,1,1-trifluoropropan-2-ol (2.41 g, 1.92 mL, 21.1 mmol) was added. The mixture was stirred for 1 d at ambient temp., poured onto ice-water/1N HCl (200 mL) and extracted with EtOAc (2×400 mL). The organic layers were washed with ice-water/brine (200 mL), combined and dried over Na$_2$SO$_4$ and concentrated in vacuo to give the title compound (6.9 g, quant.) as orange solid. MS (EI): m/e=312.3 [M−H]$^-$.

b) 5-Cyclopropyl-6-(1,1,1-trifluoropropan-2-yloxy) picolinic acid

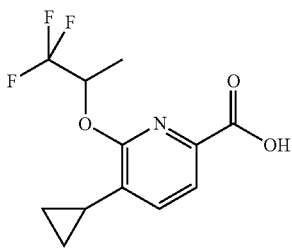 [SMILES: CC(Oc1nc(C(=O)O)ccc1C1CC1)C(F)(F)F]

5-Bromo-6-(1,1,1-trifluoropropan-2-yloxy)picolinic acid (2 g, 6.37 mmol), potassium cyclopropyltrifluoroborate (952 mg, 6.43 mmol), cesium carbonate (6.22 g, 19.1 mmol) and palladium(II)acetate (28.6 mg, 127 μmol) were suspended in toluene (55 mL) and water (6.11 mL) under an argon atmosphere. Butyl-1-adamantylphosphin (68.5 mg, 191 mol) was added, the reaction mixture was heated to 120° C. for 1 d, poured onto ice-water/1N HCl (150 mL) and extracted with EtOAc (2×300 mL). The combined organic layers were washed with ice-water/brine (150 mL), dried over Na$_2$SO$_4$ and concentrated in vacuo to give the title compound (1.38 g, 79%) as a yellow solid. MS (EI): m/e=276.2 [M+H]$^+$.

c) 5-Cyclopropyl-6-(2,2,2-trifluoro-1-methyl-ethoxy)-pyridine-2-carboxylic acid (3-carbamoylmethyl-oxetan-3-yl)-amide

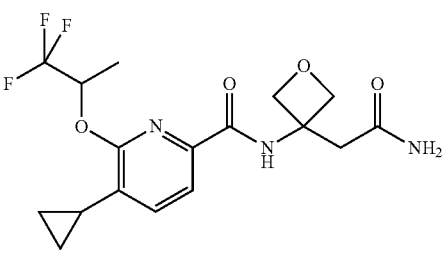 [SMILES: CC(Oc1nc(C(=O)NC2(CC(N)=O)COC2)ccc1C1CC1)C(F)(F)F]

In analogy to the procedure described in Example 1 d), 5-cyclopropyl-6-(1,1,1-trifluoropropan-2-yloxy)picolinic acid was reacted with 2-(3-amino-oxetan-3-yl)-acetamide (Example 23 a)) in the presence of TBTU and DIEA to obtain the title compound as white solid; MS (EI): m/e=388.3 [MH$^+$].

Example 34

(−)-5-Cyclopropyl-6-cyclopropylmethoxy-pyridine-2-carboxylic acid [2-carbamoyl-1-(tetrahydro-pyran-4-yl)-ethyl]-amide

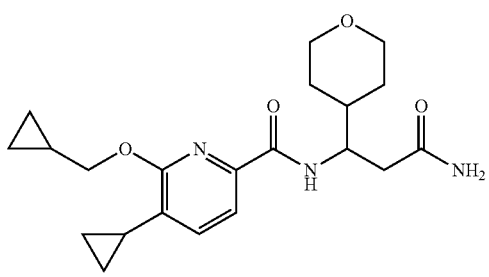 [SMILES: NC(=O)CC(NC(=O)c1ccc(C2CC2)c(OCC2CC2)n1)C1CCOCC1]

The enantiomers of 5-cyclopropyl-6-cyclopropyl-methoxy-pyridine-2-carboxylic acid [2-carbamoyl-1-(tetrahydro-pyran-4-yl)-ethyl]-amide (Example 30) were separated by chiral HPLC (Chiralpak AD, 10% ethanol in n-heptane). The (−)-enantiomer (57 mg, 39%) was isolated as white solid; LC-MS (UV peak area/ESI) 100%, 388.2233 [MH$^+$].

Example 35

5-Cyclopropyl-6-cyclopropylmethoxy-pyridine-2-carboxylic acid ((S)-1-carbamoylmethyl-2,2-dimethyl-propyl)-amide a) (S)-3-Amino-4,4-dimethylpentanamide hydrochloride

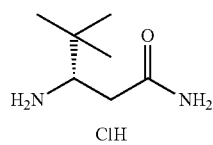

To a solution of (3S)-3-amino-4,4-dimethyl-pentanoic acid methyl ester hydrochloride (1:1) (Astatech 75020, 500 mg, 2.56 mmol) in toluene (8.0 mL) was added ammonium hydroxide in water (25%, 8.0 mL, 51.4 mmol). The mixture was stirred in a closed tube at room temperature for 6 days. Solvents were removed in vacuo and remaining water was removed by azeotropic distillation with toluene. The residue was dried in high-vacuum at 40° C. to give the desired product (530 mg, quant.) as white foam; LC-MS (ESI), 145.1340 [MH$^+$].

b) 5-Cyclopropyl-6-cyclopropylmethoxy-pyridine-2-carboxylic acid ((S)-1-carbamoylmethyl-2,2-dimethyl-propyl)-amide

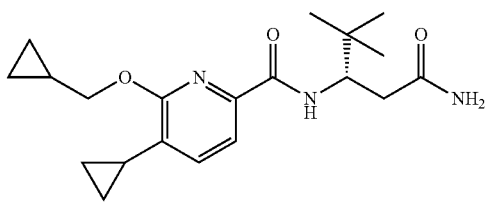

The title compound was synthesized in analogy to Example 1 d), using 5-cyclopropyl-6-cyclopropylmethoxy-pyridine-2-carboxylic acid (Example 1 c, 50 mg, 214 µmol) and (S)-3-amino-4,4-dimethylpentanamide hydrochloride (42.6 mg, 236 µmol) as starting materials and isolated (66 mg, 86%) as white solid; LC-MS (UV peak area, ESI) 98.0%, 360.2279 [MH$^+$].

Example 36

5-Cyclopropyl-6-(2-methyl-propane-1-sulfonyl)-pyridine-2-carboxylic acid (3-carbamoylmethyl-oxetan-3-yl)-amide a) 5-Bromo-6-(isobutylthio)picolinic acid

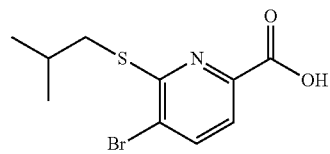

5-Bromo-6-chloropicolinic acid (2 g, 8.46 mmol; CAN 959958-25-9), 2-methylpropane-1-thiol (915 mg, 1.1 mL, 10.2 mmol) and cesium carbonate (6.89 g, 21.1 mmol) were suspended in DMSO (100 mL). The reaction mixture was heated to 150° C. and stirred for 1 d and was poured onto ice-water/1N HCl (100 mL). The aqueous layer was extracted with EtOAc (2×250 mL). The combined extracts were washed with ice-water/brine (100 mL), dried over Na$_2$SO$_4$ and concentrated in vacuo to give the title compound (2.49 g, 51%) as an orange solid which was used in the next step without further purification. MS (EI): m/e=288.4 [M−H]$^−$.

b) Methyl 5-bromo-6-(isobutylthio)picolinate

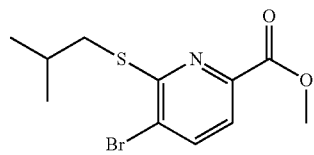 [SMILES: COC(=O)c1ccc(Br)c(SCC(C)C)n1]

5-Bromo-6-(isobutylthio)picolinic acid (500 mg, 1.72 mmol) was dissolved in methanol (5 mL) to give a yellow solution. Sulfuric acid (169 mg, 92.3 µL, 1.72 mmol) was added. The reaction mixture was heated to 80° C. and stirred for 1 d. The reaction mixture was cooled to 0° C. and poured onto ice-water/brine (25 mL). The aqueous layer was extracted with EtOAc (2×40 mL) and washed with ice-water/brine (20 mL). The organic layers were combined, dried over Na$_2$SO$_4$ and concentrated in vacuo to give crude title compound as a yellow oil. The oil was purified by flash chromatography (silica gel, 5 g, 0% to 15% EtOAc in heptane) to give the title product (205 mg, 39%) as a colorless oil. MS (EI): m/e=306.3 [M+H]$^+$.

c) Methyl 5-bromo-6-(isobutylsulfonyl)picolinate

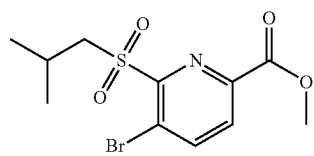 [SMILES: COC(=O)c1ccc(Br)c(S(=O)(=O)CC(C)C)n1]

Methyl 5-bromo-6-(isobutylthio)picolinate (30 mg, 98.6 µmol) was dissolved in dichloromethane (1 mL). The solution was cooled to 0° C. 3-Chlorobenzoperoxoic acid (34.0 mg, 197 µmol) was added. The reaction mixture was stirred for 1 d at ambient temp., poured onto ice-water (20 mL) and extracted with dichloromethane (2×30 mL). The extract was washed with a 10% aqueous Na₂S₂O₃-solution (15 mL). The aqueous layer was back-extracted with dichloromethane (30 mL). The combined organic layers were washed with an aqueous 10% sodium hydrogen carbonate solution, dried over Na₂SO₄ and concentrated in vacuo to give the crude product as a white solid. Filtration through silica gel (3 g, heptane/EtOAc 1:1) provided the title compound (19 mg, 70%) as a white oil. MS (EI): m/e=338.3 [M+H]'.

d) 5-Cyclopropyl-6-(isobutylsulfonyl)picolinic acid

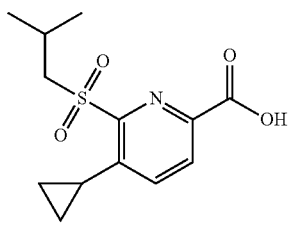 [SMILES: CC(C)CS(=O)(=O)c1nc(C(=O)O)ccc1C1CC1]

The title compound was prepared in analogy to the procedure described in Example 3 c), using methyl 5-bromo-6-(isobutylsulfonyl)picolinate as starting material. MS (EI): m/e=284.3 [M+H]⁺.

e) 5-Cyclopropyl-6-(2-methyl-propane-1-sulfonyl)-pyridine-2-carboxylic acid (3-carbamoylmethyl-oxetan-3-yl)-amide

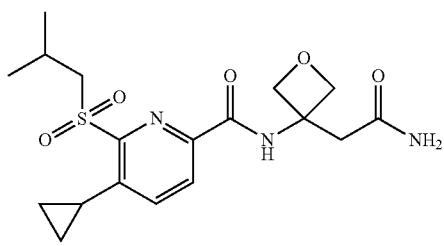 [SMILES: CC(C)CS(=O)(=O)c1nc(C(=O)NC2(CC(N)=O)COC2)ccc1C1CC1]

In analogy to the procedure described in Example 1 d), 5-cyclopropyl-6-(isobutylsulfonyl)picolinic acid was reacted with 2-(3-amino-oxetan-3-yl)-acetamide (Example 23 a)) in the presence of TBTU and DIEA to obtain the title compound as colorless oil; MS (EI): m/e=396.4 [MH⁺].

Example 37

6-Cyclopropylmethoxy-5-(3,3-difluoro-azetidin-1-yl)-pyridine-2-carboxylic acid (3-methylcarbamoyl-methyl-oxetan-3-yl)-amide a) 2-(3-Amino-oxetan-3-yl)-N-methyl-acetamide

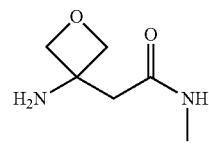

To a solution of 3-amino-3-oxetaneacetic acid ethyl ester (500 mg, 3.14 mmol) in toluene (8.0 mL) was added methanamine in water (40%, 10.0 mL, 116 mmol). The mixture was stirred in a closed tube at room temperature for 7 days. Solvents were removed in vacuo and remaining water was removed by azeotropic distillation with toluene. The residue was dried in high-vacuum at 40° C. to give the desired product (440 mg, 97%) as white solid; LC-MS (ESI), 145.0973 [MH⁺].

b) 6-Cyclopropylmethoxy-5-(3,3-difluoro-azetidin-1-yl)-pyridine-2-carboxylic acid (3-methylcarbam-oylmethyl-oxetan-3-yl)-amide

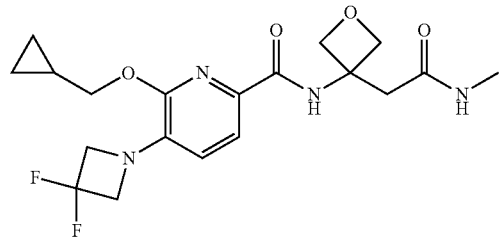 [SMILES: CNC(=O)CC1(NC(=O)c2ccc(N3CC(F)(F)C3)c(OCC3CC3)n2)COC1]

The title compound was synthesized in analogy to Example 1 d), using 6-cyclopropylmethoxy-5-(3,3-difluoro-azetidin-1-yl)-pyridine-2-carboxylic acid (Example 2 b, 50 mg, 176 µmol) and 2-(3-amino-oxetan-3-yl)-N-methyl-acetamide (Example 37 a, 27.9 mg, 193 µmol) as starting materials and isolated (55 mg, 76%) as white solid; LC-MS (UV peak area, ESI) 100%, 411.1834 [MH⁺].

Example 38

5-Cyclopropyl-6-cyclopropylmethoxy-pyridine-2-carboxylic acid (3-methylcarbamoylmethyl-oxetan-3-yl)-amide

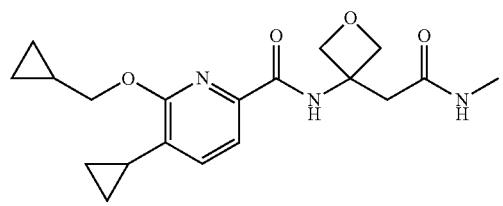 [SMILES: CNC(=O)CC1(NC(=O)c2ccc(C3CC3)c(OCC3CC3)n2)COC1]

The title compound was synthesized in analogy to Example 1 d), using 5-cyclopropyl-6-cyclopropylmethoxy-pyridine-2-carboxylic acid (Example 1 c, 50 mg, 214 µmol) and 2-(3-amino-oxetan-3-yl)-N-methyl-acetamide (Example 37 a, 34.0 mg, 236 µmol) as starting materials and isolated (63 mg, 82%) as white solid; LC-MS (UV peak area, ESI) 98.8%, 360.1918 [MH$^+$].

Example 39

6-Cyclopropylmethoxy-5-trifluoromethyl-pyridine-2-carboxylic acid (3-methylcarbamoylmethyl-oxetan-3-yl)-amide a) 5-(Trifluoromethyl)-pyridine-2-carboxylic acid methyl ester

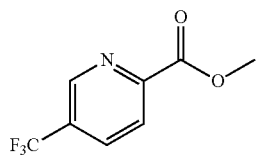

A solution of 5-(trifluoromethyl)-pyridine-2-carboxylic acid (CAN 80194-69-0, 3 g, 15.7 mmol) and sulfurous dichloride (0.1 mL) in methanol (30 mL) was stirred under reflux conditions overnight. Removal of the solvent provided the crude title compound which was purified by column chromatography (silica gel, 20 g, 10% ethyl acetate in petroleum ether) to obtain the title compound (2.7 g, 84%) as white solid; MS (EI): m/e=206.1 [MH$^+$].

b) 1-Oxy-5-trifluoromethyl-pyridine-2-carboxylic acid methyl ester

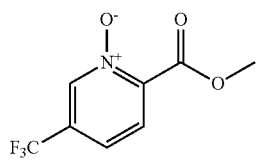

A mixture of 5-(trifluoromethyl)-pyridine-2-carboxylic acid methyl ester (2.7 g, 13 mmol) and m-CPBA (CAN 937-14-4, 6.7 g, 39 mmol) in dry methylene chloride (30 mL) was stirred under reflux conditions overnight. Removal of the solvent in vacuo and purification of the obtained residue by column chromatography (silica gel, 15 g, 20% ethyl acetate in petroleum ether) provided the title compound (2.2 g, 76%) as light-yellow solid; MS (EI): m/e=222.1 [MH$^+$].

c) 6-Chloro-5-(trifluoromethyl)-pyridine-2-carboxylic acid methyl ester

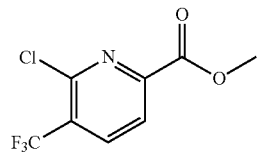

1-Oxy-5-trifluoromethyl-pyridine-2-carboxylic acid methyl ester (2.2 g, 10 mmol) was added in portions to phosphoryl trichloride (CAN 10025-87-3, 10 mL) at 0° C. and the resulting mixture was stirred at 50° C. overnight. Removal of the solvent in vacuo gave a brown oil which was dissolved in ethyl acetate (30 mL) and carefully neutralized with a aqueous solution of sodium carbonate. The mixture was extracted with ethyl acetate (2×30 mL) and the combined organic phase was washed with brine (30 mL), dried over anhydrous sodium sulfate, filtered and concentrated to give a light-brown solid. The solid was purified by column chromatography (silica gel, 15 g, 3% ethyl acetate in petroleum ether) to give the target compound (1.5 g, 63%) as white solid; MS (EI): m/e=240.0 [MH$^+$].

d) 6-Cyclopropylmethoxy-5-trifluoromethyl-pyridine-2-carboxylic acid

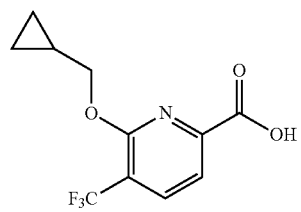 [SMILES: O=C(O)c1ccc(C(F)(F)F)c(OCC2CC2)n1]

Sodium hydride (1.1 g, 31.4 mmol) was added in portions to cyclopropylmethanol (20 mL) and the mixture was stirred at room temperature for 0.5 hours. 6-Chloro-5-(trifluoromethyl)-pyridine-2-carboxylic acid methyl ester (1.5 g, 6.3 mmol) was added and the resulting solution was stirred at 80° C. for 1 h. Water (20 mL) was added; the solution was acidified with 6 N hydrochloric acid and then concentrated to give a residue which was partitioned between water (30 mL) and ethyl acetate (20 mL). The aqueous solution was extracted with ethyl acetate (2×20 mL) and the combined organic phase was washed with brine (20 mL), dried over anhydrous sodium sulfate, filtered and concentrated to give the crude target compound. The crude target compound was purified by column chromatography (silica gel, 10 g, 15% ethyl acetate in petroleum ether) to give the title compound (1.4 g, 85%) as white solid; MS (EI): m/e=262.0 [MH$^+$].

d) 6-Cyclopropylmethoxy-5-trifluoromethyl-pyridine-2-carboxylic acid (3-methylcarbamoylmethyl-oxetan-3-yl)-amide

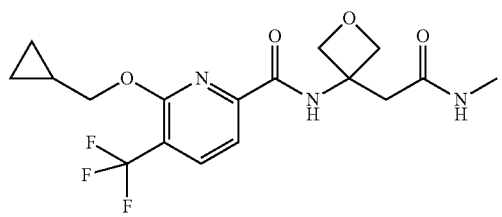 [SMILES: CNC(=O)CC1(NC(=O)c2ccc(C(F)(F)F)c(OCC3CC3)n2)COC1]

The title compound was synthesized in analogy to Example 1 d), using 6-cyclopropylmethoxy-5-trifluoromethyl-pyridine-2-carboxylic acid (Example 39 d, 50 mg, 191 µmol) and 2-(3-amino-oxetan-3-yl)-N-methyl-acetamide (Example 37 a, 30.4 mg, 211 µmol) as starting materials and isolated (51 mg, 69%) as white solid; LC-MS (UV peak area, ESI) 100%, 388.1478 [MH+].

Example 40

5-Cyclopropyl-6-cyclopropylmethoxy-pyridine-2-carboxylic acid (3-dimethylcarbamoylmethyl-oxetan-3-yl)-amide a) 2-(3-Amino-oxetan-3-yl)-N,N-dimethyl-acetamide

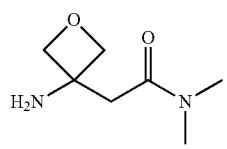

To a solution of 3-amino-3-oxetaneacetic acid ethyl ester (470 mg, 2.95 mmol) in toluene (8.0 mL) was added dimethylamine in water (40%, 10.0 mL, 79 mmol). The mixture was stirred in a closed tube at room temperature for 7 days. Solvents were removed in vacuo and remaining water was removed by azeotropic distillation with toluene. The residue was dried in high-vacuum at 40° C. to give the desired product (405 mg, 87%) as white solid; LC-MS (ESI), 159.1131 [MH+].

b) 5-Cyclopropyl-6-cyclopropylmethoxy-pyridine-2-carboxylic acid (3-dimethylcarbamoylmethyl-oxetan-3-yl)-amide

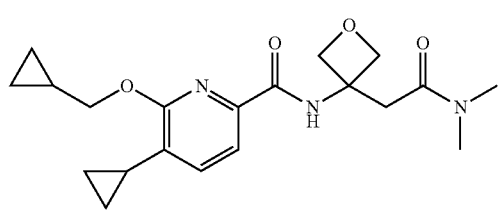 [SMILES: CN(C)C(=O)CC1(NC(=O)c2ccc(C3CC3)c(OCC3CC3)n2)COC1]

The title compound was synthesized in analogy to Example 1 d), using 5-cyclopropyl-6-cyclopropylmethoxy-pyridine-2-carboxylic acid (Example 1 c, 50 mg, 214 µmol) and 2-(3-amino-oxetan-3-yl)-N,N-dimethyl-acetamide (Example 40 a, 67.8 mg, 429 µmol) as starting materials and isolated (33 mg, 41%) as white solid; LC-MS (UV peak area, ESI) 100%, 374.2065 [MH+].

Example 41

6-Cyclopropylmethoxy-5-(3,3-difluoro-azetidin-1-yl)-pyridine-2-carboxylic acid (3-dimethylcarbamoylmethyl-oxetan-3-yl)-amide

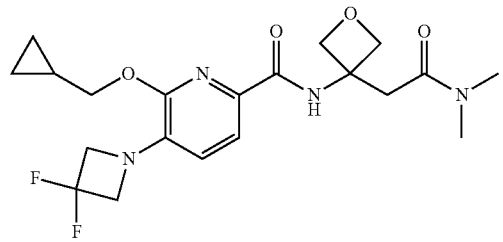 [SMILES: CN(C)C(=O)CC1(NC(=O)c2ccc(N3CC(F)(F)C3)c(OCC3CC3)n2)COC1]

Example 42

6-Cyclopropylmethoxy-5-trifluoromethyl-pyridine-2-carboxylic acid (3-dimethylcarbamoylmethyl-oxetan-3-yl)-amide

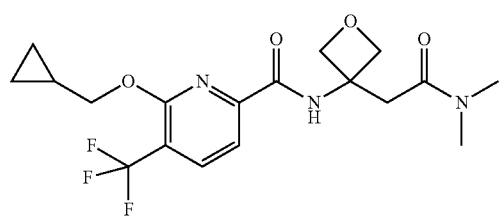 [SMILES: CN(C)C(=O)CC1(NC(=O)c2ccc(C(F)(F)F)c(OCC3CC3)n2)COC1]

The title compound was synthesized in analogy to Example 1 d), using 6-cyclopropylmethoxy-5-trifluoromethyl-pyridine-2-carboxylic acid (Example 39 d, 50 mg, 191 µmol) and 2-(3-amino-oxetan-3-yl)-N,N-dimethyl-acetamide (Example 40 a, 60.6 mg, 383 µmol) as starting materials and isolated (15 mg, 20%) as white solid; LC-MS (UV peak area, ESI) 100%, 402.1634 [MH+].

Example 43

5-Cyclopropyl-6-cyclopropylmethoxy-pyridine-2-carboxylic acid [(R)-2-carbamoyl-1-(3-chloro-phenyl)-ethyl]-amide

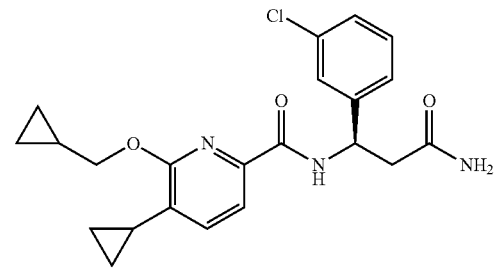 [SMILES: NC(=O)C[C@@H](NC(=O)c1ccc(C2CC2)c(OCC2CC2)n1)c1cccc(Cl)c1]

The title compound was synthesized in analogy to Example 1 d), using 5-cyclopropyl-6-cyclopropylmethoxy-pyridine-2-carboxylic acid (Example 1 c, 50 mg, 214 µmol) and (βR)-β-amino-3-chloro-benzenepropanamide hydrochloride (1:1) (CAN 1376000-87-1, 58.4 mg, 236 µmol) as starting materials and isolated (75 mg, 85%) as white solid; LC-MS (UV peak area, ESI) 100%, 414.1581 [MH⁺].

Example 44

5-Bromo-6-(propane-2-sulfinyl)-pyridine-2-carboxylic acid (3-carbamoylmethyl-oxetan-3-yl)-amide a) 5-Bromo-6-(isopropylthio)picolinic acid

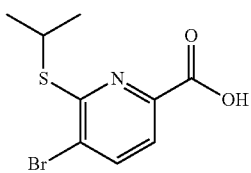

In analogy to the procedure described in Example 36 a), 5-bromo-6-chloropicolinic acid (CAN 959958-25-9) was reacted with propane-2-thiol (CAN 75-33-2) to give the title compound as yellow solid.

b) Methyl 5-bromo-6-(isopropylthio)picolinate

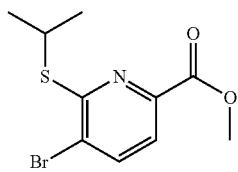

In analogy to the procedure described in Example 36 b), 5-bromo-6-(isopropylthio)picolinic acid was esterified in the presence of sulfuric acid to give the title compound as yellow oil.

c) Methyl 5-bromo-6-(isopropylsulfinyl)picolinate

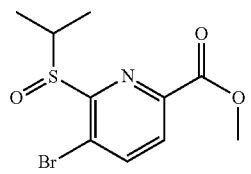 [SMILES: COC(=O)c1ccc(Br)c(S(=O)C(C)C)n1]

In analogy to the procedure described in Example 36 c), methyl 5-bromo-6-(isopropylthio)picolinate was oxidized with 3-chlorobenzoperoxoic acid to give the title compound as white solid; MS (EI): m/e=308.2 [MH⁺].

d) 5-Bromo-6-(isopropylsulfinyl)picolinic acid

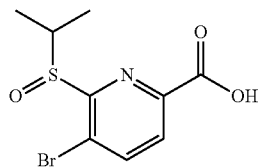

A solution of methyl 5-bromo-6-(isopropylsulfinyl)picolinate (200 mg, 653 µmol) and lithium hydroxide hydrate (30.2 mg, 719 µmol) in THF (1 mL) and water (0.2 mL) was stirred at ambient temperature for 20 h. Under ice cooling a 4 M solution of HCl in dioxane (196 µL, 784 µmol) was added and the mixture was evaporated to dryness to give the title compound (241 mg, quant.) as white solid which used in the next reaction step without further purification; MS (EI): m/e=292.3 [M–H⁻].

e) 5-Bromo-6-(propane-2-sulfinyl)-pyridine-2-carboxylic acid (3-carbamoylmethyl-oxetan-3-yl)-amide

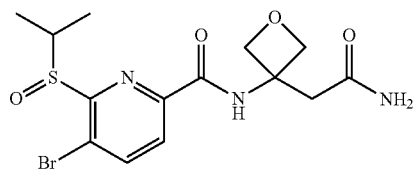 [SMILES: CC(C)S(=O)c1nc(C(=O)NC2(CC(N)=O)COC2)ccc1Br]

In analogy to the procedure described in Example 1 d), 5-bromo-6-(isopropylsulfinyl)picolinic acid was reacted with 2-(3-amino-oxetan-3-yl)-acetamide (Example 23 a)) in the presence of TBTU and DIEA to obtain the title compound as colorless oil; MS (EI): m/e=406.3 [MH⁺].

Example 45

4-[(5-Cyclopropyl-6-cyclopropylmethoxy-pyridine-2-carbonyl)-amino]-4-methoxycarbonylmethyl-piperidine-1-carboxylic acid tert-butyl ester

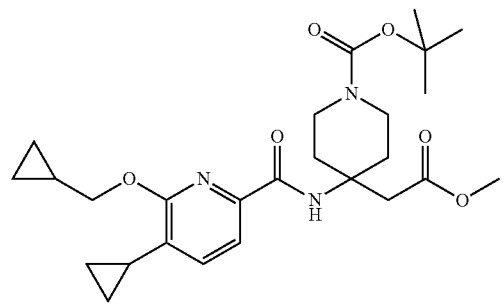 [SMILES: COC(=O)CC1(NC(=O)c2ccc(C3CC3)c(OCC3CC3)n2)CCN(C(=O)OC(C)(C)C)CC1]

The title compound was synthesized in analogy to Example 1 d), using 5-cyclopropyl-6-cyclopropylmethoxy-pyridine-2-carboxylic acid (Example 1 c, 70 mg, 300 µmol) and 4-amino-1-[(1,1-dimethylethoxy)carbonyl]-4-piperidineacetic acid methyl ester (CAN 362703-57-9, 58.4 mg, 330 µmol) as starting materials and isolated (74 mg, 51%) as colorless oil; LC-MS (UV peak area, ESI) 100%, 488.2756 [MH⁺].

Example 46

6-Cyclopropylmethoxy-5-trifluoromethoxy-pyridine-2-carboxylic acid (3-carbamoylmethyl-oxetan-3-yl)-amide a) Mixture of 6-cyclopropylmethoxy-5-trifluoromethoxy-pyridine-2-carboxylic acid and 6-chloro-5-cyclopropylmethoxy-pyridine-2-carboxylic acid

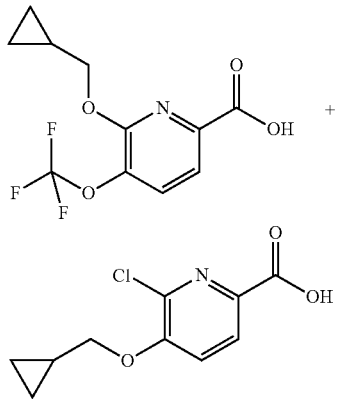

To a solution of 6-chloro-5-trifluoromethoxy-pyridine-2-carboxylic acid (CAN 1221171-90-9, 1.0 g, 4.14 mmol) in DMSO (16 mL) was added potassium hydroxide (0.93 g, 16.6 mmol) and the reaction mixture was stirred at room temperature for 15 minutes. To this suspension was added cyclopropylmethanol (335 µL, 4.14 mmol) and the mixture was stirred at ambient temperature for 16 hours. More cyclopropylmethanol (335 µL, 4.14 mmol) was added and stirring continued for 4 hours at 50° C. The mixture was cooled, added to 2 N sodium hydroxide solution (50 mL) with cooling and partitioned between TBME and 1 N sodium hydroxide solution. The organic phase was discarded; the water phases were pooled, acidified with 2 N hydrochloric acid and extracted with TBME. Organic phases were pooled, dried with $Na_2SO_4$, filtered and concentrated in vacuo. The crude material (1.05 g) of a light brown solid was used without and contained a mixture of 6-cyclopropylmethoxy-5-trifluoromethoxy-pyridine-2-carboxylic acid and 6-chloro-5-cyclopropylmethoxy-pyridine-2-carboxylic acid (~7/3 by NMR); LC-MS (UV peak area, ESI) 48.8%, 228.0425 [MH$^+$], 51.2%, 278.0628 [MH$^+$].

b) 6-Cyclopropylmethoxy-5-trifluoromethoxy-pyridine-2-carboxylic acid (3-carbamoylmethyl-oxetan-3-yl)-amide

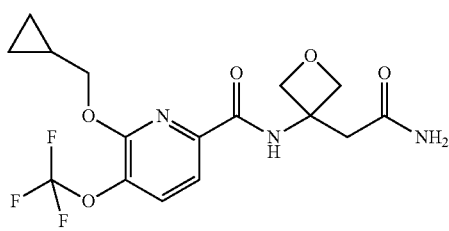 [SMILES: NC(=O)CC1(NC(=O)c2ccc(OC(F)(F)F)c(OCC3CC3)n2)COC1]

The title compound was synthesized in analogy to Example 1 d), using the mixture of 6-cyclopropylmethoxy-5-trifluoromethoxy-pyridine-2-carboxylic acid and 6-chloro-5-cyclopropylmethoxy-pyridine-2-carboxylic acid (Example 46 a, 50 mg, 180 µmol) and 2-(3-amino-oxetan-3-yl)-acetamide (Example 23 a, 25.8 mg, 198 µmol) as starting materials and isolated (31 mg, 44%) as white solid; LC-MS (UV peak area, ESI) 100%, 390.1269 [MH$^+$].

Example 47

6-Chloro-5-cyclopropylmethoxy-pyridine-2-carboxylic acid (3-carbamoylmethyl-oxetan-3-yl)-amide

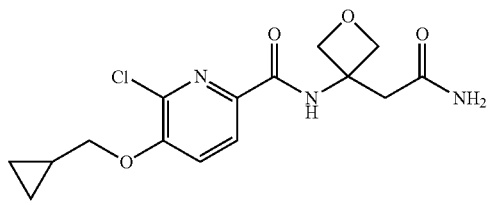 [SMILES: NC(=O)CC1(NC(=O)c2ccc(OCC3CC3)c(Cl)n2)COC1]

The title compound was synthesized in analogy to Example 1 d), using the mixture of 6-cyclopropylmethoxy-5-trifluoromethoxy-pyridine-2-carboxylic acid and 6-chloro-5-cyclopropylmethoxy-pyridine-2-carboxylic acid (Example 46 a, 50 mg, 180 µmol) and 2-(3-amino-oxetan-3-yl)-acetamide (Example 23 a, 25.8 mg, 198 µmol) as starting materials and isolated (9 mg, 15%) as white solid; LC-MS (UV peak area, ESI) 100%, 340.1056 [MH$^+$].

Example 48

6-Cyclopropylmethoxy-5-(3,3-difluoro-azetidin-1-yl)-pyridine-2-carboxylic acid (2-carbamoyl-1,1-dimethyl-ethyl)-amide

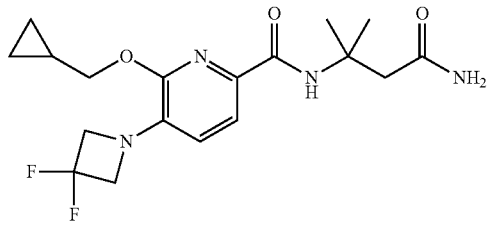 [SMILES: CC(C)(CC(N)=O)NC(=O)c1ccc(N2CC(F)(F)C2)c(OCC2CC2)n1]

The title compound was synthesized in analogy to Example 1 d), using 6-cyclopropylmethoxy-5-(3,3-difluoroazetidin-1-yl)-pyridine-2-carboxylic acid (Example 2 b, 50 mg, 176 µmol) and 3-amino-3-methyl-butanamide hydrochloride (1:1) (CAN 173337-04-7, 29.5 mg, 193 µmol) as starting materials and isolated (64 mg, 65%) as white solid; LC-MS (UV peak area, ESI) 100%, 383.1901 [MH⁺].

Example 49

5-Cyclopropyl-6-(2,2,3,3,3-pentafluoro-propoxy)-pyridine-2-carboxylic acid (3-carbamoylmethyl-oxetan-3-yl)-amide a) 5-Bromo-6-(2,2,3,3,3-pentafluoro-propoxy)-pyridine-2-carboxylic acid

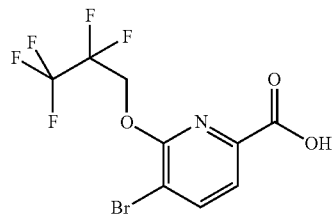 [SMILES: O=C(O)c1ccc(Br)c(OCC(F)(F)C(F)(F)F)n1]

To a solution of 6-chloro-5-bromo-pyridine-2-carboxylic acid (CAN 959958-25-9, 1.7 g, 7.19 mmol) in DMF (90 mL) and THF (30 mL) was added potassium tert-butoxide (2.02 g, 18.0 mmol) and 2,2,3,3,3-pentafluoropropan-1-ol (5.73 mL, 57.5 mmol). The mixture was stirred at 140° C. for 4 days, cooled and poured into ice-water (100 mL). 2 M Hydrochloric acid (15 mL) was added to adjust the pH to 2-3 and the mixture was extracted with TBME, organic layers were washed twice with water, pooled, dried with Na₂SO₄, filtered and concentrated in vacuo. The crude material was purified by flash chromatography (silica gel, ethyl acetate/n-heptane gradient) to give the title compound (548 mg, 22%) as light-brown solid; LC-MS (UV peak area, ESI) 100%, 347.9306 [M−H⁻].

b) 5-Cyclopropyl-6-(2,2,3,3,3-pentafluoro-propoxy)-pyridine-2-carboxylic acid

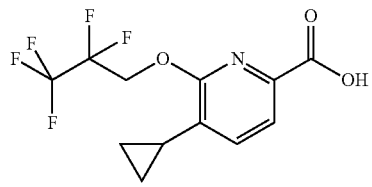 [SMILES: O=C(O)c1ccc(C2CC2)c(OCC(F)(F)C(F)(F)F)n1]

A mixture of 5-bromo-6-(2,2,3,3,3-pentafluoro-propoxy)-pyridine-2-carboxylic acid (501 mg, 1.43 mmol), cyclopropylboronic acid (CAN 411235-57-9, 184 mg, 2.15 mmol), palladium diacetate (CAN 3375-31-3, 16.1 mg, 71.6 µmol), tricyclohexylphosphine (CAN 2622-14-2, 8.03 mg, 28.6 µmol) and potassium phosphate (1.06 g, 5.01 mmol) in toluene/water (20/1 v/v, 10.5 mL) was stirred at 100° C. for 22 hours. After cooling the mixture was poured into ice-water (80 mL). 2 M Hydrochloric acid (25 mL) was added and the mixture was extracted with TBME, organic layers were washed twice with water, pooled, dried with Na₂SO₄, filtered and concentrated in vacuo. The crude material was purified by flash chromatography (silica gel, ethyl acetate/n-heptane gradient) to give the title compound (340 mg, 76%) as off-white solid; LC-MS (UV peak area, ESI) 96.6%, 310.0513 [M−H⁻].

c) 5-Cyclopropyl-6-(2,2,3,3,3-pentafluoro-propoxy)-pyridine-2-carboxylic acid (3-carbamoylmethyl-oxetan-3-yl)-amide

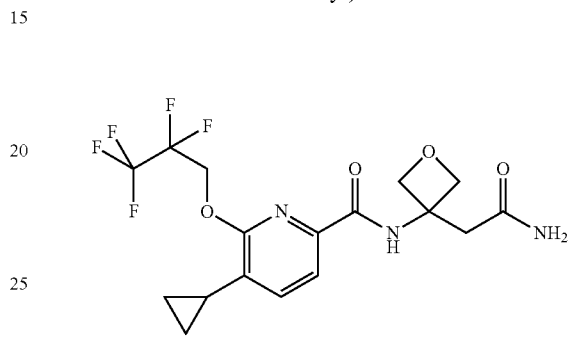

The title compound was synthesized in analogy to Example 1 d), using 5-cyclopropyl-6-(2,2,3,3,3-pentafluoro-propoxy)-pyridine-2-carboxylic acid (Example 49 b, 40 mg, 129 mol) and 2-(3-amino-oxetan-3-yl)-acetamide (Example 23 a, 18.0 mg, 141 µmol) as starting materials and isolated (29 mg, 53%) as white solid; LC-MS (UV peak area, ESI) 95%, 424.1300 [MH⁺].

Example 50

(3-{[6-Cyclopropylmethoxy-5-(3,3-difluoro-azetidin-1-yl)-pyridine-2-carbonyl]-amino}-5-oxo-pyrrolidin-3-yl)-acetic acid methyl ester

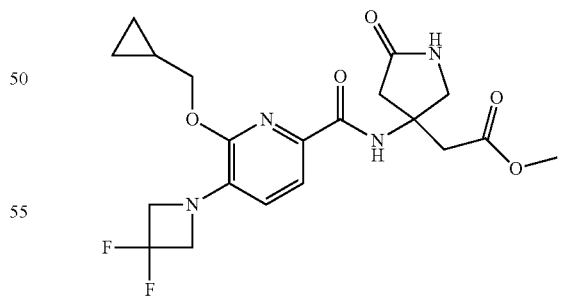

In analogy to the procedure described in Example 1 d), 6-cyclopropylmethoxy-5-(3,3-difluoro-azetidin-1-yl)-pyridine-2-carboxylic acid (Example 2 b)) was reacted with methyl 2-(3-amino-5-oxopyrrolidin-3-yl)acetate (CAN 362706-49-8) in the presence of TBTU and DIEA to obtain the title compound as light yellow oil; MS (EI): m/e=439.5 [MH⁺].

Example 51

(3-{[6-Cyclopropylmethoxy-5-(3,3-difluoro-azetidin-1-yl)-pyridine-2-carbonyl]-amino}-1,1-dioxo-1λ6-thietan-3-yl)-acetic acid ethyl ester a) Ethyl 2-(3-(benzylamino)thietan-3-yl)acetate

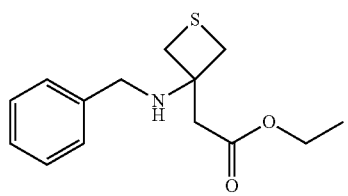 [SMILES: CCOC(=O)CC1(NCc2ccccc2)CSC1]

A mixture of ethyl 2-(thietan-3-ylidene)acetate (CAN 1223573-30-5, 1.8 g, 11.4 mmol) and phenylmethanamine (CAN 100-46-9, 1.22 g, 1.24 mL, 11.4 mmol) was stirred for 14 h at ambient temperature. The crude material was purified by flash chromatography (silica gel, 70 g, 0% to 20% EtOAc in heptane) to give the title compound (2.4 g, 80%) as light yellow liquid; MS (EI): m/e=266.5 [MH$^+$].

b) (3-Benzylamino-1,1-dioxo-1λ6-thietan-3-yl)-acetic acid ethyl ester

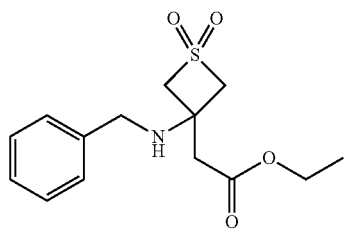 [SMILES: CCOC(=O)CC1(NCc2ccccc2)CS(=O)(=O)C1]

To a solution of ethyl 2-(3-(benzylamino)thietan-3-yl)acetate (1.5 g, 5.65 mmol) in DCM (100 mL) was added titanium(IV) isopropoxide (1.61 g, 1.67 mL, 5.65 mmol) and the solution was cooled to 0° C. Hydrogen peroxide 30% in H$_2$O (577 mg, 577 µL, 17.0 mmol) was added and the mixture stirred vigorously for 40 min at 0° C., then more hydrogen peroxide 30% in H$_2$O (192 mg, 192 µL, 5.65 mmol) was added. The mixture was stirred for 10 min, the ice bath was removed and stirring was continued for a further 1 h at ambient temperature. Hydrogen peroxide 30% in H$_2$O (192 mg, 192 µL, 5.65 mmol) was again added and the mixture stirred overnight. The yellow suspension was filtered. Ice-water was added to the filtrate and the solution was extracted four times with DCM. The organic phases were combined, dried over Na$_2$SO$_4$, and concentrated in vacuo to give a light yellow oil which was purified by flash chromatography (silica gel, 70 g, 20% to 40% EtOAc in heptane) to give the title compound (1.09 g, 65%) as white solid; MS (EI): m/e=298.4 [MH$^+$].

c) (3-Amino-1,1-dioxo-1λ6-thietan-3-yl)-acetic acid ethyl ester

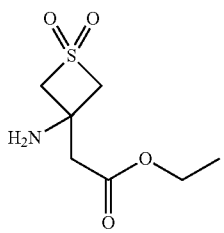

10% Palladium on charcoal (80 mg, 75.2 µmol) was added to a solution of (3-benzylamino-1,1-dioxo-1λ6-thietan-3-yl)-acetic acid ethyl ester (403 mg, 1.36 mmol) in methanol (12 mL) under a hydrogen atmosphere. The reaction mixture was stirred at a hydrogen gas pressure of 4 bar at 30° C. for 24 h. The catalyst was filtered off and washed with methanol. The filtrate was brought to dryness to give the title compound (251 mg, 89%) as yellow solid which was used in the next step without further purification; MS (EI): m/e=208.2 [MH$^+$].

d) (3-{[6-Cyclopropylmethoxy-5-(3,3-difluoro-azetidin-1-yl)-pyridine-2-carbonyl]-amino}-1,1-dioxo-1λ6-thietan-3-yl)-acetic acid ethyl ester

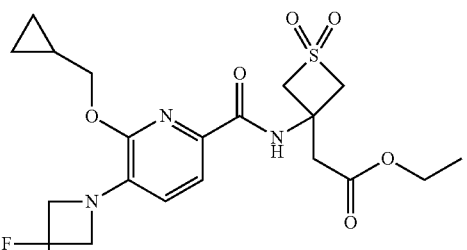

In analogy to the procedure described in Example 1 d), 6-cyclopropylmethoxy-5-(3,3-difluoro-azetidin-1-yl)-pyridine-2-carboxylic acid (Example 2 b)) was reacted with (3-amino-1,1-dioxo-1λ6-thietan-3-yl)-acetic acid ethyl ester in the presence of TBTU and DIEA to obtain the title compound as yellow oil; MS (EI): m/e=474.4 [MH$^+$].

Example 52

(4-{[6-Cyclopropylmethoxy-5-(3,3-difluoro-azetidin-1-yl)-pyridine-2-carbonyl]-amino}-tetrahydro-pyran-4-yl)-acetic acid methyl ester

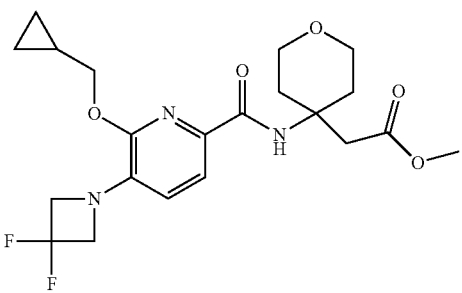 [SMILES: COC(=O)CC1(NC(=O)c2ccc(N3CC(F)(F)C3)c(OCC3CC3)n2)CCOCC1]

In analogy to the procedure described in Example 1 d), 6-cyclopropylmethoxy-5-(3,3-difluoro-azetidin-1-yl)-pyridine-2-carboxylic acid (Example 2 b)) was reacted with methyl 2-(4-aminotetrahydro-2H-pyran-4-yl)acetate hydrochloride (CAN 303037-37-8) in the presence of TBTU and DIEA to obtain the title compound as yellow oil; MS (EI): m/e=440.5 [MH⁺].

Example 53

6-Cyclopropylmethoxy-5-(3,3-difluoro-azetidin-1-yl)-pyridine-2-carboxylic acid [2-carbamoyl-1-(tetrahydro-pyran-4-yl)-ethyl]-amide

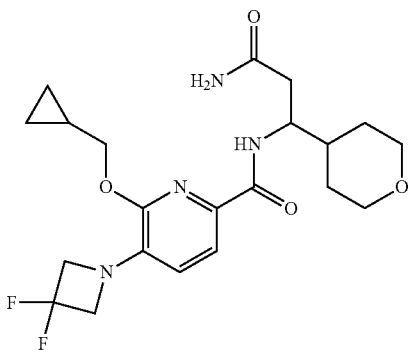 [SMILES: NC(=O)CC(NC(=O)c1ccc(N2CC(F)(F)C2)c(OCC2CC2)n1)C1CCOCC1]

In analogy to the procedure described in Example 1 d), 6-cyclopropylmethoxy-5-(3,3-difluoro-azetidin-1-yl)-pyridine-2-carboxylic acid (Example 2 b)) was reacted with 3-amino-3-(tetrahydro-2H-pyran-4-yl)propanamide (CAN 1250074-10-2) in the presence of TBTU and DIEA to obtain the title compound as colorless solid; MS (EI): m/e=439.5 [MH⁺].

Example 54

6-Cyclopropylmethoxy-5-(3,3-difluoro-azetidin-1-yl)-pyridine-2-carboxylic acid (3-carbamoylmethyl-5-oxo-pyrrolidin-3-yl)-amide a) 2-(3-(6-(Cyclopropylmethoxy)-5-(3,3-difluoro-azetidin-1-yl)picolinamido)-5-oxopyrrolidin-3-yl) acetic acid

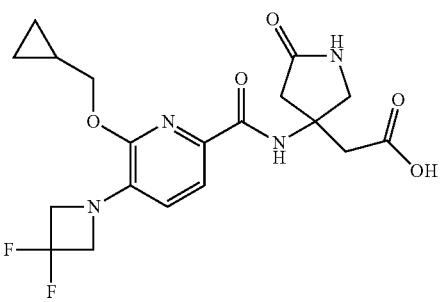 [SMILES: O=C(O)CC1(NC(=O)c2ccc(N3CC(F)(F)C3)c(OCC3CC3)n2)CNC(=O)C1]

In analogy to the procedure described in Example 6 a), (3-{[6-cyclopropylmethoxy-5-(3,3-difluoro-azetidin-1-yl)-pyridine-2-carbonyl]-amino}-5-oxo-pyrrolidin-3-yl)-acetic acid methyl ester (Example 50) was saponified with lithium hydroxide to give the title compound as colorless oil; MS (EI): m/e=425.6 [MH⁺].

b) 6-Cyclopropylmethoxy-5-(3,3-difluoro-azetidin-1-yl)-pyridine-2-carboxylic acid (3-carbamoylmethyl-5-oxo-pyrrolidin-3-yl)-amide

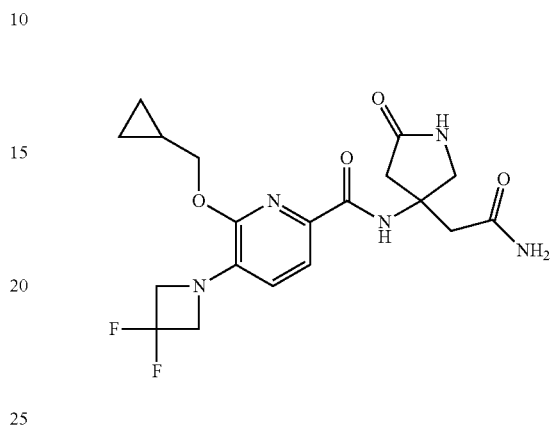

To an ice-cold solution of 2-(3-(6-(cyclopropylmethoxy)-5-(3,3-difluoroazetidin-1-yl)picolinamido)-5-oxopyrrolidin-3-yl)acetic acid (15 mg, 35.3 μmol) in DMF (2 mL) was added carbonyldiimidazole (16 mg, 99 μmol). After 5 minutes the reaction mixture was warmed to ambient temperature and stirred for 2 h. NH₃ gas was bubbled through the solution for 10 minutes and stirring was continued for 14 h. The reaction mixture was poured onto ice-water (20 mL) and extracted with EtOAc (2×20 mL). The combined extracts were dried over Na₂SO₄ and concentrated in vacuo to give an off-white solid. The crude product was purified by preparative HPLC to give the title compound (15 mg, 33%) as white solid; MS (EI): m/e=424.5 [MH⁺].

Example 55

6-Cyclopropylmethoxy-5-(3,3-difluoro-azetidin-1-yl)-pyridine-2-carboxylic acid (1-carbamoylmethyl-2,2,2-trifluoro-ethyl)-amide

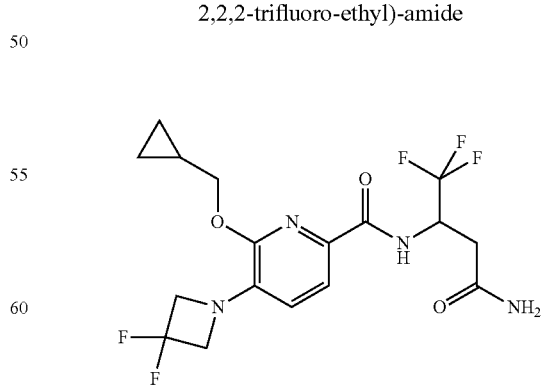

In analogy to the procedure described in Example 1 d), 6-cyclopropylmethoxy-5-(3,3-difluoro-azetidin-1-yl)-pyridine-2-carboxylic acid (Example 2 b)) was reacted with 3-amino-4,4,4-trifluorobutanamide (CAN 453-32-7) in the presence of TBTU and DIEA to obtain the title compound as colorless solid; MS (EI): m/e=423.5 [MH+].

Example 56

(3-{[6-Cyclopropylmethoxy-5-(3,3-difluoro-azetidin-1-yl)-pyridine-2-carbonyl]-amino}-1,1-dioxo-1λ6-thietan-3-yl)-acetic acid

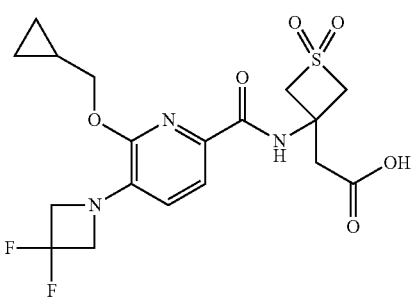 [SMILES: O=C(O)CC1(NC(=O)c2ccc(N3CC(F)(F)C3)c(OCC3CC3)n2)CS(=O)(=O)C1]

In analogy to the procedure described in Example 6 a), (3-{[6-cyclopropylmethoxy-5-(3,3-difluoro-azetidin-1-yl)-pyridine-2-carbonyl]-amino}-1,1-dioxo-1λ6-thietan-3-yl)-acetic acid ethyl ester (Example 51 d)) was saponified with lithium hydroxide to give the title compound as off-white solid; MS (EI): m/e=446.4 [MH+].

Example 57

(4-{[6-Cyclopropylmethoxy-5-(3,3-difluoro-azetidin-1-yl)-pyridine-2-carbonyl]-amino}-tetrahydro-pyran-4-yl)-acetic acid

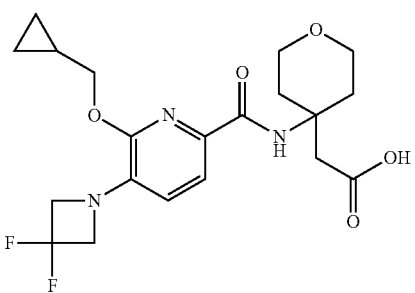 [SMILES: O=C(O)CC1(NC(=O)c2ccc(N3CC(F)(F)C3)c(OCC3CC3)n2)CCOCC1]

In analogy to the procedure described in Example 6 a), (4-{[6-cyclopropylmethoxy-5-(3,3-difluoro-azetidin-1-yl)-pyridine-2-carbonyl]-amino}-tetrahydro-pyran-4-yl)-acetic acid methyl ester (Example 52) was saponified with lithium hydroxide to give the title compound as light yellow oil; MS (EI): m/e=426.5 [MH+].

Example 58

(−)-6-Cyclopropylmethoxy-5-(3,3-difluoro-azetidin-1-yl)-pyridine-2-carboxylic acid [2-carbamoyl-1-(tetrahydro-pyran-4-yl)-ethyl]-amide

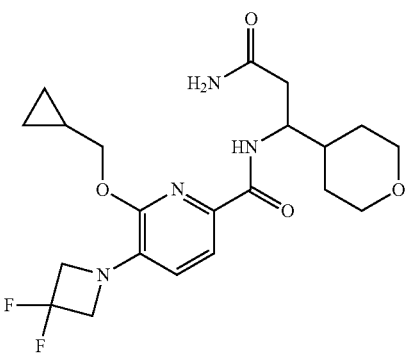

The enantiomers of 6-cyclopropylmethoxy-5-(3,3-difluoro-azetidin-1-yl)-pyridine-2-carboxylic acid [2-carbamoyl-1-(tetrahydro-pyran-4-yl)-ethyl]-amide (Example 53) were separated by chiral HPLC (Reprosil Chiral NR, 40% ethanol in n-heptane). The (−) enantiomer (9 mg, 19%) was isolated as colorless solid; MS (EI): m/e=439.5 [MH+].

Example 59

(+)-6-Cyclopropylmethoxy-5-(3,3-difluoro-azetidin-1-yl)-pyridine-2-carboxylic acid [2-carbamoyl-1-(tetrahydro-pyran-4-yl)-ethyl]-amide

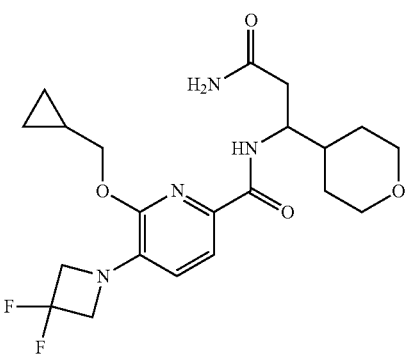 [SMILES: NC(=O)CC(NC(=O)c1ccc(N2CC(F)(F)C2)c(OCC2CC2)n1)C1CCOCC1]

The enantiomers of 6-cyclopropylmethoxy-5-(3,3-difluoro-azetidin-1-yl)-pyridine-2-carboxylic acid [2-carbamoyl-1-(tetrahydro-pyran-4-yl)-ethyl]-amide (Example 53) were separated by chiral HPLC (Reprosil Chiral NR, 40% ethanol in n-heptane). The (+) enantiomer (9 mg, 19%) was isolated as colorless solid; MS (EI): m/e=439.5 [MH⁺].

Example 60

6-Cyclopropylmethoxy-5-(3,3-difluoro-azetidin-1-yl)-pyridine-2-carboxylic acid (4-carbamoylmethyl-tetrahydro-pyran-4-yl)-amide

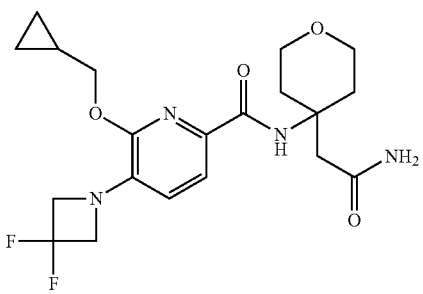 [SMILES: NC(=O)CC1(NC(=O)c2ccc(N3CC(F)(F)C3)c(OCC3CC3)n2)CCOCC1]

In analogy to the procedure described in example 54 b), (4-{[6-cyclopropylmethoxy-5-(3,3-difluoro-azetidin-1-yl)-pyridine-2-carbonyl]-amino}-tetrahydro-pyran-4-yl)-acetic acid (Example 57) was reacted with carbonyldiimidazole and NH₃ to give the title compound as light yellow oil; MS (EI): m/e=425.5 [MH⁺].

Example 61

6-Cyclopropylmethoxy-5-(3,3-difluoro-azetidin-1-yl)-pyridine-2-carboxylic acid (3-carbamoylmethyl-1,1-dioxo-1λ6-thietan-3-yl)-amide

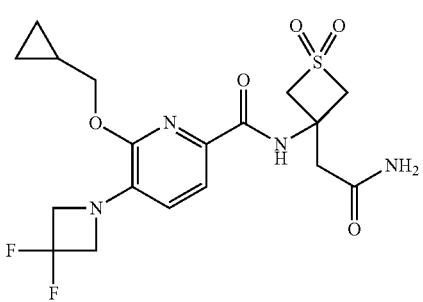 [SMILES: NC(=O)CC1(NC(=O)c2ccc(N3CC(F)(F)C3)c(OCC3CC3)n2)CS(=O)(=O)C1]

In analogy to the procedure described in example 54 b), (3-{[6-cyclopropylmethoxy-5-(3,3-difluoro-azetidin-1-yl)-pyridine-2-carbonyl]-amino}-1,1-dioxo-1λ6-thietan-3-yl)-acetic acid (Example 56) was reacted with carbonyldiimidazole and NH₃ to give the title compound as off-white solid; MS (EI): m/e=445.4 [MH⁺].

Example 62

6-Cyclopropylmethoxy-5-(3,3-difluoro-azetidin-1-yl)-pyridine-2-carboxylic acid (4-carbamoylmethyl-tetrahydro-thiopyran-4-yl)-amide

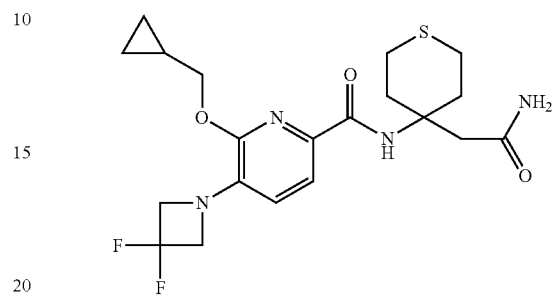

In analogy to the procedure described in Example 1 d), 6-cyclopropylmethoxy-5-(3,3-difluoro-azetidin-1-yl)-pyridine-2-carboxylic acid (Example 2 b)) was reacted with 2-(4-aminotetrahydro-2H-thiopyran-4-yl)acetamide (CAN 178243-06-6) in the presence of TBTU and DIEA to obtain the title compound as light yellow oil; MS (EI): m/e=441.5 [MH⁺].

Example 63

N-[4-(2-Amino-2-oxoethyl)-1,1-dioxothian-4-yl]-6-(cyclopropylmethoxy)-5-(3,3-difluoroazetidin-1-yl) pyridine-2-carboxamide

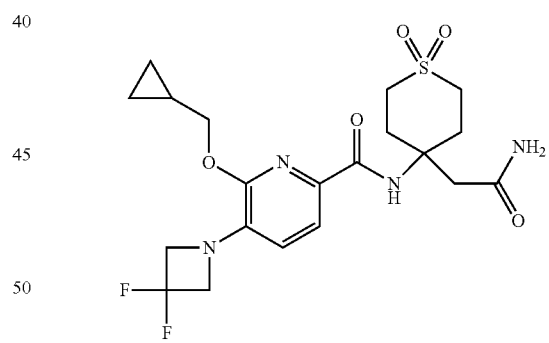

m-CPBA (21.5 mg, 125 µmol) was added to a suspension of 6-cyclopropylmethoxy-5-(3,3-difluoro-azetidin-1-yl)-pyridine-2-carboxylic acid (4-carbamoylmethyl-tetrahydro-thiopyran-4-yl)-amide (Example 62, 25 mg, 56.8 µmol) in DCM (2 mL). The reaction mixture was stirred for 12 h at ambient temperature. Ice cold 1 M NaOH solution (1.5 mL) was added. The mixture was stirred for 4 min and then poured onto a 10 g Chem Elut column. After 5 min the column was washed with DCM (50 mL). The solution was concentrated in vacuo to give a light yellow oil which was purified by preparative TLC (silica gel, 1.0 mm, Heptanes/EtOAc 1:2) to obtain the title compound (7 mg, 26%) as off-white solid; MS (ESI): m/e=473.4 [MH⁺].

Example 64

N-[3-Amino-3-oxo-1-(oxolan-3-yl)propyl]-5-cyclopropyl-6-(cyclopropylmethoxy)pyridine-2-carboxamide

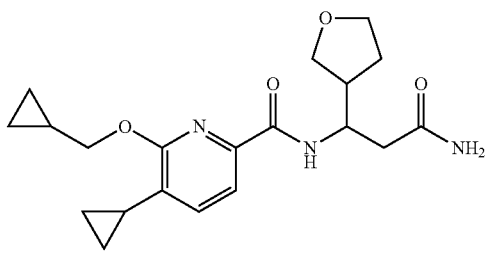 [SMILES: NC(=O)CC(NC(=O)c1ccc(C2CC2)c(OCC2CC2)n1)C1CCOC1]

In analogy to the procedure described in Example 1 d), 5-cyclopropyl-6-cyclopropylmethoxy-pyridine-2-carboxylic acid (Example 1 c, 100 mg, 429 µmol) was reacted with 3-amino-3-(tetrahydrofuran-3-yl)propanamide (CAN 771523-32-1, 74.6 mg, 472 µmol) in the presence of TBTU and DIEA to obtain the title compound (32 mg, 20%) as white solid; LC-MS (UV peak area, ESI) 97%, 374.2085 [MH+].

Example 65

N-[3-(2-Amino-2-oxoethyl)azetidin-3-yl]-6-(cyclopropylmethoxy)-5-(3,3-difluoroazetidin-1-yl)pyridine-2-carboxamide

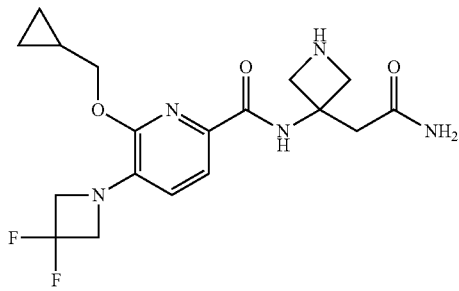 [SMILES: NC(=O)CC1(NC(=O)c2ccc(N3CC(F)(F)C3)c(OCC3CC3)n2)CNC1]

a) Benzyl 3-[[6-(cyclopropylmethoxy)-5-(3,3-difluoroazetidin-1-yl)pyridine-2-carbonyl]amino]-3-(2-ethoxy-2-oxo-ethyl)azetidine-1-carboxylate In analogy to the procedure described in Example 1 d), 6-cyclopropylmethoxy-5-(3,3-difluoro-azetidin-1-yl)-pyridine-2-carboxylic acid (Example 2 b, 100 mg, 296 µmol) was reacted with benzyl 3-amino-3-(2-ethoxy-2-oxoethyl)azetidine-1-carboxylate (CAN 1262407-36-2, 104 mg, 355 µmol) in the presence of TBTU and DIEA to obtain the title compound (134 mg, 81%) as light yellow oil; MS (ESI) m/e=559.5 [MH+].

b) 2-[1-Benzyloxycarbonyl-3-[[6-(cyclopropylmethoxy)-5-(3,3-difluoroazetidin-1-yl)pyridine-2-carbonyl]amino]azetidin-3-yl]acetic acid

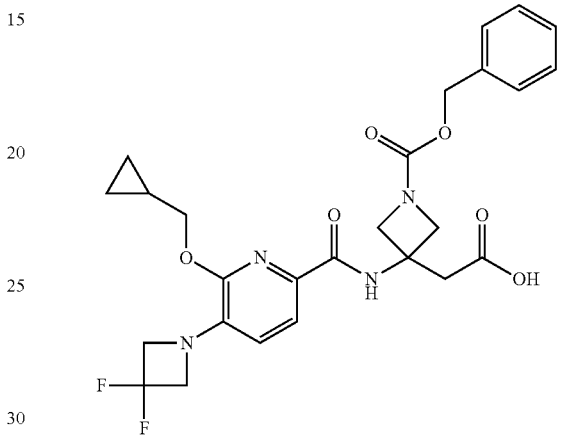

Lithium hydroxide hydrate (11.7 mg, 279 µmol) was added to a solution of benzyl 3-[[6-(cyclopropylmethoxy)-5-(3,3-difluoroazetidin-1-yl)pyridine-2-carbonyl]amino]-3-(2-ethoxy-2-oxo-ethyl)azetidine-1-carboxylate (Example 65 a, 130 mg, 233 µmol) in THF (676 µL) and water (270 µL). The reaction mixture was stirred at ambient temperature for 12 h, poured into 20 mL ice water/1M HCl and extracted with EtOAc (2×20 mL). The combined organic layers were washed with icewater/brine (20 mL), dried over Na$_2$SO$_4$ and concentrated in vacuo to give the title compound (114 mg, 92%) as yellow oil; MS (ESI) m/e=531.4 [MH+].

c) Benzyl 3-(2-amino-2-oxo-ethyl)-3-[[6-(cyclopropylmethoxy)-5-(3,3-difluoroazetidin-1-yl)pyridine-2-carbonyl]amino]azetidine-1-carboxylate

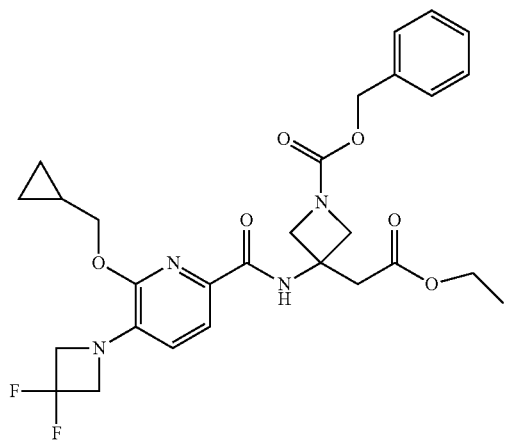 [SMILES: CCOC(=O)CC1(NC(=O)c2ccc(N3CC(F)(F)C3)c(OCC3CC3)n2)CN(C(=O)OCc2ccccc2)C1]

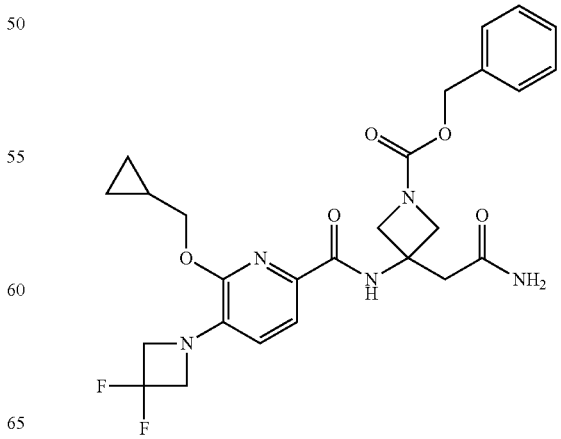

Carbonyldiimidazole (92.4 mg, 570 µmol) was added to an ice cold solution of 2-[1-benzyloxycarbonyl-3-[[6-(cyclopropylmethoxy)-5-(3,3-difluoroazetidin-1-yl)pyridine-2-carbonyl]amino]azetidin-3-yl]acetic acid (Example 65 b, 108 mg, 204 µmol) in DMF (4 mL). After 5 minutes the cooling bath was removed and stirring was continued for 2 h at ambient temperature. Gaseous ammonia was bubbled through the mixture for 10 min. After stirring for 12 h at ambient temperature the mixtures was poured into 20 mL icewater/1N HCl and extracted with EtOAc (2×20 mL). The organic layers were combined, dried over $Na_2SO_4$ and concentrated in vacuo to give the title compound (105 mg, 97%) as white solid which was used in the next reaction step without further purification; MS (ESI): m/e=530.5 [MH$^+$].

d) N-[3-(2-Amino-2-oxoethyl)azetidin-3-yl]-6-(cyclopropylmethoxy)-5-(3,3-difluoroazetidin-1-yl)pyridine-2-carboxamide 10% Pd on C (47.2 µmol) was added to a solution of benzyl 3-(2-amino-2-oxo-ethyl)-3-[[6-(cyclopropylmethoxy)-5-(3,3-difluoroazetidin-1-yl)pyridine-2-carbonyl]amino]azetidine-1-carboxylate (Example 65 c, 25 mg, 47.2 µmol) in methanol (6 mL) under a hydrogen atmosphere. The reaction mixture was stirred for 1 h at ambient temperature. The catalyst was filtered off, washed with methanol and the solvent was removed in vacuo to give the title compound (18 mg, 96%) as white solid; MS (ESI): m/e=396.5 [MH$^+$].

Example 66

N-[4-(2-Amino-2-oxoethyl)piperidin-4-yl]-5-cyclopropyl-6-[(4-fluorophenyl)methyl]pyridine-2-carboxamide; hydrochloride

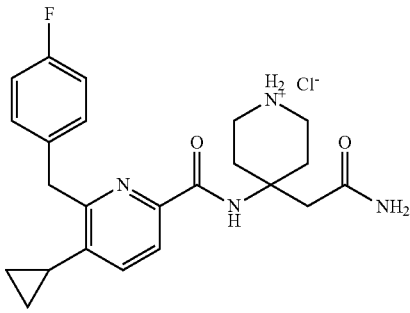

a) tert-Butyl 4-[[5-cyclopropyl-6-[(4-fluorophenyl)methyl]pyridine-2-carbonyl]amino]-4-(2-methoxy-2-oxo-ethyl)piperidine-1-carboxylate

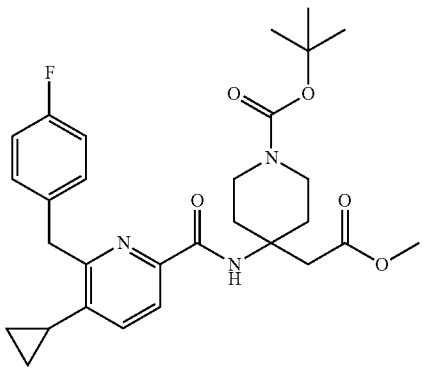 [SMILES: COC(=O)CC1(NC(=O)c2ccc(C3CC3)c(Cc3ccc(F)cc3)n2)CCN(C(=O)OC(C)(C)C)CC1]

In analogy to the procedure described in Example 1 d), 5-cyclopropyl-6-[(4-fluorophenyl)methyl]pyridine-2-carboxylic acid (CAN 1415899-48-7, 80 mg, 295 µmol) was reacted with tert-butyl 4-amino-4-(2-methoxy-2-oxoethyl)piperidine-1-carboxylate (CAN 362703-57-9, 96.4 mg, 354 µmol) in the presence of TBTU and DIEA to obtain the title compound (99 mg, 64%) as white waxy solid; MS (ESI) m/e=526.7 [MH$^+$].

b) 2-[1-tert-Butoxycarbonyl-4-[[5-cyclopropyl-6-[(4-fluorophenyl)methyl]pyridine-2-carbonyl]amino]-4-piperidyl]acetic acid

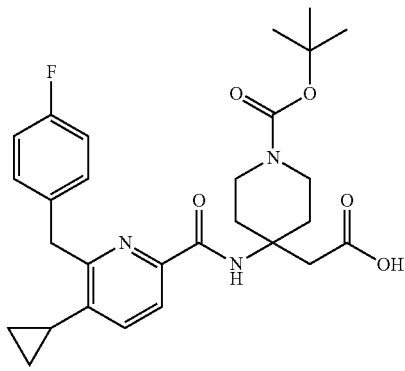 [SMILES: CC(C)(C)OC(=O)N1CCC(CC(=O)O)(NC(=O)c2ccc(C3CC3)c(Cc3ccc(F)cc3)n2)CC1]

In analogy to the procedure described in Example 65 b), tert-butyl 4-[[5-cyclopropyl-6-[(4-fluorophenyl)methyl]pyridine-2-carbonyl]amino]-4-(2-methoxy-2-oxo-ethyl)piperidine-1-carboxylate (Example 65 a, 99 mg, 188 µmol) was saponified with lithium hydroxide hydrate to give the title compound (96 mg, quant.) as a colourless oil; MS (ESI) m/e=512.5 [MH$^+$].

c) tert-Butyl 4-(2-amino-2-oxo-ethyl)-4-[[5-cyclopropyl-6-[(4-fluorophenyl)methyl]pyridine-2-carbonyl]amino]piperidine-1-carboxylate

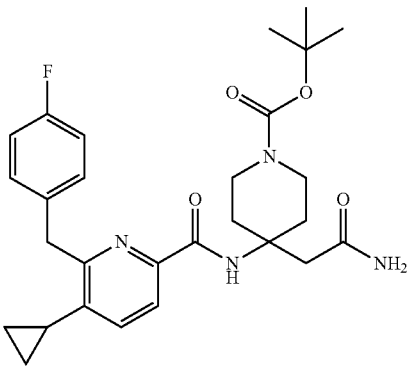 [SMILES: CC(C)(C)OC(=O)N1CCC(CC(N)=O)(NC(=O)c2ccc(C3CC3)c(Cc3ccc(F)cc3)n2)CC1]

In analogy to the procedure described in Example 65 c), 2-[1-tert-butoxycarbonyl-4-[[5-cyclopropyl-6-[(4-fluorophenyl)methyl]pyridine-2-carbonyl]amino]-4-piperidyl] acetic acid (Example 66 b, 96 mg, 188 µmol) was reacted with CDI and gaseous NH$_3$ to obtain the title compound (82 mg, 86%) as white foam; MS (ESI) m/e=511.5 [MH$^+$].

d) N-[4-(2-Amino-2-oxoethyl)piperidin-4-yl]-5-cyclopropyl-6-[(4-fluorophenyl)methyl]pyridine-2-carboxamide; hydrochloride A 4 M solution of HCl in dioxane (294 µL, 1.18 mmol) was added to a solution of tert-butyl 4-(2-amino-2-oxoethyl)-4-[[5-cyclopropyl-6-[(4-fluorophenyl)methyl]pyridine-2-carbonyl]amino]piperidine-1-carboxylate (Example 66 c, 60 mg, 118 µmol) in DCM (1 mL). The reaction mixture was stirred at ambient temperature for 12 h and concentrated in vacuo to give the title compound (58 mg, quant.) as off-white solid; MS (ESI): m/e=411.5 [MH−Cl⁺].

Example 67

N-[3-Amino-3-oxo-1-(oxolan-3-yl)propyl]-6-(cyclopropylmethoxy)-5-(3,3-difluoroazetidin-1-yl)pyridine-2-carboxamide

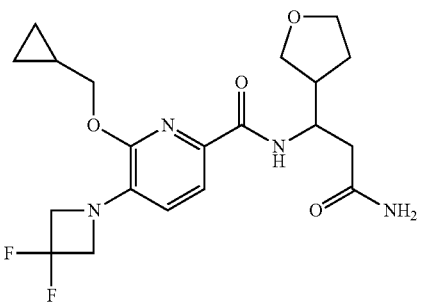 [SMILES: NC(=O)CC(NC(=O)c1ccc(N2CC(F)(F)C2)c(OCC2CC2)n1)C1CCOC1]

In analogy to the procedure described in Example 1 d), 6-cyclopropylmethoxy-5-(3,3-difluoro-azetidin-1-yl)-pyridine-2-carboxylic acid (Example 2 b, 40 mg, 141 µmol) was reacted with 3-amino-3-(tetrahydrofuran-3-yl)propanamide (CAN 771523-32-1, 26.7 mg, 169 µmol) in the presence of TBTU and DIEA to obtain the title compound (8 mg, 13%) as colorless oil; GC-MS (ESI) m/e=423.1840 [M−H⁻].

Example 68

Methyl 2-[1-[[6-(cyclopropylmethoxy)-5-(3,3-difluoroazetidin-1-yl)pyridine-2-carbonyl]amino]cyclobutyl]acetate

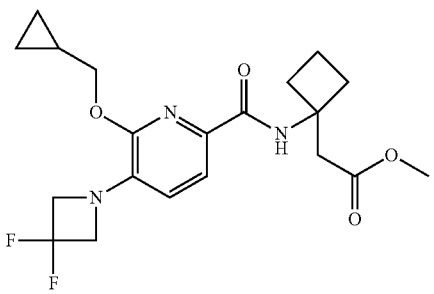 [SMILES: COC(=O)CC1(NC(=O)c2ccc(N3CC(F)(F)C3)c(OCC3CC3)n2)CCC1]

In analogy to the procedure described in Example 1 d), 6-cyclopropylmethoxy-5-(3,3-difluoro-azetidin-1-yl)-pyridine-2-carboxylic acid (Example 2 b, 50 mg, 176 µmol) was reacted with methyl 2-(1-aminocyclobutyl)acetate (CAN 1199779-19-5, 30.2 mg, 211 mol), in the presence of TBTU and DIEA to obtain the title compound (40 mg, 56%) as light yellow oil; MS (ESI): m/e=410.6 [MH⁺].

Example 69

2-[1-[[6-(Cyclopropylmethoxy)-5-(3,3-difluoroazetidin-1-yl)pyridine-2-carbonyl]amino]cyclobutyl]acetic acid

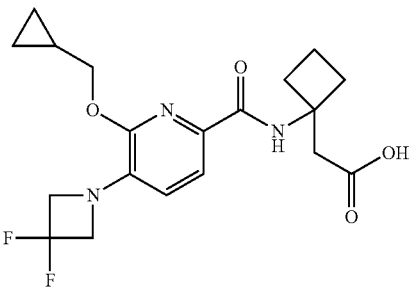 [SMILES: O=C(O)CC1(NC(=O)c2ccc(N3CC(F)(F)C3)c(OCC3CC3)n2)CCC1]

In analogy to the procedure described in Example 65 b), methyl 2-[1-[[6-(cyclopropylmethoxy)-5-(3,3-difluoroazetidin-1-yl)pyridine-2-carbonyl]amino]cyclobutyl]acetate (Example 68, 35 mg, 85.5 µmol) was saponified with lithium hydroxide hydrate to give the title compound (32 mg, 95%) as off-white viscous oil; MS (ESI) m/e=396.6 [MH⁺].

Example 70

N-[1-(2-Amino-2-oxoethyl)cyclobutyl]-6-(cyclopropylmethoxy)-5-(3,3-difluoroazetidin-1-yl)pyridine-2-carboxamide

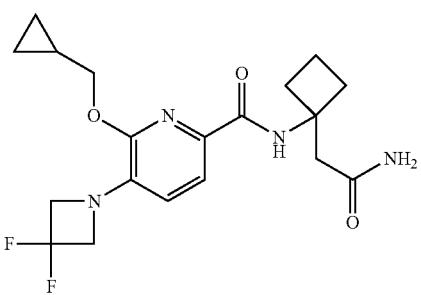 [SMILES: NC(=O)CC1(NC(=O)c2ccc(N3CC(F)(F)C3)c(OCC3CC3)n2)CCC1]

In analogy to the procedure described in Example 65 c), 2-[1-[[6-(cyclopropylmethoxy)-5-(3,3-difluoroazetidin-1-yl)pyridine-2-carbonyl]amino]cyclobutyl]acetic acid (Example 69, 29 mg, 73.3 µmol) was reacted with CDI and gaseous NH₃ to obtain the title compound (26 mg, 90%) as light yellow viscous oil; MS (ESI) m/e=395.5 [MH⁺].

Example 71

Ethyl 1-[[[6-(cyclopropylmethoxy)-5-(3,3-difluoro-azetidin-1-yl)pyridine-2-carbonyl]amino]methyl]cyclopropane-1-carboxylate

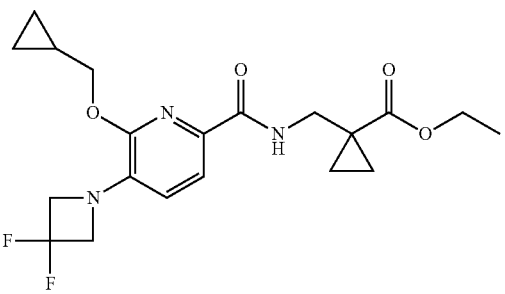 [SMILES: CCOC(=O)C1(CNC(=O)c2ccc(N3CC(F)(F)C3)c(OCC3CC3)n2)CC1]

In analogy to the procedure described in Example 1 d), 6-cyclopropylmethoxy-5-(3,3-difluoro-azetidin-1-yl)-pyridine-2-carboxylic acid (Example 2 b, 100 mg, 352 μmol) was reacted with ethyl 1-(aminomethyl)cyclopropanecarboxylate (CAN 400840-94-0, 60.4 mg, 422 μmol) in the presence of TBTU and DIEA to obtain the title compound (122 mg, 85%) as colorless oil; MS (ESI) m/e=410.6 [MH⁺].

Example 72

N-[1-Acetyl-4-(2-amino-2-oxoethyl)piperidin-4-yl]-5-cyclopropyl-6-[(4-fluorophenyl)methyl]pyridine-2-carboxamide

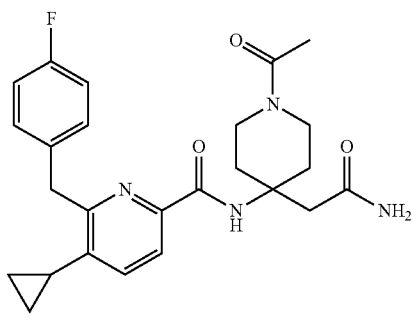 [SMILES: CC(=O)N1CCC(CC(N)=O)(NC(=O)c2ccc(C3CC3)c(Cc3ccc(F)cc3)n2)CC1]

Acetic anhydride (5.48 mg, 5.08 μL, 53.7 μmol) was added to a solution of N-[4-(2-amino-2-oxoethyl)piperidin-4-yl]-5-cyclopropyl-6-[(4-fluorophenyl)methyl]pyridine-2-carboxamide; hydrochloride (Example 66 c, 20 mg, 44.7 μmol) in pyridine (247 μL). The mixture was stirred for 30 min. at ambient temperature, for 1 h 80° C. and subsequently concentrated in vacuo to give a yellow oil which was purified by preparative TLC (silica gel, 1.0 mm, 30:1 DCM/MeOH) to give the title compound (3 mg, 15%) as off-white oil; MS (ESI) m/e=453.5 [MH⁺].

Example 73

N-[1-Acetyl-3-(2-amino-2-oxoethyl)azetidin-3-yl]-6-(cyclopropylmethoxy)-5-(3,3-difluoroazetidin-1-yl)pyridine-2-carboxamide

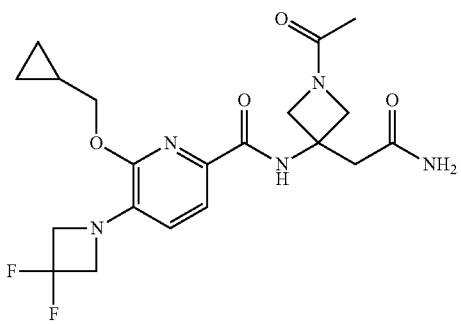 [SMILES: CC(=O)N1CC(CC(N)=O)(NC(=O)c2ccc(N3CC(F)(F)C3)c(OCC3CC3)n2)C1]

In analogy to the procedure described in Example 72, N-[3-(2-amino-2-oxoethyl)azetidin-3-yl]-6-(cyclopropylmethoxy)-5-(3,3-difluoroazetidin-1-yl)pyridine-2-carboxamide (Example 65 d, 8 mg, 20.2 μmol) was reacted with acetic anhydride (2.48 mg, 2.3 μL, 24.3 μmol) to give the target compound (9 mg, quant.) as off-white solid; MS (ESI) m/e=438.4 [MH⁺].

Example 74

Benzyl 3-(2-amino-2-oxoethyl)-3-[[5-cyclopropyl-6-[(4-fluorophenyl)methyl]pyridine-2-carbonyl]amino]azetidine-1-carboxylate

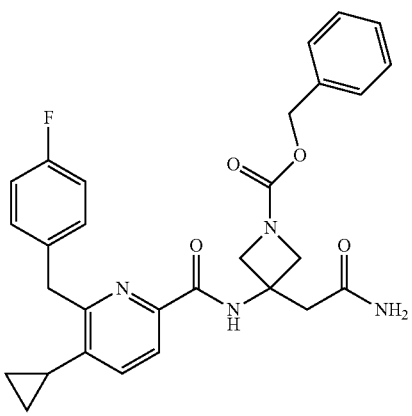 [SMILES: NC(=O)CC1(NC(=O)c2ccc(C3CC3)c(Cc3ccc(F)cc3)n2)CN(C(=O)OCc2ccccc2)C1]

a) Benzyl 3-[[5-cyclopropyl-6-[(4-fluorophenyl)methyl]pyridine-2-carbonyl]amino]-3-(2-ethoxy-2-oxo-ethyl)azetidine-1-carboxylate

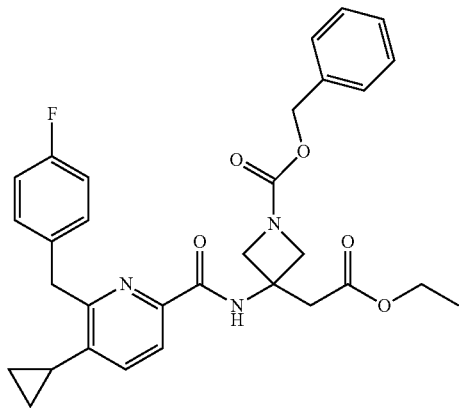 [SMILES: CCOC(=O)CC1(NC(=O)c2ccc(C3CC3)c(Cc3ccc(F)cc3)n2)CN(C(=O)OCc2ccccc2)C1]

In analogy to the procedure described in Example 1 d), 5-cyclopropyl-6-[(4-fluorophenyl)methyl]pyridine-2-carboxylic acid (CAN 1415899-48-7, 50 mg, 184 μmol) was reacted with benzyl 3-amino-3-(2-ethoxy-2-oxoethyl)azetidine-1-carboxylate (CAN 1262407-36-2, 64.7 mg, 221 μmol) in the presence of TBTU and DIEA to obtain the title compound (60 mg, 63%) as light yellow viscous oil; MS (ESI) m/e=546.4 [MH$^+$].

b) 2-[1-Benzyloxycarbonyl-3-[[5-cyclopropyl-6-[(4-fluorophenyl)methyl]pyridine-2-carbonyl]amino]azetidin-3-yl]acetic acid

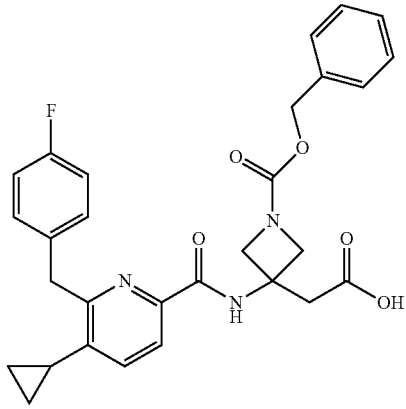 [SMILES: O=C(O)CC1(NC(=O)c2ccc(C3CC3)c(Cc3ccc(F)cc3)n2)CN(C(=O)OCc2ccccc2)C1]

In analogy to the procedure described in Example 65 b), benzyl 3-[[5-cyclopropyl-6-[(4-fluorophenyl)methyl]pyridine-2-carbonyl]amino]-3-(2-ethoxy-2-oxo-ethyl)azetidine-1-carboxylate (Example 74 a, 55 mg, 101 μmol) was saponified with lithium hydroxide hydrate to give the title compound (50 mg, 96%) as colorless oil; MS (ESI) m/e=518.6 [MH$^+$].

c) Benzyl 3-(2-amino-2-oxoethyl)-3-[[5-cyclopropyl-6-[(4-fluorophenyl)methyl]pyridine-2-carbonyl]amino]azetidine-1-carboxylate In analogy to the procedure described in Example 65 c), 2-[1-benzyloxycarbonyl-3-[[5-cyclopropyl-6-[(4-fluorophenyl)methyl]pyridine-2-carbonyl]amino]azetidin-3-yl]acetic acid (Example 74 b, 47 mg, 90.8 μmol) was reacted with CDI and gaseous NH$_3$ to obtain the title compound (47 mg, quant.) as yellow oil; MS (ESI) m/e=517.4 [MH$^+$].

Example 75

N-[3-(2-Amino-2-oxoethyl)-1,1-dioxothietan-3-yl]-5-cyclopropyl-6-(2-methylpropylsulfanyl)pyridine-2-carboxamide

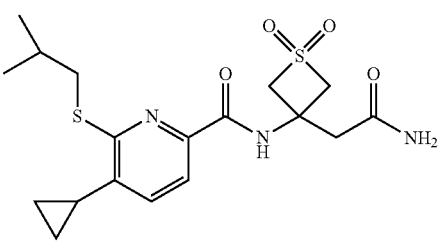 [SMILES: CC(C)CSc1nc(C(=O)NC2(CC(N)=O)CS(=O)(=O)C2)ccc1C1CC1]

a) 2-[3-(Benzylamino)-1,1-dioxo-thietan-3-yl]acetic acid

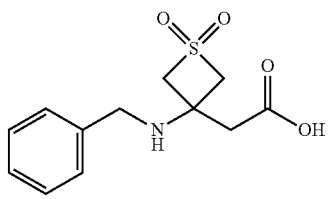 [SMILES: O=C(O)CC1(NCc2ccccc2)CS(=O)(=O)C1]

In analogy to the procedure described in Example 65 b), (3-benzylamino-1,1-dioxo-1λ6-thietan-3-yl)-acetic acid ethyl ester (Example 51 b, 1.44 g, 4.84 mmol) was saponified with lithium hydroxide hydrate to give the title compound (1.03 g, 79%) as off-white solid; MS (ESI) m/e=270.4 [MH$^+$].

b) 2-[3-(Benzylamino)-1,1-dioxo-thietan-3-yl]acetamide

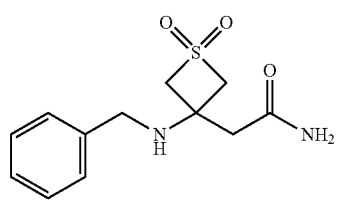 [SMILES: NC(=O)CC1(NCc2ccccc2)CS(=O)(=O)C1]

In analogy to the procedure described in Example 65 c), 2-[3-(benzylamino)-1,1-dioxo-thietan-3-yl]acetic acid (Example 75 a, 1.03 g, 3.82 mmol) was reacted with CDI and gaseous NH₃ to obtain the title compound (466 mg, 36%) as yellow viscous oil; MS (ESI) m/e=269.5 [MH⁺].

c) 2-(3-Amino-1,1-dioxo-thietan-3-yl)acetamide

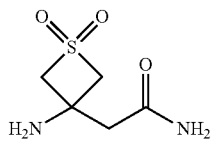

In analogy to the procedure described in Example 51 c), 2-[3-(benzylamino)-1,1-dioxo-thietan-3-yl]acetamide (Example 75 b, 466 mg, 1.39 mmol) was hydrogenated in the presence of 10% Palladium on charcoal to give the title compound (141 mg, 57%) as white solid; MS (ESI) m/e=179.1 [MH⁺].

d) N-[3-(2-Amino-2-oxoethyl)-1,1-dioxothietan-3-yl]-5-cyclopropyl-6-(2-methylpropylsulfanyl)pyridine-2-carboxamide In analogy to the procedure described in Example 1 d), 5-cyclopropyl-6-isobutylsulfanyl-pyridine-2-carboxylic acid (CAN 1415900-45-6, 15 mg, 59.7 µmol) was reacted with 2-(3-amino-1,1-dioxo-thietan-3-yl)acetamide (Example 75 c, 12.8 mg, 71.6 µmol) in the presence of TBTU and DIEA to obtain the title compound (10 mg, 41%) as white solid; MS (ESI) m/e=412.6 [MH⁺].

Example 76

N-[3-(2-Amino-2-oxoethyl)-1,1-dioxothietan-3-yl]-5-cyclopropyl-6-[(4-fluorophenyl)methyl]pyridine-2-carboxamide

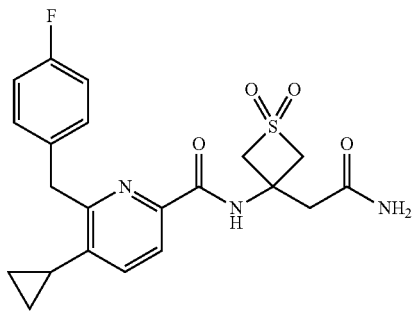 [SMILES: NC(=O)CC1(NC(=O)c2ccc(C3CC3)c(Cc3ccc(F)cc3)n2)CS(=O)(=O)C1]

In analogy to the procedure described in Example 1 d), 5-cyclopropyl-6-[(4-fluorophenyl)methyl]pyridine-2-carboxylic acid (CAN 1415899-48-7, 20 mg, 73.7 µmol) was reacted with 2-(3-amino-1,1-dioxo-thietan-3-yl)acetamide (Example 75 c, 15.8 mg, 88.5 µmol) in the presence of TBTU and DIEA to obtain the title compound (24 mg, 75%) as white solid; MS (ESI) m/e=432.4 [MH⁺].

Example 77

N-[3-(2-Amino-2-oxoethyl)-1,1-dioxothietan-3-yl]-5-cyclopropyl-6-(cyclopropylmethoxy)pyridine-2-carboxamide

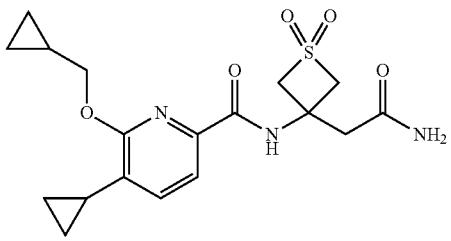 [SMILES: NC(=O)CC1(NC(=O)c2ccc(C3CC3)c(OCC3CC3)n2)CS(=O)(=O)C1]

In analogy to the procedure described in Example 1 d), 5-cyclopropyl-6-cyclopropylmethoxy-pyridine-2-carboxylic acid (Example 1 c, 15 mg, 64.3 µmol) was reacted with 2-(3-amino-1,1-dioxo-thietan-3-yl)acetamide (Example 75 c, 13.8 mg, 77.2 µmol) in the presence of TBTU and DIEA to obtain the title compound (20 mg, 79%) as white solid; MS (ESI) m/e=394.4 [MH⁺].

Example 78

N-[3-(2-Amino-2-oxoethyl)-1,1-dioxothietan-3-yl]-6-(oxan-4-ylmethoxy)-5-(trifluoromethyl)pyridine-2-carboxamide

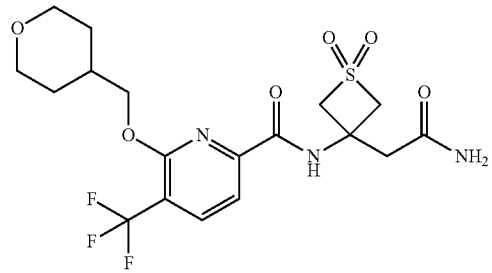 [SMILES: NC(=O)CC1(NC(=O)c2ccc(C(F)(F)F)c(OCC3CCOCC3)n2)CS(=O)(=O)C1]

In analogy to the procedure described in Example 1 d), 6-(tetrahydropyran-4-ylmethoxy)-5-(trifluoromethyl)pyridine-2-carboxylic acid (CAN 1415899-64-7, 20 mg, 65.5 µmol) was reacted with 2-(3-amino-1,1-dioxo-thietan-3-yl)acetamide (Example 75 c, 14.0 mg, 78.6 µmol) in the presence of TBTU and DIEA to obtain the title compound (18 mg, 59%) as white solid; MS (ESI) m/e=466.6 [MH⁺].

Example 79

N-[3-(2-Amino-2-oxoethyl)-1,1-dioxothietan-3-yl]-6-(3-chloro-4-fluorophenyl)pyridine-2-carboxamide

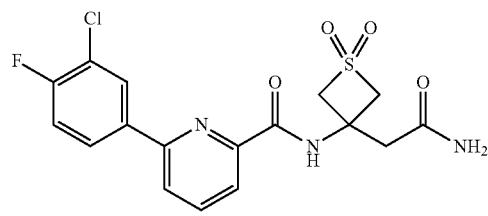 [SMILES: NC(=O)CC1(NC(=O)c2cccc(-c3ccc(F)c(Cl)c3)n2)CS(=O)(=O)C1]

In analogy to the procedure described in Example 1 d), 6-(3-chloro-4-fluoro-phenyl)pyridine-2-carboxylic acid (CAN 1261922-29-5, 20 mg, 79.5 µmol) was reacted with 2-(3-amino-1,1-dioxo-thietan-3-yl)acetamide (Example 75 c, 17.0 mg, 95.4 µmol) in the presence of TBTU and DIEA to obtain the title compound (26 mg, 79%) as white solid; MS (ESI) m/e=412.4 [MH$^+$].

Example 80

N-[3-(2-Amino-2-oxoethyl)-1,1-dioxothietan-3-yl]-5-cyclopropyl-6-(oxolan-2-ylmethoxy)pyridine-2-carboxamide

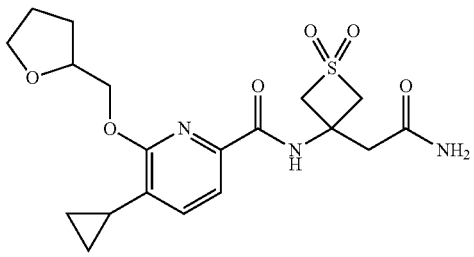 [SMILES: NC(=O)CC1(NC(=O)c2ccc(C3CC3)c(OCC3CCCO3)n2)CS(=O)(=O)C1]

In analogy to the procedure described in Example 1 d), 5-cyclopropyl-6-(tetrahydrofuran-2-ylmethoxy)pyridine-2-carboxylic acid (CAN 1415899-57-8, 20 mg, 76.0 µmol) was reacted with 2-(3-amino-1,1-dioxo-thietan-3-yl)acetamide (Example 75 c, 16.2 mg, 91.2 µmol) in the presence of TBTU and DIEA to obtain the title compound (23 mg, 72%) as white solid; MS (ESI) m/e=424.6 [MH$^+$].

Example 81

N-[3-(2-Amino-2-oxoethyl)azetidin-3-yl]-5-cyclopropyl-6-[(4-fluorophenyl)methyl]pyridine-2-carboxamide

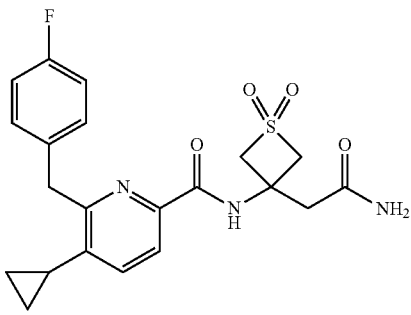 [SMILES: NC(=O)CC1(NC(=O)c2ccc(C3CC3)c(Cc3ccc(F)cc3)n2)CS(=O)(=O)C1]

In analogy to the procedure described in Example 65 d), benzyl 3-(2-amino-2-oxoethyl)-3-[[5-cyclopropyl-6-[(4-fluorophenyl)methyl]pyridine-2-carbonyl]amino]azetidine-1-carboxylate (Example 74 c, 45 mg, 87.1 µmol) was hydrogenated in the presence of 10% Pd on C to give the title compound (28 mg, 84%) as a light yellow oil; MS (ESI) m/e=383.5 [MH$^+$].

Example 82

N-[3-(2-Amino-2-oxoethyl)oxolan-3-yl]-6-(cyclopropylmethoxy)-5-(3,3-difluoroazetidin-1-yl)pyridine-2-carboxamide

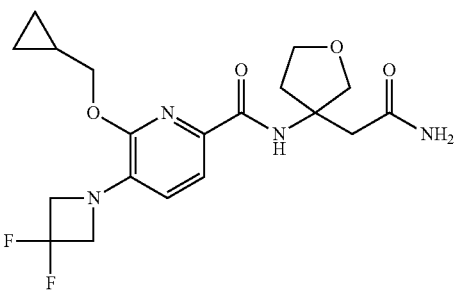 [SMILES: NC(=O)CC1(NC(=O)c2ccc(N3CC(F)(F)C3)c(OCC3CC3)n2)CCOC1]

a) Methyl 2-(3-aminotetrahydrofuran-3-yl)acetate hydrochloride

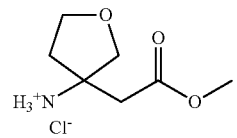

A mixture of 2-(3-aminotetrahydrofuran-3-yl)acetic acid hydrochloride (CAN 1427379-33-6, 200 mg, 1.1 mmol), 4M HCl in dioxane (1.38 mL, 5.51 mmol) and MeOH (2 mL) was stirred at ambient temperature for 2 d. The solvent was removed in vacuo to give crude title compound (220 mg, quant.) as white solid which was used in the next step without further purification; MS (ESI) m/e=160.2 [MH−Cl$^+$].

b) 2-(3-Aminotetrahydrofuran-3-yl)acetamide

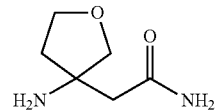

A 25% aqueous ammoniumhydroxide solution (640 mg, 711 µL, 18.2 mmol) was added at ambient temperature to a solution of methyl 2-(3-aminotetrahydrofuran-3-yl)acetate hydrochloride (Example 82 a, 175 mg, 894 µmol) in toluene (2.45 mL). The reaction mixture was stirred for 4 d and brought to dryness in vacuo to give crude title compound (230 mg, quant.) as off-white waxy solid which was used in the next step without further purification; MS (ESI) m/e=145.1 [MH$^+$].

c) N-[3-(2-Amino-2-oxoethyl)oxolan-3-yl]-6-(cyclopropylmethoxy)-5-(3,3-difluoroazetidin-1-yl)pyridine-2-carboxamide In analogy to the procedure described in Example 1 d), 6-cyclopropylmethoxy-5-(3,3-difluoro-azetidin-1-yl)-pyridine-2-carboxylic acid (Example 2 b, 30 mg, 106 µmol) was reacted with 2-(3-aminotetrahydrofuran-3-yl)acetamide (Example 82 b, 21.0 mg, 146 mol) in the presence of TBTU and DIEA to obtain the title compound (12 mg, 28%) as colorless oil; MS (ESI) m/e=411.4 [MH⁺].

Example 83

Benzyl 3-(2-amino-2-oxoethyl)-3-[[6-(cyclopropylmethoxy)-5-(3,3-difluoroazetidin-1-yl)pyridine-2-carbonyl]amino]pyrrolidine-1-carboxylate

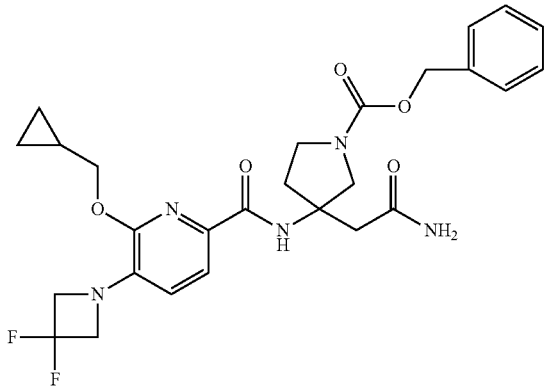 [SMILES: NC(=O)CC1(NC(=O)c2ccc(N3CC(F)(F)C3)c(OCC3CC3)n2)CCN(C(=O)OCc2ccccc2)C1]

a) Benzyl 3-(tert-butoxycarbonylamino)-3-(2-ethoxy-2-oxoethyl)pyrrolidine-1-carboxylate

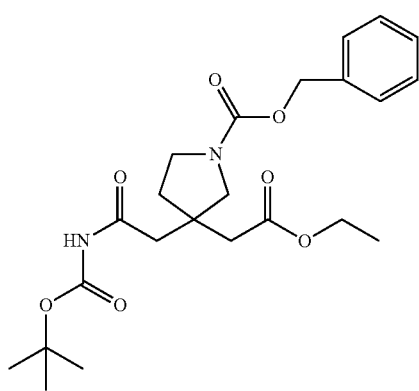 [SMILES: CCOC(=O)CC1(CC(=O)NC(=O)OC(C)(C)C)CCN(C(=O)OCc2ccccc2)C1]

Di-tert-butyl dicarbonate (590 mg, 2.7 mmol) and subsequently triethylamine (191 mg, 263 µL, 1.89 mmol) were added to a solution of benzyl 3-amino-3-(2-ethoxy-2-oxoethyl)pyrrolidine-1-carboxylate (CAN 1111202-74-4, 552 mg, 1.8 mmol) in THF (8 mL). The reaction mixture was stirred at room temperature for 12 h, poured into ice/water, acidified with 1M HCl solution and extracted two times with ethyl acetate. The combined organic layers were washed with brine, dried over Na₂SO₄, filtered and evaporated to give a dark brown liquid. The crude product was purified by flash chromatography (silica gel, 20 g, 0% to 20% EtOAc in heptane) to obtain the title compound (122 mg, 17%) as yellow oil; MS (ESI) m/e=407.2 [MH⁺].

b) 2-(1-(Benzyloxycarbonyl)-3-(tert-butoxycarbonylamino)pyrrolidin-3-yl)acetic acid

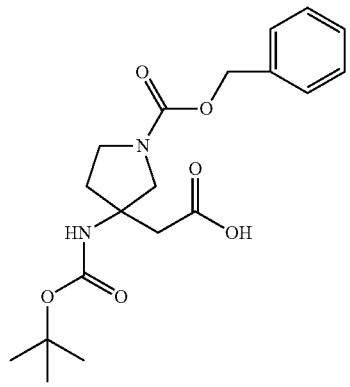 [SMILES: CC(C)(C)OC(=O)NC1(CC(=O)O)CCN(C(=O)OCc2ccccc2)C1]

In analogy to the procedure described in Example 65 b), benzyl 3-(tert-butoxycarbonylamino)-3-(2-ethoxy-2-oxoethyl)pyrrolidine-1-carboxylate (Example 83 a, 102 mg, 251 µmol) was saponified with lithium hydroxide hydrate to give the title compound (97 mg, 72%) as brown oil which was used in the next step without further purification; MS (ESI) m/e=279.5 [MH−Boc⁺].

c) Benzyl 3-(2-amino-2-oxoethyl)-3-(tert-butoxycarbonylamino)pyrrolidine-1-carboxylate

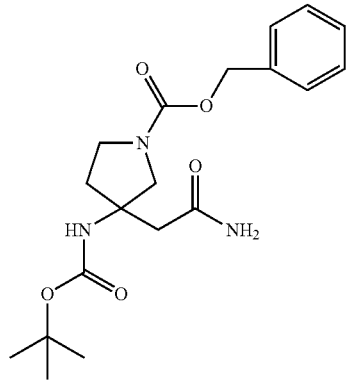

In analogy to the procedure described in Example 65 c), 2-(1-(benzyloxycarbonyl)-3-(tert-butoxycarbonylamino) pyrrolidin-3-yl)acetic acid (Example 83 b, 82 mg, 217 µmol) was reacted with CDI and gaseous NH₃ to obtain the title compound (39 mg, 48%) as yellow viscous oil; MS (ESI) m/e=278.5 [MH−Boc⁺].

d) Benzyl 3-amino-3-(2-amino-2-oxoethyl)pyrrolidine-1-carboxylate hydrochloride

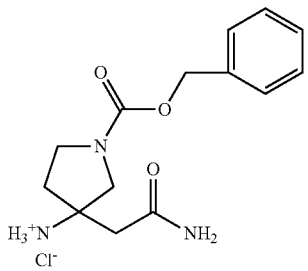

In analogy to the procedure described in Example 66 c), benzyl 3-(2-amino-2-oxoethyl)-3-(tert-butoxycarbonylamino)pyrrolidine-1-carboxylate (Example 83 c, 39 mg, 103 μmol) was deprotected using a 4 M solution of HCl in dioxane to obtain the title compound (35 mg, quant.) as yellow viscous oil; MS (ESI): m/e=278.4 [MH–Cl$^+$].

e) Benzyl 3-(2-amino-2-oxoethyl)-3-[[6-(cyclopropylmethoxy)-5-(3,3-difluoroazetidin-1-yl)pyridine-2-carbonyl]amino]pyrrolidine-1-carboxylate In analogy to the procedure described in Example 1 d), 6-cyclopropylmethoxy-5-(3,3-difluoro-azetidin-1-yl)-pyridine-2-carboxylic acid (Example 2 b, 25 mg, 87.9 μmol) was reacted with benzyl 3-amino-3-(2-amino-2-oxoethyl)pyrrolidine-1-carboxylate hydrochloride (Example 83 d, 33.1 mg, 106 μmol) in the presence of TBTU and DIEA to obtain the title compound (39 mg, 82%) as colorless oil; MS (ESI) m/e=544.4 [MH$^+$].

Example 84

N-[3-(2-Amino-2-oxoethyl)pyrrolidin-3-yl]-6-(cyclopropylmethoxy)-5-(3,3-difluoroazetidin-1-yl)pyridine-2-carboxamide

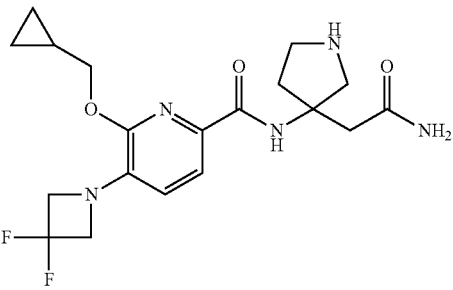 [SMILES: NC(=O)CC1(NC(=O)c2ccc(N3CC(F)(F)C3)c(OCC3CC3)n2)CCNC1]

In analogy to the procedure described in Example 65 d), benzyl 3-(2-amino-2-oxoethyl)-3-[[6-(cyclopropylmethoxy)-5-(3,3-difluoroazetidin-1-yl)pyridine-2-carbonyl]amino]pyrrolidine-1-carboxylate (Example 83 e, 10 mg, 18.4 μmol) was hydrogenated in the presence of 10% Pd on C to obtain the title compound (5 mg, 66%) as colorless solid; MS (ESI): m/e=410.7 [MH$^+$].

Example 85

N-[4-(2-Amino-2-oxoethyl)piperidin-4-yl]-6-(cyclopropylmethoxy)-5-(3,3-difluoroazetidin-1-yl)pyridine-2-carboxamide

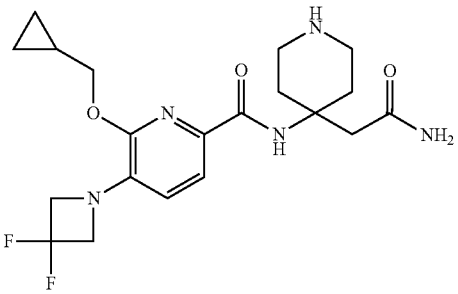 [SMILES: NC(=O)CC1(NC(=O)c2ccc(N3CC(F)(F)C3)c(OCC3CC3)n2)CCNCC1]

a) Benzyl 4-(2-amino-2-oxoethyl)-4-(tert-butoxycarbonylamino)piperidine-1-carboxylate

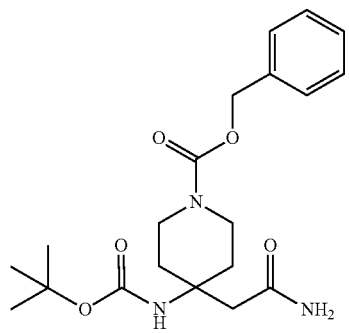 [SMILES: CC(C)(C)OC(=O)NC1(CC(N)=O)CCN(C(=O)OCc2ccccc2)CC1]

In analogy to the procedure described in Example 65 c), 2-(1-(benzyloxycarbonyl)-4-(tert-butoxycarbonylamino)piperidin-4-yl)acetic acid (CAN 303037-51-6, 721 mg, 1.84 mmol) was reacted with CDI and gaseous NH$_3$ to obtain the title compound (196 mg, 27%) as white solid; MS (ESI) m/e=292.6 [MH–Boc$^+$].

b) Benzyl 4-amino-4-(2-amino-2-oxoethyl)piperidine-1-carboxylate hydrochloride

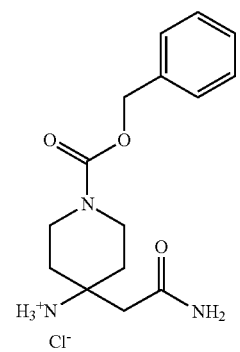

In analogy to the procedure described in Example 66 c), benzyl 4-(2-amino-2-oxoethyl)-4-(tert-butoxycarbonylamino)piperidine-1-carboxylate (Example 85 a, 196 mg, 501 μmol) was deprotected using a 4 M solution of HCl in c) Benzyl 4-(2-amino-2-oxo-ethyl)-4-[[6-(cyclopropylmethoxy)-5-(3,3-difluoroazetidin-1-yl)pyridine-2-carbonyl]amino]piperidine-1-carboxylate

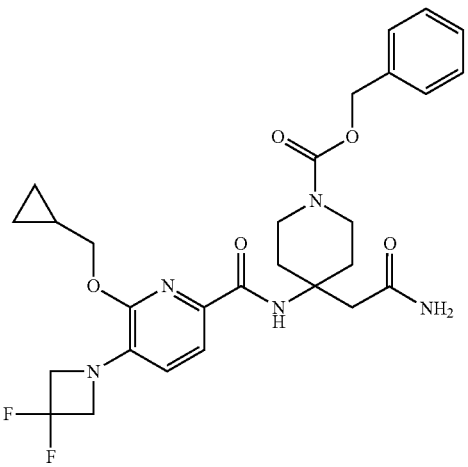 [SMILES: NC(=O)CC1(NC(=O)c2ccc(N3CC(F)(F)C3)c(OCC3CC3)n2)CCN(C(=O)OCc2ccccc2)CC1]

In analogy to the procedure described in Example 1 d), 6-cyclopropylmethoxy-5-(3,3-difluoro-azetidin-1-yl)-pyridine-2-carboxylic acid (Example 2 b, 30 mg, 106 μmol) was reacted with benzyl 4-amino-4-(2-amino-2-oxoethyl)piperidine-1-carboxylate hydrochloride (Example 85 b, 41.5 mg, 127 μmol) in the presence of TBTU and DIEA to obtain the title compound (24 mg, 41%) as colorless oil; MS (ESI) m/e=558.7 [MH+].

d) N-[4-(2-Amino-2-oxoethyl)piperidin-4-yl]-6-(cyclopropylmethoxy)-5-(3,3-difluoroazetidin-1-yl)pyridine-2-carboxamide In analogy to the procedure described in Example 65 d), benzyl 4-(2-amino-2-oxo-ethyl)-4-[[6-(cyclopropylmethoxy)-5-(3,3-difluoroazetidin-1-yl)pyridine-2-carbonyl]amino]piperidine-1-carboxylate (Example 85 c, 13 mg, 23.3 μmol) was hydrogenated in the presence of 10% Pd on C to obtain the title compound (8 mg, 81%) as white solid; MS (ESI) m/e=424.5 [MH+].

Example 86

N-[4-(2-Amino-2-oxoethyl)piperidin-4-yl]-5-cyclopropyl-6-(cyclopropylmethoxy)pyridine-2-carboxamide

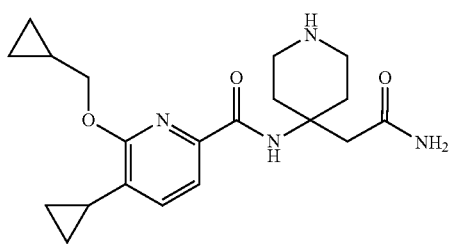 [SMILES: NC(=O)CC1(NC(=O)c2ccc(C3CC3)c(OCC3CC3)n2)CCNCC1]

a) Benzyl 4-(2-amino-2-oxo-ethyl)-4-[[5-cyclopropyl-6-(cyclopropylmethoxy)pyridine-2-carbonyl]amino]piperidine-1-carboxylate

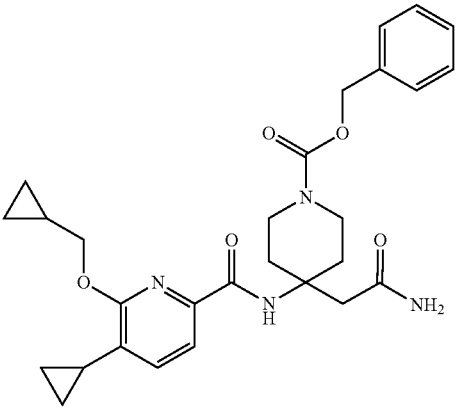 [SMILES: NC(=O)CC1(NC(=O)c2ccc(C3CC3)c(OCC3CC3)n2)CCN(C(=O)OCc2ccccc2)CC1]

A solution of 5-cyclopropyl-6-cyclopropylmethoxy-pyridine-2-carboxylic acid (Example 1 c, 26 mg, 111 μmol), benzyl 4-amino-4-(2-amino-2-oxoethyl)piperidine-1-carboxylate hydrochloride (Example 85 b, 43.8 mg, 134 μmol), 2-bromo-1-ethylpyridinium tetrafluoroborate (33.6 mg, 123 μmol) and DIEA (43.2 mg, 57.2 μL, 334 μmol) in THF (498 μL) was stirred for 2 d at ambient temperature. The reaction mixture was poured onto icewater/1N HCl and extracted with EtOAc (2×20 mL). The organic layers were combined, washed with icewater/brine, dried over Na2SO4, filtered and evaporated in vacuo to give a yellow oil. The crude material was purified by preparative HPLC to obtain the title compound (16 mg, 28%) as colorless solid; MS (ESI) m/e=507.7 [MH+].

b) N-[4-(2-Amino-2-oxoethyl)piperidin-4-yl]-5-cyclopropyl-6-(cyclopropylmethoxy)pyridine-2-carboxamide In analogy to the procedure described in Example 65 d), benzyl 4-(2-amino-2-oxo-ethyl)-4-[[5-cyclopropyl-6-(cyclopropylmethoxy)pyridine-2-carbonyl]amino]piperidine-1-carboxylate (Example 86 a, 12 mg, 23.7 μmol) was hydrogenated in the presence of 10% Pd on C to obtain the title compound (7 mg, 79%) as colorless solid; LC-MS (ESI) m/e=373.2219 [MH+].

Example 87

N-[3-(2-Amino-2-oxoethyl)oxolan-3-yl]-5-cyclopropyl-6-[(4-fluorophenyl)methyl]pyridine-2-carboxamide

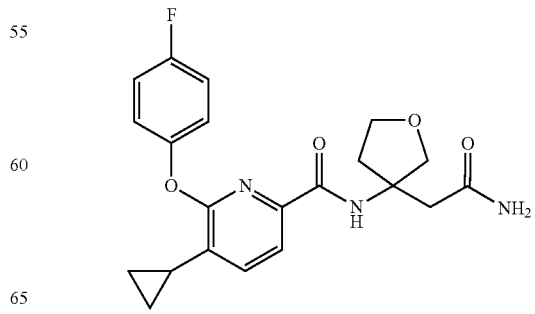

In analogy to the procedure described in Example 86 a), 5-cyclopropyl-6-[(4-fluorophenyl)methyl]pyridine-2-carboxylic acid (CAN 1415899-48-7, 30 mg, 111 µmol) was condensed with 2-(3-aminotetrahydrofuran-3-yl)acetamide (Example 82 b, 15.9 mg, 111 µmol) in the presence of BEP and DIEA to give the title compound (10 mg; 23%) as colorless liquid; MS (ESI) m/e=398.3 [MH$^+$].

Example 88

N-[3-(2-Amino-2-oxoethyl)oxolan-3-yl]-5-cyclopropyl-6-(cyclopropylmethoxy)pyridine-2-carboxamide

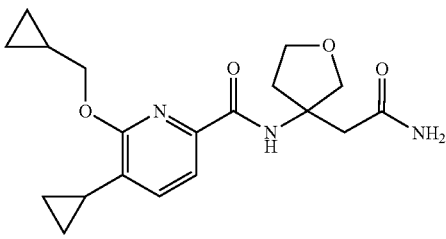 [SMILES: NC(=O)CC1(NC(=O)c2ccc(C3CC3)c(OCC3CC3)n2)CCOC1]

In analogy to the procedure described in Example 86 a), 5-cyclopropyl-6-cyclopropylmethoxy-pyridine-2-carboxylic acid (Example 1 c, 30 mg, 129 µmol) was condensed with 2-(3-aminotetrahydrofuran-3-yl)acetamide (Example 82 b, 18.5 mg, 129 µmol) in the presence of BEP and DIEA to give the title compound (13 mg; 28%) as colorless liquid; MS (ESI) m/e=360.4 [MH$^+$].

Example 89

N-[3-(2-Amino-2-oxoethyl)oxetan-3-yl]-6-(cyclopropylmethoxy)-5-(1-fluorocyclobutyl)pyridine-2-carboxamide

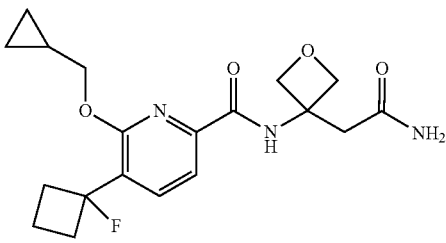 [SMILES: NC(=O)CC1(NC(=O)c2ccc(C3(F)CCC3)c(OCC3CC3)n2)COC1]

a) 1-(2-Chloro-6-methylpyridin-3-yl)cyclobutanol

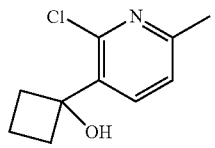

A suspension of molecular sieves (4 Å) and 3-bromo-2-chloro-6-methylpyridine (CAN 185017-72-5, 5 g, 24.2 mmol) in THF (50 mL) was cooled to −15° C. 1.3 M isopropyl magnesium chloride lithium chloride complex solution in THF (19.6 mL, 25.4 mmol) was added within 30 min. Stirring was continued for 1 h at −15° C. Cyclobutanone (1.87 g, 2.00 mL, 26.6 mmol) was slowly added. Stirring was continued for 2 h at −15° C. and for further 2 h at 0° C. Water (2.5 mL) was added, the mixture was concentrated in vacuo, and poured onto sat. aqueous NH$_4$Cl solution. The mixture was extracted with EtOAc (2×100 mL). The combined extracts were washed with ice water (50 mL), dried over Na$_2$SO$_4$ and concentrated in vacuo. The residue was purified by flash chromatography (silica gel, 140 g, heptane/EtOAc 0-40% in 120 min.) to give the title compound (3.33 g, 70%) as white solid, MS (ESI): m/e=198.1 [MH$^+$].

b) 2-Chloro-3-(1-fluorocyclobutyl)-6-methylpyridine

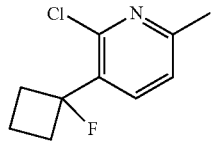

Diethylaminosulfur trifluoride (1.22 g, 1.00 mL, 7.57 mmol) was added to an ice cold solution of 1-(2-chloro-6-methylpyridin-3-yl)cyclobutanol (Example 89 a, 1 g, 5.06 mmol) in dichloromethane (10 mL) keeping the temperature below 5° C. The reaction mixture was stirred for 30 min. at 0° C., poured onto ice water/sat. aqueous Na$_2$CO$_3$ solution (35 mL) and extracted with dichloromethane (2×50 mL). The organic layers were combined, washed with ice water/brine (30 mL), dried over Na$_2$SO$_4$ and concentrated in vacuo. The residue was purified by flash chromatography (silica gel, 50 g, heptane/EtOAc 0-10% in 75 min) to give the title compound (939 mg, 93%) as colorless oil, MS (ESI): m/e=200.3 [MH$^+$].

c) 2-Chloro-3-(1-fluorocyclobutyl)-6-methylpyridine 1-oxide

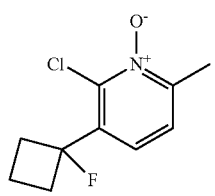

3-Chlorobenzoperoxoic acid (173 mg, 1.00 mmol) was added in 2 portions to a solution of 2-chloro-3-(1-fluorocyclobutyl)-6-methylpyridine (Example 89 b, 100 mg, 501 µmol) in dichloromethane (2 mL). The reaction mixture was stirred at ambient temperature for 72 h, poured onto a 10% aqueous Na$_2$S$_2$O$_3$ solution (30 mL) and extracted with dichloromethane (2×40 mL). The combined organic layers were washed with ice water/brine (30 mL), dried over Na$_2$SO$_4$ and concentrated in vacuo. The residue was dissolved in dichloromethane, washed with sat. NaHCO$_3$ solution (30 mL) and ice water (30 mL), dried over Na$_2$SO$_4$ and concentrated in vacuo to give the title compound (81 mg, 74%) as yellow oil, MS (ESI): m/e=216.3 [MH$^+$].

d) (6-Chloro-5-(1-fluorocyclobutyl)pyridin-2-yl)methanol

Trifluoroacetic anhydride (1.27 g, 840 μL, 6.04 mmol) was added under ice cooling to a solution of 2-chloro-3-(1-fluorocyclobutyl)-6-methylpyridine 1-oxide (Example 89 c, 869 mg, 4.03 mmol) in dichloromethane (10.9 mL). The mixture was stirred at ambient temperature for 72 h. Upon ice bath cooling 5 N NaOH solution (1 mL) and afterwards ice water (20 mL) were added. The mixture was extracted with dichloromethane (2×40 mL). The combined organic layers were washed with icewater/brine (20 mL), dried over $Na_2SO_4$ and concentrated in vacuo. The residue was purified by flash chromatography (silica gel, 50 g, heptane/EtOAc 0-40% in 120 min.) to give the title compound (279 mg, 32%) as light yellow oil, MS (ESI): m/e=216.3 [MH$^+$].

e) 6-Chloro-5-(1-fluorocyclobutyl)pyridine-2-carboxylic acid

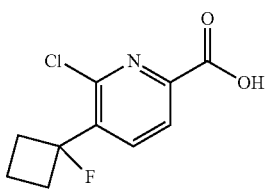 [SMILES: O=C(O)c1ccc(C2(F)CCC2)c(Cl)n1]

Aqueous phosphate buffer (pH=6.7, 0.7 mL) and TEMPO (2.54 mg, 16.2 μmol) were added to a solution of (6-chloro-5-(1-fluorocyclobutyl)pyridin-2-yl)methanol (Example 89 d, 50 mg, 232 μmol) in acetonitrile (1 mL) under an argon atmosphere. The reaction mixture was warmed to 35° C. A solution of sodium chlorite (52.4 mg, 464 μmol) in 150 μL water and a solution of sodium hypochlorite (2.66 mg, 2.19 μL, 4.64 μmol) in 100 μL water were added simultaneously over a period of 30 min. Stirring was continued at 35° C. for 20 h. Water (40 mL) and 2 N NaOH solution (8 mL) were added. The mixture was poured into an ice cold $Na_2SO_3$ solution (1.62 $Na_2SO_3$ g in 30 mL water) and stirred for 30 min. at ambient temperature. Under ice cooling the mixture was acidified with 25 mL 2 N HCl solution and extracted with a mixture of 100 mL EtOAc and 20 mL THF. The organic layer was dried over $Na_2SO_4$, filtered and the solvent concentrated in vacuo to give the title compound (66 mg, 90%) as yellow oil, MS(ESI): m/e=230.4 [MH$^+$].

f) 6-(Cyclopropylmethoxy)-5-(1-fluorocyclobutyl)pyridine-2-carboxylic acid

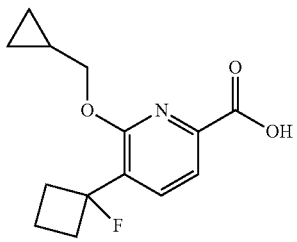 [SMILES: O=C(O)c1ccc(C2(F)CCC2)c(OCC2CC2)n1]

Powdered potassium hydroxide (240 mg, 4.28 mmol) was added to a solution of 6-chloro-5-(1-fluorocyclobutyl)pyridine-2-carboxylic acid (Example 89 e, 393 mg, 1.71 mmol) in DMSO (7.86 mL). The mixture was stirred at ambient temperature for 15 minutes. Cyclopropylmethanol (136 mg, 153 μL, 1.88 mmol) was added and stirring was continued for 5 h at 60° C. Additional cyclopropylmethanol (68 mg, 76 μL, 94 mmol) was added, the mixture was stirred for 14 h at ambient temperature, poured onto ice/brine (100 mL) and extracted with TBME (2×100 mL). The aqueous layer was acidified with 1 N HCl and extracted with EtOAc (2×150 mL). The combined organic layers were washed with ice/brine (50 mL), dried over $Na_2SO_4$ and filtered. The solvent was removed under reduced pressure and the residue was purified by flash-chromatography (20 g $SiO_2$, dichloromethane/MeOH 0-3% in 75 min) to give the title compound (65 mg, 31%) as colorless oil, MS (ESI) m/e=264.5 [M–H$^-$].

g) N-[3-(2-Amino-2-oxoethyl)oxetan-3-yl]-6-(cyclopropylmethoxy)-5-(1-fluorocyclobutyl)pyridine-2-carboxamide In analogy to the procedure described in Example 86 a), 6-(cyclopropylmethoxy)-5-(1-fluorocyclobutyl)pyridine-2-carboxylic acid (Example 89 f, 20 mg, 49.8 μmol) was condensed with 2-(3-amino-oxetan-3-yl)-acetamide (Example 23 a, 7.8 mg, 59.7 μmol) in the presence of BEP and DIEA to give the title compound (11 mg; 59%) as colorless liquid; MS (ESI) m/e=378.5 [MH$^+$].

Example 90

N-[3-(2-Amino-2-oxoethyl)oxetan-3-yl]-6-(cyclopropylmethoxy)-5-(1-hydroxycyclobutyl)pyridine-2-carboxamide

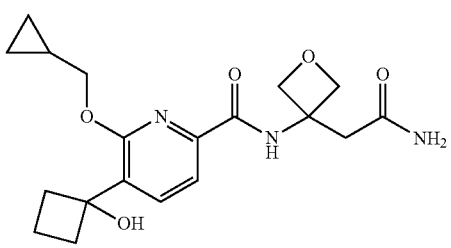

In analogy to the procedure described in Example 86 a), 6-(cyclopropylmethoxy)-5-(1-hydroxycyclobutyl)pyridine-2-carboxylic acid (CAN 1415899-53-4, 20 mg, 76.0 μmol)

was condensed with 2-(3-amino-oxetan-3-yl)-acetamide (Example 23 a, 11.9 mg, 91.2 mol) in the presence of BEP and DIEA to give the title compound (15 mg; 53%) as off-white solid; MS (ESI) m/e=376.5 [MH⁺].

Example 91

N-[3-(2-Amino-2-oxoethyl)thietan-3-yl]-6-(cyclopropylmethoxy)-5-(3,3-difluoroazetidin-1-yl)pyridine-2-carboxamide

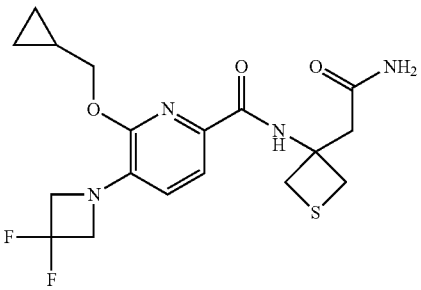 [SMILES: NC(=O)CC1(NC(=O)c2ccc(N3CC(F)(F)C3)c(OCC3CC3)n2)CSC1]

a) Methyl 2-(3-aminothietan-3-yl)acetate

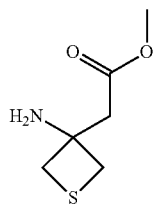

A solution of ethyl 2-(thietan-3-ylidene)acetate (1223573-30-5, 0.5 g, 3.16 mmol) in a 7 M solution of ammonia in MeOH (9.02 mL, 63.1 mmol) was stirred for 72 h at ambient temperature in a sealed tube. The solvent was removed in vacuo and the crude product was purified by flash-chromatographie (20 g SiO₂, heptane/0-100% EtOAc in 90 min.) to give the title compound (45 mg, 9%).

b) Methyl 2-[3-[[6-(cyclopropylmethoxy)-5-(3,3-difluoroazetidin-1-yl)pyridine-2-carbonyl]amino]thietan-3-yl]acetate

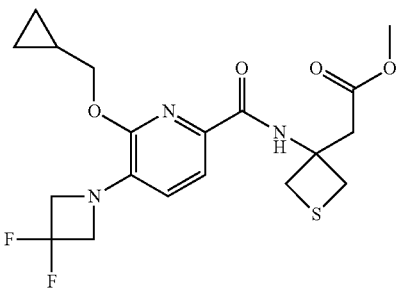 [SMILES: COC(=O)CC1(NC(=O)c2ccc(N3CC(F)(F)C3)c(OCC3CC3)n2)CSC1]

In analogy to the procedure described in Example 86 a), 6-cyclopropylmethoxy-5-(3,3-difluoro-azetidin-1-yl)-pyridine-2-carboxylic acid (Example 2 b, 40 mg, 141 µmol) was condensed with methyl 2-(3-aminothietan-3-yl)acetate (Example 91 a, 25.0 mg, 155 µmol) in the presence of BEP and DIEA to give the title compound (15 mg; 90%) as colorless liquid; MS (ESI) m/e=428.5 [MH⁺].

c) 2-[3-[[6-(Cyclopropylmethoxy)-5-(3,3-difluoroazetidin-1-yl)pyridine-2-carbonyl]amino]thietan-3-yl]acetic acid

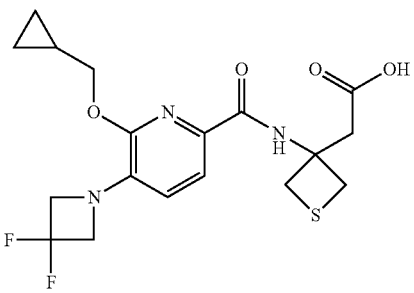 [SMILES: O=C(O)CC1(NC(=O)c2ccc(N3CC(F)(F)C3)c(OCC3CC3)n2)CSC1]

In analogy to the procedure described in Example 65 b), methyl 2-[3-[[6-(cyclopropylmethoxy)-5-(3,3-difluoroazetidin-1-yl)pyridine-2-carbonyl]amino]thietan-3-yl]acetate (Example 91 b, 13 mg, 30.4 µmol) was saponified with lithium hydroxide hydrate to give the title compound (14 mg, quant.) as colorless liquid which was used in the next step without further purification; MS (ESI) m/e=412.4 [M−H⁻].

d) N-[3-(2-Amino-2-oxoethyl)thietan-3-yl]-6-(cyclopropylmethoxy)-5-(3,3-difluoroazetidin-1-yl)pyridine-2-carboxamide In analogy to the procedure described in Example 65 c), 2-[3-[[6-(cyclopropylmethoxy)-5-(3,3-difluoroazetidin-1-yl)pyridine-2-carbonyl]amino]thietan-3-yl]acetic acid (Example 91 c, 14 mg, 33.9 µmol) was reacted with CDI and gaseous NH₃ to obtain the title compound (9 mg, 64%) as colorless liquid; MS (ESI) m/e=413.4 [MH⁺].

Example 92

N-[3-(2-Amino-2-oxoethyl)-1,1-dioxothietan-3-yl]-6-(cyclopropylmethoxy)-5-(1-hydroxycyclobutyl)pyridine-2-carboxamide

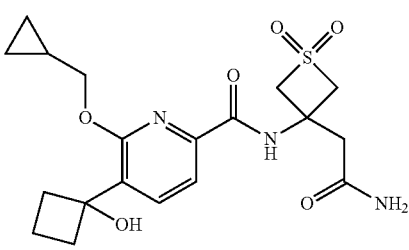 [SMILES: NC(=O)CC1(NC(=O)c2ccc(C3(O)CCC3)c(OCC3CC3)n2)CS(=O)(=O)C1]

a) Methyl 2-[3-[[6-(cyclopropylmethoxy)-5-(1-hydroxycyclobutyl)pyridine-2-carbonyl]amino]-1,1-dioxo-thietan-3-yl]acetate

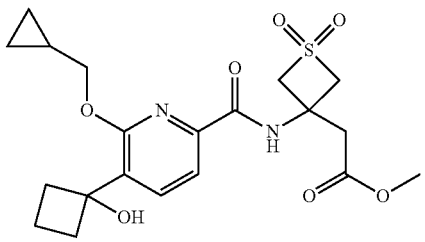 [SMILES: COC(=O)CC1(NC(=O)c2ccc(C3(O)CCC3)c(OCC3CC3)n2)CS(=O)(=O)C1]

In analogy to the procedure described in Example 86 a), 6-(cyclopropylmethoxy)-5-(1-hydroxycyclobutyl)pyridine-2-carboxylic acid (CAN 1415899-53-4, 20 mg, 76.0 µmol) was condensed with methyl 2-(3-amino-1,1-dioxo-thietan-3-yl)acetate (for synthesis of corresponding ethyl ester ethyl 2-(3-amino-1,1-dioxo-thietan-3-yl)acetate see Example 51 c, 26.6 mg, 83.6 µmol) in the presence of BEP and DIEA to give the title compound (36 mg; quant.) as light yellow oil; MS (ESI) m/e=439.3 [MH$^+$].

b) 2-[3-[[6-(Cyclopropylmethoxy)-5-(1-hydroxycyclobutyl)pyridine-2-carbonyl]amino]-1,1-dioxo-thietan-3-yl]acetic acid

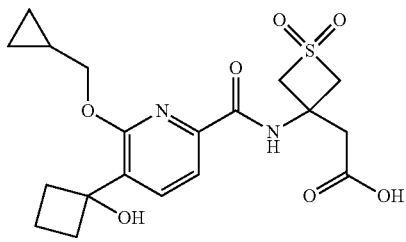 [SMILES: O=C(O)CC1(NC(=O)c2ccc(C3(O)CCC3)c(OCC3CC3)n2)CS(=O)(=O)C1]

In analogy to the procedure described in Example 65 b), methyl 2-[3-[[6-(cyclopropylmethoxy)-5-(1-hydroxycyclobutyl)pyridine-2-carbonyl]amino]-1,1-dioxo-thietan-3-yl]acetate (Example 92 a, 36 mg, 82.1 µmol) was saponified with lithium hydroxide hydrate to give the title compound (30 mg, 86%) as colorless oil which was used in the next step without further purification; MS (ESI) m/e=425.3 [MH$^+$].

c) N-[3-(2-Amino-2-oxoethyl)-1,1-dioxothietan-3-yl]-6-(cyclopropylmethoxy)-5-(1-hydroxycyclobutyl)pyridine-2-carboxamide In analogy to the procedure described in Example 65 c), 2-[3-[[6-(cyclopropylmethoxy)-5-(1-hydroxycyclobutyl)pyridine-2-carbonyl]amino]-1,1-dioxo-thietan-3-yl]acetic acid (Example 92 b, 30 mg, 70.7 µmol) was reacted with CDI and gaseous NH$_3$ to obtain the title compound (12 mg, 40%) as white solid; MS (ESI) m/e=424.3 [MH$^+$].

Example 93

N-[3-(2-Amino-2-oxoethyl)oxetan-3-yl]-6-(cyclopropylmethoxy)-5-(3-fluorooxetan-3-yl)pyridine-2-carboxamide

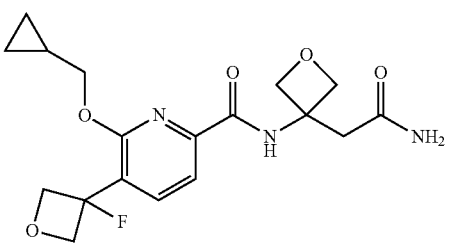

a) 3-(2-Chloro-6-methylpyridin-3-yl)oxetan-3-ol

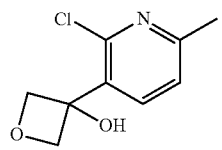

In analogy to the procedure described in Example 89 a), 3-bromo-2-chloro-6-methylpyridine (CAN 185017-72-5, 5 g, 24.2 mmol) was reacted with oxetan-3-one (CAN 6704-31-0, 1.75 g, 1.42 mL, 24.2 mmol) to give the title compound (3.42 g, 71%) as off-white solid, MS (ESI): m/e=200.5 [MH$^+$].

b) 2-Chloro-3-(3-fluorooxetan-3-yl)-6-methylpyridine

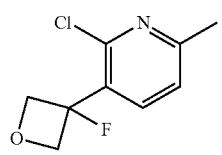

In analogy to the procedure described in Example 89 b), 3-(2-chloro-6-methylpyridin-3-yl)oxetan-3-ol (Example 93 a, 1.5 g, 7.51 mmol) was reacted with diethylaminosulfur trifluoride to obtain the title compound (850 mg, 56%) as colorless liquid, MS (ESI): m/e=202.1 [MH$^+$].

c) 2-Chloro-3-(3-fluorooxetan-3-yl)-6-methylpyridine 1-oxide

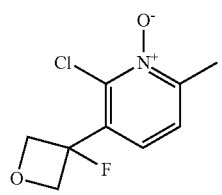

In analogy to the procedure described in Example 89 c), 2-chloro-3-(3-fluorooxetan-3-yl)-6-methylpyridine (Example 93 b, 850 mg, 4.22 mmol) was oxidized to give the title compound (875 mg, 95%) as light brown solid, MS (ESI): m/e=218.4 [MH⁺].

d) (6-Chloro-5-(3-fluorooxetan-3-yl)pyridin-2-yl)methanol

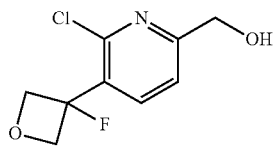 [SMILES: OCc1ccc(C2(F)COC2)c(Cl)n1]

In analogy to the procedure described in Example 89 d), 2-chloro-3-(3-fluorooxetan-3-yl)-6-methylpyridine 1-oxide (Example 93 c, 870 mg, 4 mmol) was rearranged to give the title compound (154 mg, 18%) as colorless liquid, MS (ESI): m/e=218.4 [MH⁺].

e) 6-Chloro-5-(3-fluorooxetan-3-yl)pyridine-2-carboxylic acid

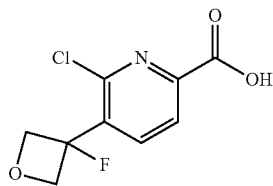 [SMILES: O=C(O)c1ccc(C2(F)COC2)c(Cl)n1]

In analogy to the procedure described in Example 89 e), (6-chloro-5-(3-fluorooxetan-3-yl)pyridin-2-yl)methanol (Example 93 d, 154 mg, 708 μmol) was oxidized to obtain the title compound (66 mg, 40%) as off-white solid, MS(ESI): m/e=232.1 [MH⁺].

f) 6-(Cyclopropylmethoxy)-5-(3-fluorooxetan-3-yl)pyridine-2-carboxylic acid

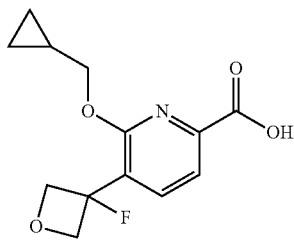 [SMILES: O=C(O)c1ccc(C2(F)COC2)c(OCC2CC2)n1]

6-Chloro-5-(3-fluorooxetan-3-yl)pyridine-2-carboxylic acid (Example 93 e, 44 mg, 190 μmol) and cyclopropylmethanol (CAN 2516-33-8, 17.8 mg, 20.0 μL, 247 μmol) were dissolved in DMF (1.32 mL). A solution of sodium 2-methylpropan-2-olate (42.0 mg, 437 μmol) in THF (800 μL) was added and the mixture was heated to 50° C. for 3 h and for additional 3 h to 70° C. After cooling to ambient temperature, the reaction mixture was poured onto ice/0.1 N HCl (25 mL) and extracted with EtOAc (2×25 mL). The combined extracts were washed with ice/brine (20 mL), dried over Na₂SO₄, filtered and evaporated to dryness. The residue was purified by thin layer chromatography (2 mm SiO₂, dichloromethane/MeOH 19:1, elution with EtOAc) to give the title compound (11 mg, 22%) as colorless oil, MS (ESI) m/e=268.2 [MH⁺].

g) N-[3-(2-Amino-2-oxoethyl)oxetan-3-yl]-6-(cyclopropylmethoxy)-5-(3-fluorooxetan-3-yl)pyridine-2-carboxamide In analogy to the procedure described in Example 86 a), 6-(cyclopropylmethoxy)-5-(3-fluorooxetan-3-yl)pyridine-2-carboxylic acid (Example 93 f, 25 mg, 93.5 μmol) was condensed with 2-(3-amino-oxetan-3-yl)-acetamide (Example 23 a, 14.6 mg, 112 μmol) in the presence of BEP and DIEA to give the title compound (18 mg, 50%) as colorless liquid; MS (ESI) m/e=380.2 [MH⁺].

Example 94

N-[3-(2-Amino-2-oxoethyl)oxetan-3-yl]-6-(cyclopropylmethoxy)-5-(3-hydroxyoxetan-3-yl)pyridine-2-carboxamide

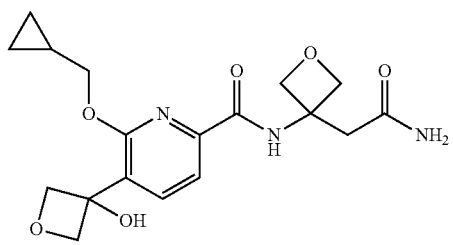 [SMILES: NC(=O)CC1(NC(=O)c2ccc(C3(O)COC3)c(OCC3CC3)n2)COC1]

In analogy to the procedure described in Example 86 a), 6-(cyclopropylmethoxy)-5-(3-hydroxyoxetan-3-yl)pyridine-2-carboxylic acid (CAN 1415899-42-1, 20 mg, 75.4 μmol) was condensed with 2-(3-amino-oxetan-3-yl)-acetamide (Example 23 a, 11.8 mg, 90.5 mol) in the presence of BEP and DIEA to give the title compound (17 mg, 60%) as off-white solid; MS (ESI) m/e=378.3 [MH⁺].

Example 95

N-[3-(2-Amino-2-oxoethyl)thietan-3-yl]-6-(cyclopropylmethoxy)-5-(1-hydroxycyclobutyl)pyridine-2-carboxamide

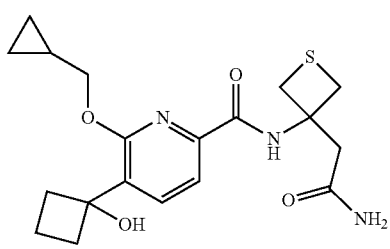 [SMILES: NC(=O)CC1(NC(=O)c2ccc(C3(O)CCC3)c(OCC3CC3)n2)CSC1]

a) Methyl 2-[3-[[6-(cyclopropylmethoxy)-5-(1-hydroxycyclobutyl)pyridine-2-carbonyl]amino]thietan-3-yl]acetate

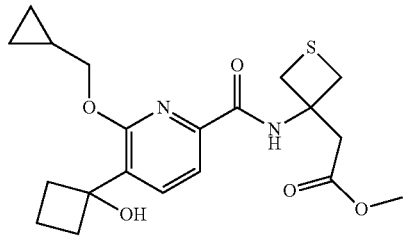 [SMILES: COC(=O)CC1(NC(=O)c2ccc(C3(O)CCC3)c(OCC3CC3)n2)CSC1]

In analogy to the procedure described in Example 86 a), 6-(cyclopropylmethoxy)-5-(1-hydroxycyclobutyl)pyridine-2-carboxylic acid (CAN 1415899-53-4, 30 mg, 114 μmol) was condensed with methyl 2-(3-aminothietan-3-yl)acetate (Example 91 a, 36.7 mg, 114 μmol) in the presence of BEP and DIEA to give the title compound (62 mg; quant.) as brown oil; MS (ESI) m/e=407.3 [MH$^+$].

b) 2-[3-[[6-(Cyclopropylmethoxy)-5-(1-hydroxycyclobutyl)pyridine-2-carbonyl]amino]thietan-3-yl]acetic acid

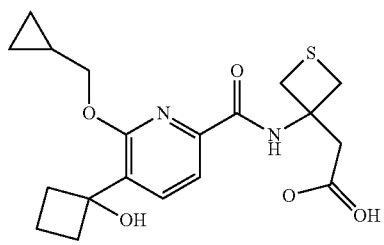 [SMILES: O=C(O)CC1(NC(=O)c2ccc(C3(O)CCC3)c(OCC3CC3)n2)CSC1]

In analogy to the procedure described in Example 65 b), methyl 2-[3-[[6-(cyclopropylmethoxy)-5-(1-hydroxycyclobutyl)pyridine-2-carbonyl]amino]thietan-3-yl]acetate (Example 95 a, 62 mg, 153 μmol) was saponified with lithium hydroxide hydrate to give the title compound (47 mg, 78%) as yellow oil which was used in the next step without further purification; MS (ESI) m/e=393.2 [MH$^+$].

c) N-[3-(2-Amino-2-oxoethyl)thietan-3-yl]-6-(cyclopropylmethoxy)-5-(1-hydroxycyclobutyl)pyridine-2-carboxamide In analogy to the procedure described in Example 65 c), 2-[3-[[6-(cyclopropylmethoxy)-5-(1-hydroxycyclobutyl)pyridine-2-carbonyl]amino]thietan-3-yl]acetic acid (Example 95 b, 47 mg, 120 μmol) was reacted with CDI and gaseous NH$_3$ to obtain the title compound (11 mg, 24%) as white solid; MS (ESI) m/e=392.2 [MH$^+$].

Example 96

N-[3-(2-Amino-2-oxoethyl)thietan-3-yl]-5-cyclopropyl-6-(cyclopropylmethoxy)pyridine-2-carboxamide

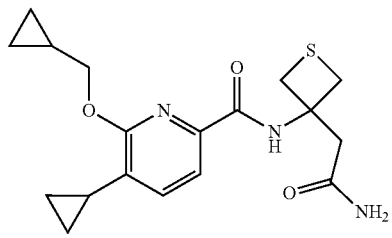 [SMILES: NC(=O)CC1(NC(=O)c2ccc(C3CC3)c(OCC3CC3)n2)CSC1]

a) Methyl 2-[3-[[5-cyclopropyl-6-(cyclopropylmethoxy)pyridine-2-carbonyl]amino]thietan-3-yl]acetate

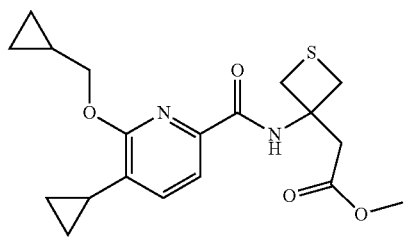 [SMILES: COC(=O)CC1(NC(=O)c2ccc(C3CC3)c(OCC3CC3)n2)CSC1]

In analogy to the procedure described in Example 86 a), 5-cyclopropyl-6-cyclopropylmethoxy-pyridine-2-carboxylic acid (Example 1 c, 30 mg, 129 μmol) was condensed with methyl 2-(3-aminothietan-3-yl)acetate (Example 91 a, 41.5 mg, 129 μmol) in the presence of BEP and DIEA to give the title compound (73 mg; quant.) as brown oil; MS (ESI) m/e=377.2 [MH$^+$].

b) 2-[3-[[5-Cyclopropyl-6-(cyclopropylmethoxy)pyridine-2-carbonyl]amino]thietan-3-yl]acetic acid

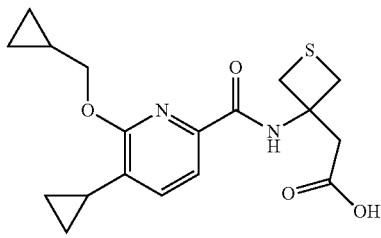 [SMILES: O=C(O)CC1(NC(=O)c2ccc(C3CC3)c(OCC3CC3)n2)CSC1]

In analogy to the procedure described in Example 65 b), methyl 2-[3-[[5-cyclopropyl-6-(cyclopropylmethoxy)pyridine-2-carbonyl]amino]thietan-3-yl]acetate (Example 96 a, 73 mg, 194 μmol) was saponified with lithium hydroxide hydrate to give the title compound (51 mg, 73%) as yellow oil which was used in the next step without further purification; MS (ESI) m/e=363.2 [MH+].

c) N-[3-(2-Amino-2-oxoethyl)thietan-3-yl]-5-cyclopropyl-6-(cyclopropylmethoxy)pyridine-2-carboxamide In analogy to the procedure described in Example 65 c), 2-[3-[[5-cyclopropyl-6-(cyclopropylmethoxy)pyridine-2-carbonyl]amino]thietan-3-yl]acetic acid (Example 96 b, 51 mg, 141 µmol) was reacted with CDI and gaseous NH₃ to obtain the title compound (10 mg, 20%) as white solid; MS (ESI) m/e=362.2 [MH+].

Example 97

N-[3-(2-Amino-2-oxoethyl)thietan-3-yl]-6-(cyclopropylmethoxy)-5-(trifluoromethyl)pyridine-2-carboxamide

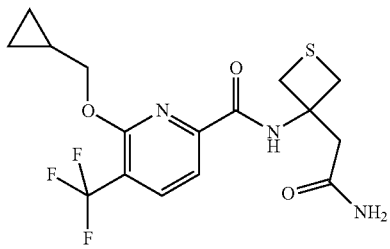 [SMILES: NC(=O)CC1(NC(=O)c2ccc(C(F)(F)F)c(OCC3CC3)n2)CSC1]

a) Methyl 2-[3-[[6-(cyclopropylmethoxy)-5-(trifluoromethyl)pyridine-2-carbonyl]amino]thietan-3-yl]acetate

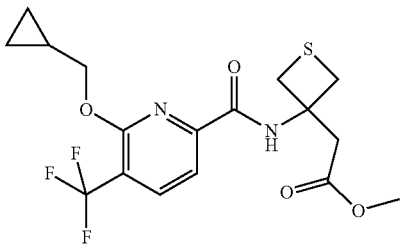 [SMILES: COC(=O)CC1(NC(=O)c2ccc(C(F)(F)F)c(OCC3CC3)n2)CSC1]

In analogy to the procedure described in Example 86 a), 6-cyclopropylmethoxy-5-trifluoromethyl-pyridine-2-carboxylic acid (Example 39 d, 30 mg, 115 µmol) was condensed with methyl 2-(3-aminothietan-3-yl)acetate (Example 91 a, 37 mg, 115 µmol) in the presence of BEP and DIEA to give the title compound (52 mg; quant.) as brown oil; MS (ESI) m/e=405.2 [MH+].

b) 2-[3-[[6-(Cyclopropylmethoxy)-5-(trifluoromethyl)pyridine-2-carbonyl]amino]thietan-3-yl]acetic acid

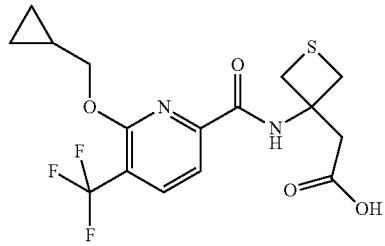 [SMILES: O=C(O)CC1(NC(=O)c2ccc(C(F)(F)F)c(OCC3CC3)n2)CSC1]

In analogy to the procedure described in Example 65 b), methyl 2-[3-[[6-(cyclopropylmethoxy)-5-(trifluoromethyl)pyridine-2-carbonyl]amino]thietan-3-yl]acetate (Example 97 a, 52 mg, 129 µmol) was saponified with lithium hydroxide hydrate to give the title compound (53 mg, quant.) as yellow oil which was used in the next step without further purification; MS (ESI) m/e=391.1 [MH+].

c) N-[3-(2-Amino-2-oxoethyl)thietan-3-yl]-6-(cyclopropylmethoxy)-5-(trifluoromethyl)pyridine-2-carboxamide In analogy to the procedure described in Example 65 c), 2-[3-[[6-(cyclopropylmethoxy)-5-(trifluoromethyl)pyridine-2-carbonyl]amino]thietan-3-yl]acetic acid (Example 97 b, 53 mg, 136 µmol) was reacted with CDI and gaseous NH₃ to obtain the title compound (9 mg, 17%) as white solid; MS (ESI) m/e=390.2 [MH+].

Example 98

N-[3-(2-Amino-2-oxoethyl)thietan-3-yl]-6-(cyclopropylmethoxy)-5-(3-fluorooxetan-3-yl)pyridine-2-carboxamide

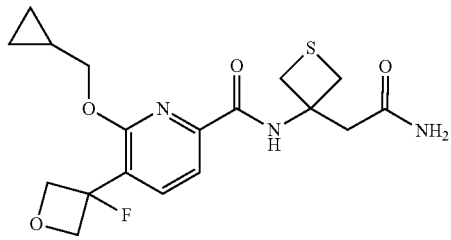 [SMILES: NC(=O)CC1(NC(=O)c2ccc(C3(F)COC3)c(OCC3CC3)n2)CSC1]

a) Methyl 2-[3-[[6-(cyclopropylmethoxy)-5-(3-fluorooxetan-3-yl)pyridine-2-carbonyl]amino]thietan-3-yl]acetate

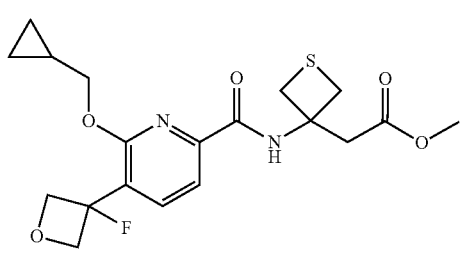 [SMILES: COC(=O)CC1(NC(=O)c2ccc(C3(F)COC3)c(OCC3CC3)n2)CSC1]

In analogy to the procedure described in Example 86 a), 6-(cyclopropylmethoxy)-5-(3-fluorooxetan-3-yl)pyridine-2-carboxylic acid (Example 93 f, 100 mg, 374 μmol) was condensed with methyl 2-(3-aminothietan-3-yl)acetate (Example 91 a, 219 mg, 681 μmol) in the presence of BEP and DIEA to give the title compound (43 mg; 13%) as light brown liquid; MS (ESI) m/e=411.3 [MH⁺].

b) 2-[3-[[6-(Cyclopropylmethoxy)-5-(3-fluorooxetan-3-yl)pyridine-2-carbonyl]amino]thietan-3-yl]acetic acid

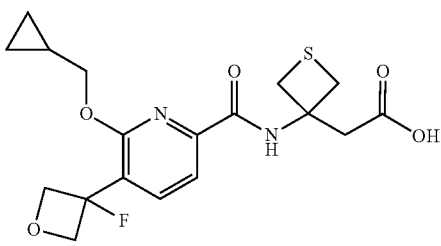 [SMILES: O=C(O)CC1(NC(=O)c2ccc(C3(F)COC3)c(OCC3CC3)n2)CSC1]

In analogy to the procedure described in Example 65 b), methyl 2-[3-[[6-(cyclopropylmethoxy)-5-(3-fluorooxetan-3-yl)pyridine-2-carbonyl]amino]thietan-3-yl]acetate (Example 98 a, 43 mg, 105 μmol) was saponified with lithium hydroxide hydrate to give the title compound (36 mg, 87%) as yellow oil which was used in the next step without further purification; MS (ESI) m/e=351.3 [M−HCO₂⁺].

c) N-[3-(2-Amino-2-oxoethyl)thietan-3-yl]-6-(cyclopropylmethoxy)-5-(3-fluorooxetan-3-yl)pyridine-2-carboxamide In analogy to the procedure described in Example 65 c), 2-[3-[[6-(cyclopropylmethoxy)-5-(3-fluorooxetan-3-yl)pyridine-2-carbonyl]amino]thietan-3-yl]acetic acid (Example 98 b, 36 mg, 90.8 μmol) was reacted with CDI and gaseous NH₃ to obtain the title compound (19 mg, 53%) as white solid; MS (ESI) m/e=396.2 [MH⁺].

Example 99

Pharmacological tests

The following tests were carried out in order to determine the activity of the compounds of formula I:
Radioligand Binding Assay The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl₂, 2.5 mM EDTA, and 0.5% (wt/vol) fatty acid free BSA, pH 7.4 for CB1 receptor and 50 mM Tris, 5 mM MgCl₂, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55, 940 determined from saturation experiments. The compounds of formula (I) show an excellent affinity for the CB2 receptor with affinities below 10 μM, more particularly of 1 nM to 3 μM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% CO₂ and 37° C. in a humidified incubator. The growth medium was exchanged with Krebs Ringer Bicarbonate buffer with 1 mM IBMX and incubated at 30° C. for 30 min. Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% NaN₃) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

The compounds of the invention are CB2 receptor agonists with $EC_{50}$ below 1 μM and selectivity versus CB1 in the corresponding assay of at least 10 fold. Particular compound of the invention are CB2 receptor agonists with $EC_{50}$ below 0.05 μM and selectivity versus CB1 in the corresponding assay of at least 500 fold.

For example, the following compounds showed the following human $EC_{50}$ values in the functional cAMP assay described above:

| Example | human CB2 $EC_{50}$ [μM] | human CB1 $EC_{50}$ [μM] |
| --- | --- | --- |
| 1 | 0.0537 | >10 |
| 2 | 0.6757 | >10 |
| 3 | 0.846 | >10 |
| 4 | 0.0042 | >10 |
| 5 | 0.5184 | >10 |
| 6 | 0.1722 | >10 |
| 7 | 0.0556 | >10 |
| 8 | 0.301 | >10 |
| 9 | 0.0021 | >10 |
| 10 | 0.0003 | 0.1332 |
| 11 | 0.9667 | >10 |
| 12 | 0.0159 | >10 |
| 13 | 0.005 | >10 |
| 14 | 0.0015 | 0.4449 |
| 15 | 0.0049 | >10 |
| 16 | 0.0019 | 0.1716 |
| 17 | 0.0062 | >10 |

| Example | human CB2 EC$_{50}$ [μM] | human CB1 EC$_{50}$ [μM] |
|---|---|---|
| 18 | 0.0015 | >10 |
| 19 | 0.0032 | >10 |
| 20 | 0.0158 | >10 |
| 21 | 0.4069 | >10 |
| 22 | 0.0119 | >10 |
| 23 | 0.0014 | >10 |
| 24 | 0.003 | >10 |
| 25 | 0.0043 | >10 |
| 26 | 0.00565 | >10 |
| 27 | 0.0014 | >10 |
| 28 | 0.003 | >10 |
| 29 | 0.0232 | >10 |
| 30 | 0.0083 | >10 |
| 31 | 0.0088 | >10 |
| 32 | 0.1371 | >10 |
| 33 | 0.1446 | >10 |
| 34 | 0.0022 | >10 |
| 35 | 0.0006 | 0.2087 |
| 36 | 0.2554 | >10 |
| 37 | 0.3627 | >10 |
| 38 | 0.1008 | >10 |
| 39 | 0.5994 | >10 |
| 40 | 0.3447 | >10 |
| 41 | 0.298 | >10 |
| 42 | 0.9671 | >10 |
| 43 | 0.1051 | >10 |
| 44 | 0.4132 | >10 |
| 45 | 0.2371 | >10 |
| 46 | 0.0314 | >10 |
| 47 | 0.7932 | >10 |
| 48 | 0.0092 | >10 |
| 49 | 0.0127 | >10 |
| 50 | 0.4229 | >10 |
| 51 | 0.057 | >10 |
| 52 | 0.0749 | >10 |
| 53 | 0.018 | >10 |
| 54 | 0.055 | >10 |
| 55 | 0.003 | >10 |
| 56 | 0.003 | >10 |
| 57 | 0.003 | >10 |
| 58 | 0.018 | >10 |
| 59 | 0.0552 | >10 |
| 60 | 0.0026 | >10 |
| 61 | 0.001 | 7.75 |
| 62 | 0.0025 | >10 |
| 63 | 0.0555 | >10 |
| 64 | 0.0052 | >10 |
| 65 | 0.4432 | >10 |
| 66 | 0.0013 | >10 |
| 67 | 0.0083 | >10 |
| 68 | 0.0011 | >10 |
| 69 | 0.3022 | >10 |
| 70 | 0.0006 | >10 |
| 71 | 0.0606 | >10 |
| 72 | 0.005 | >10 |
| 73 | 0.1202 | >10 |
| 74 | 0.039 | >10 |
| 75 | 0.0158 | >10 |
| 76 | 0.0001 | 5.5 |
| 77 | 0.0007 | >10 |
| 78 | 0.041 | >10 |
| 79 | 0.0747 | >10 |
| 80 | 0.0024 | >10 |
| 81 | 0.015 | >10 |
| 82 | 0.0015 | >10 |
| 83 | 1.3268 | >10 |
| 84 | 0.0676 | >10 |
| 85 | 0.2702 | >10 |
| 86 | 0.2396 | >10 |
| 87 | 0.0003 | 0.0348 |
| 88 | 0.002 | >10 |
| 89 | 0.0119 | >10 |
| 90 | 0.0088 | >10 |
| 91 | 0 | >10 |
| 92 | 0.0022 | >10 |
| 93 | 0.0149 | >10 |
| 94 | 0.2509 | >10 |
| 95 | 0.0011 | >10 |
| 96 | 0.0018 | >10 |
| 97 | 0.0115 | >10 |
| 98 | 0.0012 | >10 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

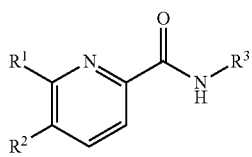

wherein
- $R^1$ is halogen, cycloalkylalkoxy, haloalkoxy, alkylsulfonyl, alkylsulfinyl, halophenylalkyl, alkylsulfanyl, oxanylalkoxy, halophenyl or oxolanylalkoxy;
- $R^2$ is halogen, cycloalkyl, haloalkyl, haloalkoxy, haloazetidinyl, cycloalkyloxy, halocycloalkyl, hydroxycycloalkyl, hydroxyazetidinyl, hydroxyoxetanyl or halooxetanyl;
- $R^3$ is (alkyl)(oxo)pyrrolidinyl or —$C(R^4R^5)$—$C(R^6R^7)$—$C(O)$—$R^8$;
- $R^4$ and $R^5$ are independently selected from hydrogen, alkyl, phenyl, phenylalkyl, cycloalkyl, tetrahydropyranyl, haloalkyl, halophenyl and oxolanyl;
- or $R^4$ and $R^5$ together with the carbon atom to which they are attached form cycloalkyl, oxetanyl, thiethanyl, 1,1-dioxo-1λ6-thiethanyl, azetidinyl, haloazetidinyl, 2-oxa-spiro[3.3]heptyl, tetrahydrofuranyl, pyrrolidinyl, oxopyrrolidinyl, 1,1-dioxo-1λ6-isothiazolidinyl, 1,1-dioxo-tetrahydro-1λ6-thiophenyl, tetrahydrothiophenyl, tetrahydropyranyl, piperidinyl, oxopiperidinyl, tetrahydrothiopyranyl, 2-oxo-[1,3]oxazinanyl, 1,1-dioxo-1λ6-[1,2]thiazinanyl, 2-oxo-hexahydro-pyrimidinyl, 1,1-dioxo-hexahydro-1λ6-thiopyranyl, 2-oxo-[1,3]dioxanyl, 1,1-dioxothianyl, alkylcarbonylpiperidinyl, alkylcarbonylazetidinyl, phenylalkyloxycarbonylazetidinyl, oxolanyl, or phenylalkyloxycarbonylpyrrolidinyl;
- $R^6$ and $R^7$ are independently selected from hydrogen and alkyl;
- or one of $R^4$ and $R^5$ and one of $R^6$ and $R^7$, together with the carbon atoms to which they are attached, form cycloalkyl, and the other ones are both hydrogen at the same time; and
- $R^8$ is —$NH_2$, alkoxy, alkylamino or hydroxyl;
- or a pharmaceutically acceptable salt or ester thereof.

2. A compound according to claim 1, wherein $R^1$ is cycloalkylalkoxy, haloalkoxy, halophenylalkyl or oxolanylalkoxy.

3. A compound according to claim 1, wherein $R^1$ is cyclopropylmethoxy, pentafluoropropyloxy, fluorophenylmethyl or oxolanylmethoxy.

4. A compound according to claim 1, wherein $R^2$ is cycloalkyl, haloazetidinyl, halocycloalkyl, hydroxycycloalkyl, haloalkyl or halooxetanyl.

5. A compound according to claim 1, wherein $R^2$ is cyclopropyl, difluoroazetidinyl, fluorocyclobutyl, hydroxycyclobutyl or trifluoromethyl.

6. A compound according to claim 1, wherein $R^3$ is —$C(R^4R^5)$—$C(R^6R^7)$—$C(O)$—$R^8$.

7. A compound according to claim 1, wherein one of $R^4$ and $R^5$ is hydrogen or alkyl, and the other one is independently selected from alkyl, haloalkyl, phenyl, cycloalkyl and tetrahydropyranyl.

8. A compound according to claim 1, wherein one of $R^4$ and $R^5$ is hydrogen or methyl, and the other one is independently selected from methyl, trifluoromethyl, phenyl, cyclohexyl, cyclopropyl and tetrahydropyranyl.

9. A compound according to claim 1, wherein $R^4$ and $R^5$ together with the carbon atom to which they are attached form oxetanyl, 1,1-dioxo-1λ6-thiethanyl, piperidinyl, cycloalkyl, oxolanyl or thiethanyl.

10. A compound according to claim 1, wherein $R^6$ and $R^7$ are both hydrogen at the same time.

11. A compound according to claim 1, wherein one of $R^4$ and $R^5$ and one of $R^6$ and $R^7$, together with the carbon atoms to which they are attached, form cyclohexyl, and the other ones are both hydrogen at the same time.

12. A compound according to claim 1, wherein $R^8$ is —$NH_2$ or ethoxy.

13. A compound according to claim 1 selected from
- {3-[(5-Cyclopropyl-6-cyclopropylmethoxy-pyridine-2-carbonyl)-amino]-oxetan-3-yl}-acetic acid ethyl ester;
- tert-Butyl 3-({[6-(cyclopropylmethoxy)-5-(3,3-difluoro-azetidin-1-yl)pyridin-2-yl]carbonyl}amino)-5-methyl-hexanoate;
- 6-Cyclopropylmethoxy-5-(3,3-difluoro-azetidin-1-yl)-pyridine-2-carboxylic acid (1-methyl-5-oxo-pyrrolidin-3-yl)-amide;
- 3-{[6-Cyclopropylmethoxy-5-(3,3-difluoro-azetidin-1-yl)-pyridine-2-carbonyl]-amino}-3-phenyl-propionic acid ethyl ester;
- 3-{[6-Cyclopropylmethoxy-5-(3,3-difluoro-azetidin-1-yl)-pyridine-2-carbonyl]-amino}-3-methyl-butyric acid ethyl ester;
- 6-Cyclopropylmethoxy-5-(3,3-difluoro-azetidin-1-yl)-pyridine-2-carboxylic acid (1,1-dimethyl-2-methylcarbamoyl-ethyl)-amide;
- 6-Cyclopropylmethoxy-5-(3,3-difluoro-azetidin-1-yl)-pyridine-2-carboxylic acid (1-methylcarbamoylmethyl-hexyl)-amide;
- 6-Cyclopropylmethoxy-5-(3,3-difluoro-azetidin-1-yl)-pyridine-2-carboxylic acid (1-methylcarbamoylmethyl-3-phenyl-propyl)-amide;
- (−)-5-Cyclopropyl-6-cyclopropylmethoxy-pyridine-2-carboxylic acid (1-carbamoylmethyl-pentyl)-amide;
- (+)-5-Cyclopropyl-6-cyclopropylmethoxy-pyridine-2-carboxylic acid (1-carbamoylmethyl-pentyl)-amide;
- 2-[({[6-(Cyclopropylmethoxy)-5-(3,3-difluoroazetidin-1-yl)pyridin-2-yl]carbonyl}amino)methyl]-4-methylpentanoic acid;
- 5-Cyclopropyl-6-cyclopropylmethoxy-pyridine-2-carboxylic acid (rel-(1S,2R)-2-carbamoyl-cyclohexyl)-amide;
- 5-Cyclopropyl-6-cyclopropylmethoxy-pyridine-2-carboxylic acid ((R)-1-carbamoylmethyl-2-methyl-propyl)-amide;
- 5-Cyclopropyl-6-cyclopropylmethoxy-pyridine-2-carboxylic acid ((S)-1-carbamoylmethyl-2-methyl-propyl)-amide;
- (+)-cis-5-Cyclopropyl-6-cyclopropylmethoxy-pyridine-2-carboxylic acid (2-carbamoyl-cyclohexyl)-amide;
- (−)-trans-5-Cyclopropyl-6-cyclopropylmethoxy-pyridine-2-carboxylic acid (−2-carbamoyl-cyclohexyl)-amide;

(−)-5-Cyclopropyl-6-cyclopropylmethoxy-pyridine-2-carboxylic acid (2-carbamoyl-1-cyclohexyl-ethyl)-amide;
(+)-5-Cyclopropyl-6-cyclopropylmethoxy-pyridine-2-carboxylic acid (2-carbamoyl-1-cyclohexyl-ethyl)-amide;
6-Cyclopropylmethoxy-5-(3,3-difluoro-azetidin-1-yl)-pyridine-2-carboxylic acid ((S)-1-carbamoylmethyl-2-methyl-propyl)-amide;
(+)-cis-6-Cyclopropylmethoxy-5-(3,3-difluoro-azetidin-1-yl)-pyridine-2-carboxylic acid (2-carbamoyl-cyclohexyl)-amide;
(−)-cis-6-Cyclopropylmethoxy-5-(3,3-difluoro-azetidin-1-yl)-pyridine-2-carboxylic acid (2-carbamoyl-cyclohexyl)-amide;
3-[(5-Cyclopropyl-6-cyclopropylmethoxy-pyridine-2-carbonyl)-amino]-5-methyl-hexanoic acid ethyl ester;
5-Cyclopropyl-6-cyclopropylmethoxy-pyridine-2-carboxylic acid (3-carbamoylmethyl-oxetan-3-yl)-amide;
(−)-5-Cyclopropyl-6-cyclopropylmethoxy-pyridine-2-carboxylic acid (1-carbamoylmethyl-3-methyl-butyl)-amide;
(+)-5-Cyclopropyl-6-cyclopropylmethoxy-pyridine-2-carboxylic acid (1-carbamoylmethyl-3-methyl-butyl)-amide;
6-Cyclopropylmethoxy-5-(3,3-difluoro-azetidin-1-yl)-pyridine-2-carboxylic acid (3-carbamoylmethyl-oxetan-3-yl)-amide;
(−)-5-Cyclopropyl-6-cyclopropylmethoxy-pyridine-2-carboxylic acid (2-carbamoyl-1-cyclopropyl-ethyl)-amide;
(+)-5-Cyclopropyl-6-cyclopropylmethoxy-pyridine-2-carboxylic acid (2-carbamoyl-1-cyclopropyl-ethyl)-amide;
5-Cyclopropyl-6-cyclopropylmethoxy-pyridine-2-carboxylic acid ((R)-1-carbamoylmethyl-2,2-dimethyl-propyl)-amide;
5-Cyclopropyl-6-cyclopropylmethoxy-pyridine-2-carboxylic acid [2-carbamoyl-1-(tetrahydro-pyran-4-yl)-ethyl]-amide;
(−)-5-Cyclopropyl-6-cyclopropylmethoxy-pyridine-2-carboxylic acid (1-carbamoylmethyl-2,2,2-trifluoro-ethyl)-amide;
(+)-5-Cyclopropyl-6-cyclopropylmethoxy-pyridine-2-carboxylic acid (1-carbamoylmethyl-2,2,2-trifluoro-ethyl)-amide;
5-Cyclopropyl-6-(2,2,2-trifluoro-1-methyl-ethoxy)-pyridine-2-carboxylic acid (3-carbamoylmethyl-oxetan-3-yl)-amide;
(−)-5-Cyclopropyl-6-cyclopropylmethoxy-pyridine-2-carboxylic acid [2-carbamoyl-1-(tetrahydro-pyran-4-yl)-ethyl]-amide;
5-Cyclopropyl-6-cyclopropylmethoxy-pyridine-2-carboxylic acid ((S)-1-carbamoylmethyl-2,2-dimethyl-propyl)-amide;
5-Cyclopropyl-6-(2-methyl-propane-1-sulfonyl)-pyridine-2-carboxylic acid (3-carbamoylmethyl-oxetan-3-yl)-amide;
6-Cyclopropylmethoxy-5-(3,3-difluoro-azetidin-1-yl)-pyridine-2-carboxylic acid (3-methylcarbamoylmethyl-oxetan-3-yl)-amide;
5-Cyclopropyl-6-cyclopropylmethoxy-pyridine-2-carboxylic acid (3-methylcarbamoylmethyl-oxetan-3-yl)-amide;
6-Cyclopropylmethoxy-5-trifluoromethyl-pyridine-2-carboxylic acid (3-methylcarbamoylmethyl-oxetan-3-yl)-amide;
5-Cyclopropyl-6-cyclopropylmethoxy-pyridine-2-carboxylic acid (3-dimethylcarbamoylmethyl-oxetan-3-yl)-amide;
6-Cyclopropylmethoxy-5-(3,3-difluoro-azetidin-1-yl)-pyridine-2-carboxylic acid (3-dimethylcarbamoylmethyl-oxetan-3-yl)-amide;
6-Cyclopropylmethoxy-5-trifluoromethyl-pyridine-2-carboxylic acid (3-dimethylcarbamoylmethyl-oxetan-3-yl)-amide;
5-Cyclopropyl-6-cyclopropylmethoxy-pyridine-2-carboxylic acid [(R)-2-carbamoyl-1-(3-chloro-phenyl)-ethyl]-amide;
5-Bromo-6-(propane-2-sulfinyl)-pyridine-2-carboxylic acid (3-carbamoylmethyl-oxetan-3-yl)-amide;
4-[(5-Cyclopropyl-6-cyclopropylmethoxy-pyridine-2-carbonyl)-amino]-4-methoxycarbonylmethyl-piperidine-1-carboxylic acid tert-butyl ester;
6-Cyclopropylmethoxy-5-trifluoromethoxy-pyridine-2-carboxylic acid (3-carbamoylmethyl-oxetan-3-yl)-amide;
6-Chloro-5-cyclopropylmethoxy-pyridine-2-carboxylic acid (3-carbamoylmethyl-oxetan-3-yl)-amide;
6-Cyclopropylmethoxy-5-(3,3-difluoro-azetidin-1-yl)-pyridine-2-carboxylic acid (2-carbamoyl-1,1-dimethyl-ethyl)-amide;
5-Cyclopropyl-6-(2,2,3,3,3-pentafluoro-propoxy)-pyridine-2-carboxylic acid (3-carbamoylmethyl-oxetan-3-yl)-amide;
(3-{[6-Cyclopropylmethoxy-5-(3,3-difluoro-azetidin-1-yl)-pyridine-2-carbonyl]-amino}-5-oxo-pyrrolidin-3-yl)-acetic acid methyl ester;
(3-{[6-Cyclopropylmethoxy-5-(3,3-difluoro-azetidin-1-yl)-pyridine-2-carbonyl]-amino}-1,1-dioxo-1λ6-thietan-3-yl)-acetic acid ethyl ester;
(4-{[6-Cyclopropylmethoxy-5-(3,3-difluoro-azetidin-1-yl)-pyridine-2-carbonyl]-amino}-tetrahydro-pyran-4-yl)-acetic acid methyl ester;
6-Cyclopropylmethoxy-5-(3,3-difluoro-azetidin-1-yl)-pyridine-2-carboxylic acid [2-carbamoyl-1-(tetrahydro-pyran-4-yl)-ethyl]-amide;
6-Cyclopropylmethoxy-5-(3,3-difluoro-azetidin-1-yl)-pyridine-2-carboxylic acid (3-carbamoylmethyl-5-oxo-pyrrolidin-3-yl)-amide;
6-Cyclopropylmethoxy-5-(3,3-difluoro-azetidin-1-yl)-pyridine-2-carboxylic acid (1-carbamoylmethyl-2,2,2-trifluoro-ethyl)-amide;
(3-{[6-Cyclopropylmethoxy-5-(3,3-difluoro-azetidin-1-yl)-pyridine-2-carbonyl]-amino}-1,1-dioxo-1λ6-thietan-3-yl)-acetic acid;
(4-{[6-Cyclopropylmethoxy-5-(3,3-difluoro-azetidin-1-yl)-pyridine-2-carbonyl]-amino}-tetrahydro-pyran-4-yl)-acetic acid;
(−)-6-Cyclopropylmethoxy-5-(3,3-difluoro-azetidin-1-yl)-pyridine-2-carboxylic acid [2-carbamoyl-1-(tetrahydro-pyran-4-yl)-ethyl]-amide;
(+)-6-Cyclopropylmethoxy-5-(3,3-difluoro-azetidin-1-yl)-pyridine-2-carboxylic acid [(S)-2-carbamoyl-1-(tetrahydro-pyran-4-yl)-ethyl]-amide;
6-Cyclopropylmethoxy-5-(3,3-difluoro-azetidin-1-yl)-pyridine-2-carboxylic acid (4-carbamoylmethyl-tetrahydro-pyran-4-yl)-amide;
6-Cyclopropylmethoxy-5-(3,3-difluoro-azetidin-1-yl)-pyridine-2-carboxylic acid (3-carbamoylmethyl-1,1-dioxo-1λ6-thietan-3-yl)-amide;
6-Cyclopropylmethoxy-5-(3,3-difluoro-azetidin-1-yl)-pyridine-2-carboxylic acid (4-carbamoylmethyl-tetrahydro-thiopyran-4-yl)-amide;

6-Cyclopropylmethoxy-5-(3,3-difluoro-azetidin-1-yl)-pyridine-2-carboxylic acid (1-carbamoylmethyl-cyclobutyl)-amide;
6-Cyclopropylmethoxy-5-(3,3-difluoro-azetidin-1-yl)-pyridine-2-carboxylic acid (3-carbamoylmethyl-thietan-3-yl)-amide;
6-Cyclopropylmethoxy-5-(3,3-difluoro-azetidin-1-yl)-pyridine-2-carboxylic acid (3-carbamoylmethyl-azetidin-3-yl)-amide;
6-Cyclopropylmethoxy-5-(3,3-difluoro-azetidin-1-yl)-pyridine-2-carboxylic acid (1-carbamoylmethyl-3,3-difluoro-cyclobutyl)-amide;
6-Cyclopropylmethoxy-5-(3,3-difluoro-azetidin-1-yl)-pyridine-2-carboxylic acid (6-carbamoylmethyl-2-oxa-spiro[3.3]hept-6-yl)-amide;
6-Cyclopropylmethoxy-5-(3,3-difluoro-azetidin-1-yl)-pyridine-2-carboxylic acid (3-carbamoylmethyl-tetrahydro-furan-3-yl)-amide;
6-Cyclopropylmethoxy-5-(3,3-difluoro-azetidin-1-yl)-pyridine-2-carboxylic acid (3-carbamoylmethyl-pyrrolidin-3-yl)-amide;
6-Cyclopropylmethoxy-5-(3,3-difluoro-azetidin-1-yl)-pyridine-2-carboxylic acid (4-carbamoylmethyl-1,1-dioxo-1$\lambda$6-isothiazolidin-4-yl)-amide;
6-Cyclopropylmethoxy-5-(3,3-difluoro-azetidin-1-yl)-pyridine-2-carboxylic acid (3-carbamoylmethyl-1,1-dioxo-tetrahydro-1$\lambda$6-thiophen-3-yl)-amide;
6-Cyclopropylmethoxy-5-(3,3-difluoro-azetidin-1-yl)-pyridine-2-carboxylic acid (3-carbamoylmethyl-tetrahydro-thiophen-3-yl)-amide;
6-Cyclopropylmethoxy-5-(3,3-difluoro-azetidin-1-yl)-pyridine-2-carboxylic acid (4-carbamoylmethyl-piperidin-4-yl)-amide;
6-Cyclopropylmethoxy-5-(3,3-difluoro-azetidin-1-yl)-pyridine-2-carboxylic acid (4-carbamoylmethyl-2-oxo-piperidin-4-yl)-amide;
6-Cyclopropylmethoxy-5-(3,3-difluoro-azetidin-1-yl)-pyridine-2-carboxylic acid (5-carbamoylmethyl-2-oxo-[1,3]oxazinan-5-yl)-amide;
6-Cyclopropylmethoxy-5-(3,3-difluoro-azetidin-1-yl)-pyridine-2-carboxylic acid (4-carbamoylmethyl-1,1-dioxo-hexahydro-1$\lambda$6-thiopyran-4-yl)-amide;
6-Cyclopropylmethoxy-5-(3,3-difluoro-azetidin-1-yl)-pyridine-2-carboxylic acid (4-carbamoylmethyl-1,1-dioxo-1$\lambda$6-[1,2]thiazinan-4-yl)-amide;
6-Cyclopropylmethoxy-5-(3,3-difluoro-azetidin-1-yl)-pyridine-2-carboxylic acid (3-carbamoylmethyl-6-oxo-piperidin-3-yl)-amide;
6-Cyclopropylmethoxy-5-(3,3-difluoro-azetidin-1-yl)-pyridine-2-carboxylic acid (5-carbamoylmethyl-2-oxo-hexahydro-pyrimidin-5-yl)-amide;
6-Cyclopropylmethoxy-5-(3,3-difluoro-azetidin-1-yl)-pyridine-2-carboxylic acid (3-carbamoylmethyl-1,1-dioxo-hexahydro-1$\lambda$6-thiopyran-3-yl)-amide;
6-Cyclopropylmethoxy-5-(3,3-difluoro-azetidin-1-yl)-pyridine-2-carboxylic acid (5-carbamoylmethyl-2-oxo-[1,3]dioxan-5-yl)-amide;
6-Cyclopropylmethoxy-5-(3,3-difluoro-azetidin-1-yl)-pyridine-2-carboxylic acid (3-carbamoylmethyl-tetrahydro-pyran-3-yl)-amide;
6-Cyclopropylmethoxy-5-(3,3-difluoro-azetidin-1-yl)-pyridine-2-carboxylic acid (3-carbamoylmethyl-piperidin-3-yl)-amide;
6-Cyclopropylmethoxy-5-(3,3-difluoro-azetidin-1-yl)-pyridine-2-carboxylic acid (3-carbamoylmethyl-tetrahydro-thiopyran-3-yl)-amide;
6-Cyclopropylmethoxy-5-(3,3-difluoro-azetidin-1-yl)-pyridine-2-carboxylic acid (5-carbamoylmethyl-1,1-dioxo-1$\lambda$6-[1,2]thiazinan-5-yl)-amide;
N-[4-(2-Amino-2-oxoethyl)-1,1-dioxothian-4-yl]-6-(cyclopropylmethoxy)-5-(3,3-difluoroazetidin-1-yl)pyridine-2-carboxamide;
N-[3-Amino-3-oxo-1-(oxolan-3-yl)propyl]-5-cyclopropyl-6-(cyclopropylmethoxy)pyridine-2-carboxamide;
N-[3-(2-Amino-2-oxoethyl)azetidin-3-yl]-6-(cyclopropylmethoxy)-5-(3,3-difluoroazetidin-1-yl)pyridine-2-carboxamide;
N-[4-(2-Amino-2-oxoethyl)piperidin-4-yl]-5-cyclopropyl-6-[(4-fluorophenyl)methyl]pyridine-2-carboxamide; hydrochloride;
N-[3-Amino-3-oxo-1-(oxolan-3-yl)propyl]-6-(cyclopropylmethoxy)-5-(3,3-difluoroazetidin-1-yl)pyridine-2-carboxamide;
Methyl 2-[1-[[6-(cyclopropylmethoxy)-5-(3,3-difluoroazetidin-1-yl)pyridine-2-carbonyl]amino]cyclobutyl]acetate;
2-[1-[[6-(Cyclopropylmethoxy)-5-(3,3-difluoroazetidin-1-yl)pyridine-2-carbonyl]amino]cyclobutyl]acetic acid;
N-[1-(2-Amino-2-oxoethyl)cyclobutyl]-6-(cyclopropylmethoxy)-5-(3,3-difluoroazetidin-1-yl)pyridine-2-carboxamide;
Ethyl 1-[[[6-(cyclopropylmethoxy)-5-(3,3-difluoroazetidin-1-yl)pyridine-2-carbonyl]amino]methyl]cyclopropane-1-carboxylate;
N-[1-Acetyl-4-(2-amino-2-oxoethyl)piperidin-4-yl]-5-cyclopropyl-6-[(4-fluorophenyl)methyl]pyridine-2-carboxamide;
N-[1-Acetyl-3-(2-amino-2-oxoethyl)azetidin-3-yl]-6-(cyclopropylmethoxy)-5-(3,3-difluoroazetidin-1-yl)pyridine-2-carboxamide;
Benzyl 3-(2-amino-2-oxoethyl)-3-[[5-cyclopropyl-6-[(4-fluorophenyl)methyl]pyridine-2-carbonyl]amino]azetidine-1-carboxylate;
N-[3-(2-Amino-2-oxoethyl)-1,1-dioxothietan-3-yl]-5-cyclopropyl-6-(2-methylpropylsulfanyl)pyridine-2-carboxamide;
N-[3-(2-Amino-2-oxoethyl)-1,1-dioxothietan-3-yl]-5-cyclopropyl-6-[(4-fluorophenyl)methyl]pyridine-2-carboxamide;
N-[3-(2-Amino-2-oxoethyl)-1,1-dioxothietan-3-yl]-5-cyclopropyl-6-(cyclopropylmethoxy)pyridine-2-carboxamide;
N-[3-(2-Amino-2-oxoethyl)-1,1-dioxothietan-3-yl]-6-(oxan-4-ylmethoxy)-5-(trifluoromethyl)pyridine-2-carboxamide;
N-[3-(2-Amino-2-oxoethyl)-1,1-dioxothietan-3-yl]-6-(3-chloro-4-fluorophenyl)pyridine-2-carboxamide;
N-[3-(2-Amino-2-oxoethyl)-1,1-dioxothietan-3-yl]-5-cyclopropyl-6-(oxolan-2-ylmethoxy)pyridine-2-carboxamide;
N-[3-(2-Amino-2-oxoethyl)azetidin-3-yl]-5-cyclopropyl-6-[(4-fluorophenyl)methyl]pyridine-2-carboxamide;
N-[3-(2-Amino-2-oxoethyl)oxolan-3-yl]-6-(cyclopropylmethoxy)-5-(3,3-difluoroazetidin-1-yl)pyridine-2-carboxamide;
Benzyl 3-(2-amino-2-oxoethyl)-3-[[6-(cyclopropylmethoxy)-5-(3,3-difluoroazetidin-1-yl)pyridine-2-carbonyl]amino]pyrrolidine-1-carboxylate;
N-[3-(2-Amino-2-oxoethyl)pyrrolidin-3-yl]-6-(cyclopropylmethoxy)-5-(3,3-difluoroazetidin-1-yl)pyridine-2-carboxamide;

N-[4-(2-Amino-2-oxoethyl)piperidin-4-yl]-6-(cyclopropylmethoxy)-5-(3,3-difluoroazetidin-1-yl)pyridine-2-carboxamide;

N-[4-(2-Amino-2-oxoethyl)piperidin-4-yl]-5-cyclopropyl-6-(cyclopropylmethoxy)pyridine-2-carboxamide;

N-[3-(2-Amino-2-oxoethyl)oxolan-3-yl]-5-cyclopropyl-6-[(4-fluorophenyl)methyl]pyridine-2-carboxamide;

N-[3-(2-Amino-2-oxoethyl)oxolan-3-yl]-5-cyclopropyl-6-(cyclopropylmethoxy)pyridine-2-carboxamide;

N-[3-(2-Amino-2-oxoethyl)oxetan-3-yl]-6-(cyclopropylmethoxy)-5-(1-fluorocyclobutyl)pyridine-2-carboxamide;

N-[3-(2-Amino-2-oxoethyl)oxetan-3-yl]-6-(cyclopropylmethoxy)-5-(1-hydroxycyclobutyl)pyridine-2-carboxamide;

N-[3-(2-Amino-2-oxoethyl)thietan-3-yl]-6-(cyclopropylmethoxy)-5-(3,3-difluoroazetidin-1-yl)pyridine-2-carboxamide;

N-[3-(2-Amino-2-oxoethyl)-1,1-dioxothietan-3-yl]-6-(cyclopropylmethoxy)-5-(1-hydroxycyclobutyl)pyridine-2-carboxamide;

N-[3-(2-Amino-2-oxoethyl)oxetan-3-yl]-6-(cyclopropylmethoxy)-5-(3-fluorooxetan-3-yl)pyridine-2-carboxamide;

N-[3-(2-Amino-2-oxoethyl)oxetan-3-yl]-6-(cyclopropylmethoxy)-5-(3-hydroxyoxetan-3-yl)pyridine-2-carboxamide;

N-[3-(2-Amino-2-oxoethyl)thietan-3-yl]-6-(cyclopropylmethoxy)-5-(1-hydroxycyclobutyl)pyridine-2-carboxamide;

N-[3-(2-Amino-2-oxoethyl)thietan-3-yl]-5-cyclopropyl-6-(cyclopropylmethoxy)pyridine-2-carboxamide;

N-[3-(2-Amino-2-oxoethyl)thietan-3-yl]-6-(cyclopropylmethoxy)-5-(trifluoromethyl)pyridine-2-carboxamide; and N-[3-(2-Amino-2-oxoethyl)thietan-3-yl]-6-(cyclopropylmethoxy)-5-(3-fluorooxetan-3-yl)pyridine-2-carboxamide.

14. A compound according to claim 1 selected from

3-{[6-Cyclopropylmethoxy-5-(3,3-difluoro-azetidin-1-yl)-pyridine-2-carbonyl]-amino}-3-phenyl-propionic acid ethyl ester;

(+)-cis-5-Cyclopropyl-6-cyclopropylmethoxy-pyridine-2-carboxylic acid (2-carbamoyl-cyclohexyl)-amide;

(+)-5-Cyclopropyl-6-cyclopropylmethoxy-pyridine-2-carboxylic acid (2-carbamoyl-1-cyclohexyl-ethyl)-amide;

5-Cyclopropyl-6-cyclopropylmethoxy-pyridine-2-carboxylic acid (3-carbamoylmethyl-oxetan-3-yl)-amide;

6-Cyclopropylmethoxy-5-(3,3-difluoro-azetidin-1-yl)-pyridine-2-carboxylic acid (3-carbamoylmethyl-oxetan-3-yl)-amide;

(+)-5-Cyclopropyl-6-cyclopropylmethoxy-pyridine-2-carboxylic acid (2-carbamoyl-1-cyclopropyl-ethyl)-amide;

5-Cyclopropyl-6-cyclopropylmethoxy-pyridine-2-carboxylic acid [2-carbamoyl-1-(tetrahydro-pyran-4-yl)-ethyl]-amide;

6-Cyclopropylmethoxy-5-(3,3-difluoro-azetidin-1-yl)-pyridine-2-carboxylic acid (2-carbamoyl-1,1-dimethyl-ethyl)-amide;

5-Cyclopropyl-6-(2,2,3,3,3-pentafluoro-propoxy)-pyridine-2-carboxylic acid (3-carbamoylmethyl-oxetan-3-yl)-amide;

6-Cyclopropylmethoxy-5-(3,3-difluoro-azetidin-1-yl)-pyridine-2-carboxylic acid (1-carbamoylmethyl-2,2,2-trifluoro-ethyl)-amide;

6-Cyclopropylmethoxy-5-(3,3-difluoro-azetidin-1-yl)-pyridine-2-carboxylic acid (3-carbamoylmethyl-1,1-dioxo-1λ6-thietan-3-yl)-amide;

N-[4-(2-Amino-2-oxoethyl)piperidin-4-yl]-5-cyclopropyl-6-[(4-fluorophenyl)methyl]pyridine-2-carboxamide; hydrochloride;

N-[1-(2-Amino-2-oxoethyl)cyclobutyl]-6-(cyclopropylmethoxy)-5-(3,3-difluoroazetidin-1-yl)pyridine-2-carboxamide;

N-[3-(2-Amino-2-oxoethyl)-1,1-dioxothietan-3-yl]-5-cyclopropyl-6-(cyclopropylmethoxy)pyridine-2-carboxamide;

N-[3-(2-Amino-2-oxoethyl)-1,1-dioxothietan-3-yl]-5-cyclopropyl-6-(oxolan-2-ylmethoxy)pyridine-2-carboxamide;

N-[3-(2-Amino-2-oxoethyl)oxolan-3-yl]-6-(cyclopropylmethoxy)-5-(3,3-difluoroazetidin-1-yl)pyridine-2-carboxamide;

N-[3-(2-Amino-2-oxoethyl)oxetan-3-yl]-6-(cyclopropylmethoxy)-5-(1-fluorocyclobutyl)pyridine-2-carboxamide;

N-[3-(2-Amino-2-oxoethyl)-1,1-dioxothietan-3-yl]-6-(cyclopropylmethoxy)-5-(1-hydroxycyclobutyl)pyridine-2-carboxamide;

N-[3-(2-Amino-2-oxoethyl)thietan-3-yl]-6-(cyclopropylmethoxy)-5-(trifluoromethyl)pyridine-2-carboxamide; and N-[3-(2-Amino-2-oxoethyl)thietan-3-yl]-6-(cyclopropylmethoxy)-5-(3-fluorooxetan-3-yl)pyridine-2-carboxamide.

15. A process for the preparation of a compound according to claim 1, comprising the reaction of a compound of formula (A)

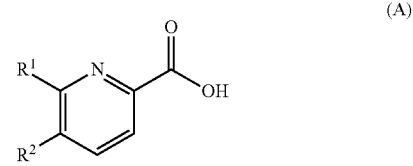

(A)

in the presence of $R^3$—$NH_2$, an amide coupling agent and a base;

wherein $R^1$ to $R^3$ are as defined in claim 1.

16. A compound manufactured according to a process of claim 15.

17. A pharmaceutical composition comprising a compound in accordance with claim 1 and a therapeutically inert carrier.

18. A method for the treatment of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis, which method comprises administering an effective amount of a compound as defined in claim 1 to a patient in need thereof.

* * * * *